US008620452B2

(12) United States Patent
King et al.

(10) Patent No.: US 8,620,452 B2
(45) Date of Patent: Dec. 31, 2013

(54) SELECTING ELECTRODE COMBINATIONS FOR STIMULATION THERAPY

(75) Inventors: Gary W. King, Fridley, MN (US); Gabriela C. Miyazawa, New Brighton, MN (US); Jordan J. Greenberg, Blaine, MN (US); Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 1580 days.

(21) Appl. No.: 11/810,943

(22) Filed: Jun. 7, 2007

(65) Prior Publication Data

US 2008/0046036 A1 Feb. 21, 2008

Related U.S. Application Data

(60) Provisional application No. 60/817,735, filed on Jun. 30, 2006, provisional application No. 60/873,220, filed on Dec. 6, 2006.

(51) Int. Cl.
*A61N 1/05* (2006.01)

(52) U.S. Cl.
USPC .......................................................... 607/116

(58) Field of Classification Search
USPC .................................... 607/67, 115–117, 152
See application file for complete search history.

(56) References Cited

U.S. PATENT DOCUMENTS

| | | | |
|---|---|---|---|
| 5,370,672 | A | 12/1994 | Fowler et al. |
| 5,501,703 | A | 3/1996 | Holsheimer et al. |
| 5,895,416 | A * | 4/1999 | Barreras et al. ................ 607/62 |
| 5,938,690 | A | 8/1999 | Law et al. |
| 6,622,048 | B1 | 9/2003 | Mann et al. |
| 6,714,822 | B2 | 3/2004 | King et al. |
| 6,871,099 | B1 | 3/2005 | Whitehurst et al. |
| 2004/0059395 | A1 | 3/2004 | North et al. |

(Continued)

FOREIGN PATENT DOCUMENTS

| | | |
|---|---|---|
| WO | 2006/110206 A | 10/2006 |
| WO | 2007/117347 A1 | 10/2007 |

OTHER PUBLICATIONS

Notification of Transmittal of the International Search Report and the Written Opinion of the International Searching Authority, or the Declaration, for corresponding patent application No. PCT/US2007/013443, mailed Dec. 13, 2007, 13 pages.

(Continued)

*Primary Examiner* — Carl H Layno
*Assistant Examiner* — Erica Lee
(74) *Attorney, Agent, or Firm* — Shumaker & Sieffert, P.A.

(57) ABSTRACT

Techniques for selecting electrode combinations for stimulation therapy include delivering stimulation via each of at least five combination groups. A first group of electrode combinations is characterized by the presence of a caudal anode. A second group of electrode combinations is characterized by the presence of a rostral anode. A third group of electrode combinations is characterized by the presence of a single anode above and a single anode below the cathode(s) of the combination. A fourth group of electrode combinations is characterized by the presence of multiple anodes above and below the cathode(s) of the combination. A fifth group of electrode combinations is characterized by the presence of transverse anodes. A sixth group of electrode combination is characterized by at least one off-center cathode. One or more preferred electrode combinations groups, and/or a number of leads to implant within the patient, may by selected based on patient feedback.

53 Claims, 35 Drawing Sheets

(56) References Cited

U.S. PATENT DOCUMENTS

| | | | |
|---|---|---|---|
| 2004/0143303 A1 | 7/2004 | Sieracki et al. | |
| 2004/0158298 A1* | 8/2004 | Gliner et al. | 607/48 |
| 2004/0267330 A1 | 12/2004 | Lee et al. | |
| 2005/0060009 A1 | 3/2005 | Goetz | |
| 2005/0075669 A1 | 4/2005 | King | |
| 2006/0122678 A1 | 6/2006 | Olsen et al. | |
| 2007/0027514 A1 | 2/2007 | Gerber | |

OTHER PUBLICATIONS

Notification Concerning Transmittal of International Preliminary Report on Patentability for corresponding patent application No. PCT/US2007/013443, mailed Jan. 15, 2009, 8 pages.

U.S. Appl. No. 11/402,652, entitled, "Autogeneration of Neurostimulation Therapy Program Groups," filed Apr. 12, 2006.

U.S. Appl. No. 11/402,657, entitled, "Rule-Based Stimulation Program Search," filed Apr. 12, 2006.

U.S. Appl. No. 11/352,389, entitled, "Shifting Between Electrode Combinations in Electrical Stimulation Device," filed Feb. 10, 2006.

U.S. Appl. No. 11/401,100, entitled, "Shifting Between Electrode Combinations in Electrical Stimulation Device," filed Apr. 10, 2006.

U.S. Appl. No. 11/810,967, entitled, "Selecting Electrode Combinations for Stimulation Therapy," filed Jun. 7, 2007.

U.S. Appl. No. 11/810,941, entitled, "Selecting Electrode Combinations for Stimulation Therapy," filed Jun. 7, 2007.

J. Holsheimer and J.J. Struijk, "How do Geometric Factors Influence Epidural Spinal Cord Stimulation?" Stereotactic and Functional Neurosurgery, vol. 56, pp. 234-249, 1991.

J. Holsheimer et al., "Effects of Electrode Geometry and Combination on Nerve Fibre Selectivity in Spinal Cord Stimulation," Medical & Biological Engineering & Computing, vol. 33, pp. 676-682, 1995.

J. Holsheimer and W.A. Wesselink, "Optimum Electrode Geometry for Spinal Cord Stimulation: The narrow Bipole and Tripole," Medical & Biological Engineering & Computing, vol. 35, pp. 493-497, 1997.

J. Holsheimer, and W.A. Wesselink, "Effect of Anode-Cathode Configuration on Paresthesia Coverage in Spinal Cord Stimulation," Neurosurgery, vol. 41, pp. 654-659, 1997.

Richard B. North, MD, et al., "Spinal Cord Stimulation for Axial Low Back Pain," SPINE, vol. 30, No. 12, pp. 1412-1418, 2005.

Richard B. North, MD, et al., "Spinal Cord Stimulation for Axial Low Back Pain: A Prospective Controlled Trial Comparing 16-Contact Insulated Electrodes with 4-Contact Percutaneous Electrodes," International Neuromodulation Society, vol. 9, No. 1, pp. 56-67, 2006.

Richard B. North, MD, et al., "Spinal Cord Stimulation Versus Repeated Lumbosacral Spine Surgery for Chronic Pain: A Randomized, Controlled Trial," Neurosurgery, vol. 56, No. 1, pp. 98-107, 2005.

Richard B. North, MD, et al., "Spinal Cord Stimulation Electrode Design: A Prospective, Randomized, Controlled Trial Comparing Percutaneous with Laminectomy Electrodes: Part I-Technical Outcomes," Neurosurgery, vol. 51, No. 2, pp. 381-390, 2002.

Richard B. North, MD, et al., "Spinal Cord Stimulation Electrode Design: A Prospective, Randomized, Controlled Trial Comparing Percutaneous with Laminectomy Electrodes: Part II-Clinical Outcomes," Neurosurgery, vol. 57, No. 5, pp. 990-996, 2005.

Richard B. North, MD, et al., "Spinal Cord Stimulation for Chronic Pain of Spinal Origin," SPINE, vol. 27, No. 22, pp. 2584-2591, 2002.

Jan Holsheimer, PhD., "Which Neuronal Elements are Activated Directly by Spinal Cord Stimulation," Neuromodulation, vol. 5, No. 1, pp. 25-31, 2002.

Office Action for U.S. Appl. No. 11/810,967, mailed May 26, 2009, 9 pages.

Preliminary Amendment and Response to Restriction Requirement for U.S. Appl. No. 11/810,967, filed Jun. 26, 2009, 10 pages.

Office Action for U.S. Appl. No. 11/810,941, mailed May 26, 2009, 8 pages.

Preliminary Amendment and Response to Restriction Requirement for U.S. Appl. No. 11/810,941, filed Jun. 26, 2009, 9 pages.

Office Action for U.S. Appl. No. 11/810,967, mailed Jul. 24, 2009, 20 pages.

Office Action for U.S. Appl. No. 11/810,941, mailed Jul. 24, 2009, 22 pages.

Responsive Amendment for U.S. Appl. No. 11/810,967, filed Oct. 26, 2009, 20 pages.

Final Office Action for U.S. Appl. No. 11/810,967, mailed Dec. 10, 2009, 13 pages.

Final Office Action for U.S. Appl. No. 11/810,941, mailed Jan. 13, 2010, 14 pages.

Office action for U.S. Appl. No. 11/810,967, mailed Jun. 27, 2013, 23 pages.

Decision on Appeal for U.S. Appl. No. 11/810,941, mailed Jul. 31, 2013, 10 pp.

Response to Office Action dated Jun. 27, 2013, from U.S. Appl. No. 11/810,967, filed Sep. 27, 2013, 22 pp.

* cited by examiner

| | A | B | C | D | E | F | G | H | I | J | K | L | M | N | O | P | Q | R |
|---|---|---|---|---|---|---|---|---|---|---|---|---|---|---|---|---|---|---|
| VDC | 1.647 | 1.312 | 1.157 | 1.647 | 1.312 | 1.157 | 1.398 | 1.125 | 1.129 | 1.181 | 1.098 | 1.415 | 1.420 | 3.787 | 2.062 | 2.062 | 1.703 | 1.786 |
| VDC/VDR | 0.528 | 0.615 | 0.587 | 0.419 | 0.475 | 0.459 | 0.403 | 0.469 | 0.447 | 0.471 | 0.449 | 0.471 | 0.528 | 0.352 | 0.437 | 0.340 | 0.356 | 0.531 |
| VMAX | 4.365 | 2.889 | 2.760 | 5.499 | 3.866 | 3.531 | 4.850 | 3.355 | 3.538 | 3.510 | 3.423 | 4.208 | 3.763 | 15.079 | 6.600 | 8.497 | 6.696 | 4.707 |
| UR | 2.651 | 2.278 | 2.386 | 3.340 | 2.946 | 3.053 | 3.470 | 2.982 | 3.135 | 2.972 | 3.118 | 2.974 | 2.651 | 3.982 | 3.201 | 4.121 | 3.932 | 2.635 |
| IMAX | 4.446 | 4.001 | 4.131 | 5.620 | 5.184 | 5.279 | 6.687 | 5.628 | 5.990 | 5.708 | 5.896 | 5.638 | 5.095 | 21.395 | 10.507 | 13.497 | 11.338 | 9.783 |
| DMEAN | 0.463 | 0.394 | 0.417 | 0.628 | 0.575 | 0.588 | 0.510 | 0.466 | 0.490 | 0.466 | 0.479 | 0.495 | 0.423 | 0.513 | 0.464 | 0.602 | 0.527 | 0.529 |
| DMAX | 1 | 0.8 | 0.9 | 1.3 | 1.2 | 1.2 | 1.1 | 1 | 1.1 | 1 | 1 | 1 | 0.9 | 1.2 | 1.1 | 1.4 | 1.2 | 1 |
| SIGMAX | 1.674 | 1.684 | 1.666 | 1.882 | 1.872 | 1.865 | 1.741 | 1.662 | 1.718 | 1.656 | 1.686 | 1.803 | 1.670 | 1.016 | 1.332 | 1.508 | 1.490 | 1.908 |
| AREA | 5.245 | 4.360 | 4.670 | 7.630 | 6.785 | 6.935 | 5.945 | 5.245 | 5.690 | 5.225 | 5.410 | 5.760 | 4.735 | 3.845 | 4.525 | 6.480 | 5.595 | 5.985 |
| AREAFACTOR | 0.138 | 0.117 | 0.125 | 0.166 | 0.154 | 0.158 | 0.147 | 0.140 | 0.143 | 0.141 | 0.142 | 0.137 | 0.127 | 0.252 | 0.174 | 0.200 | 0.177 | 0.139 |
| DR SPAN | 6 | 6.3 | 6.1 | 6 | 5.9 | 5.9 | 4.3 | 4.5 | 4.5 | 4.5 | 4.4 | 4.7 | 5.1 | 7.8 | 6.4 | 6.4 | 4.7 | 2 |

Fiber Selectivity

ELECTRODE COMBINATION A
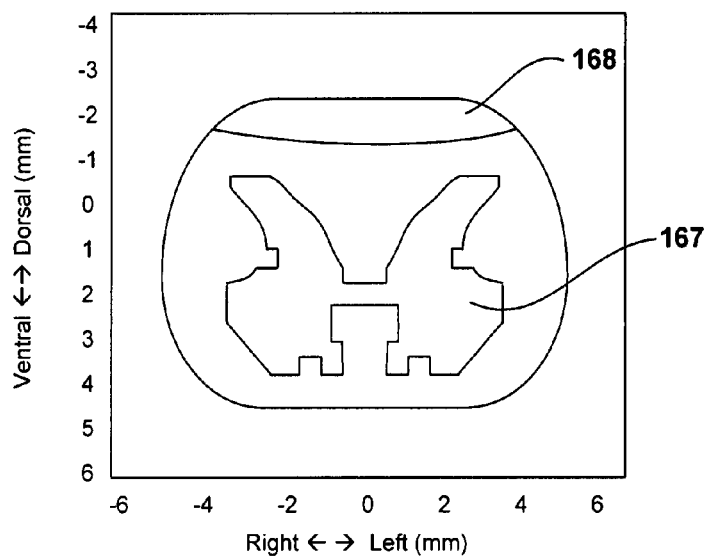
ELECTRODE COMBINATION B
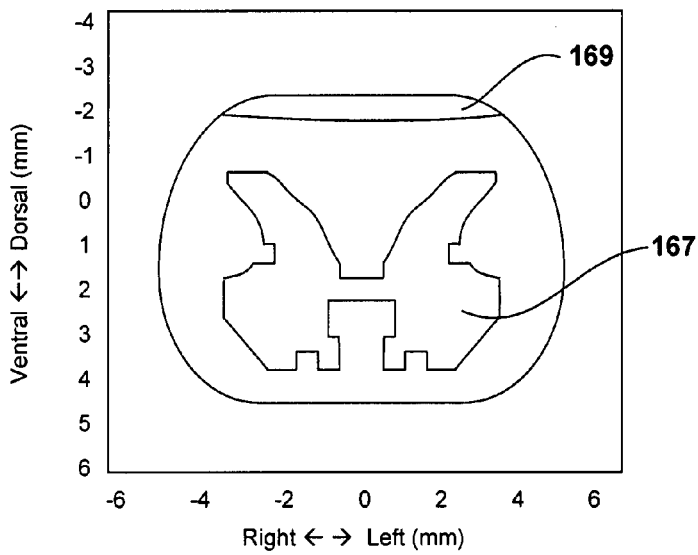
FIG. 15

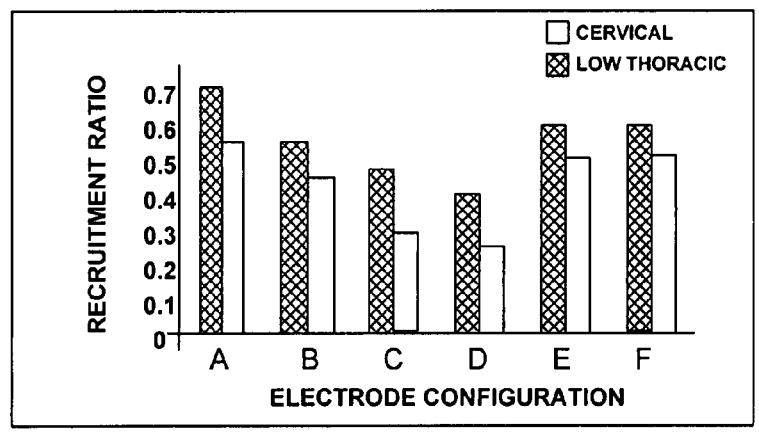
FIG. 17A
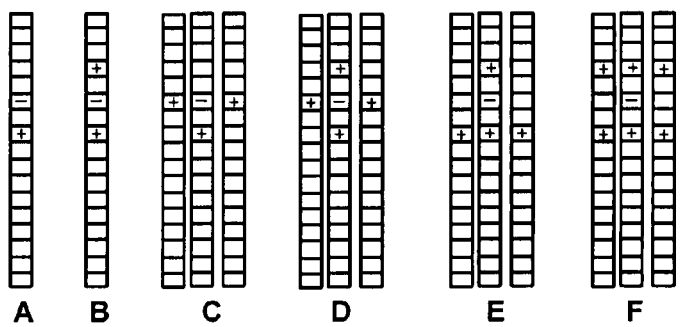
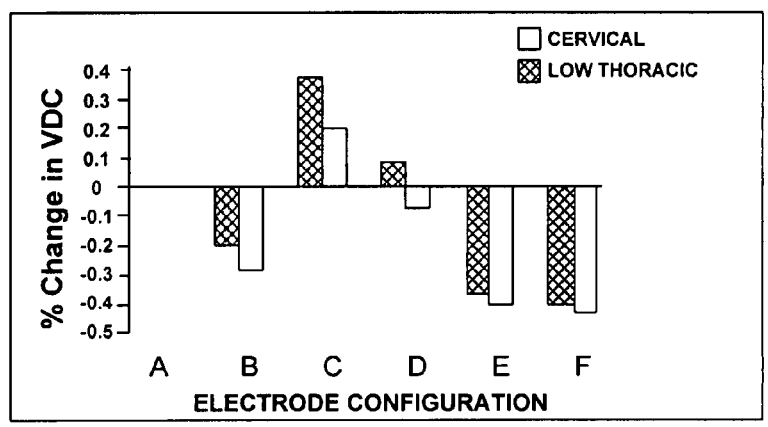
FIG. 17B

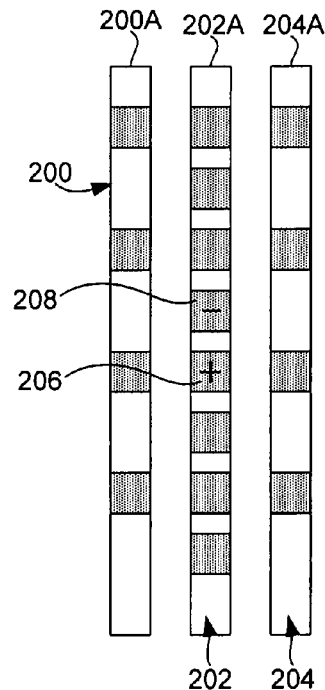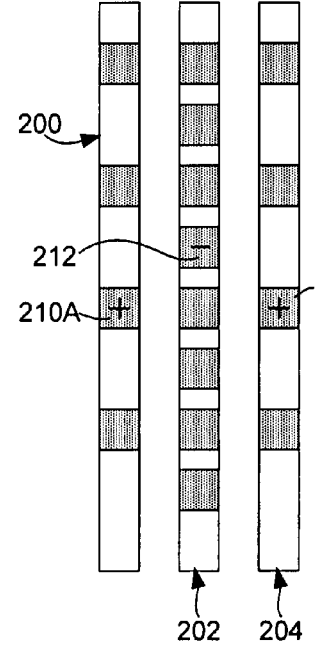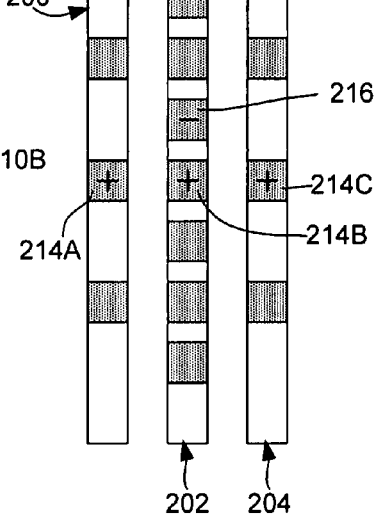
FIG. 19A  FIG. 19B  FIG. 19C
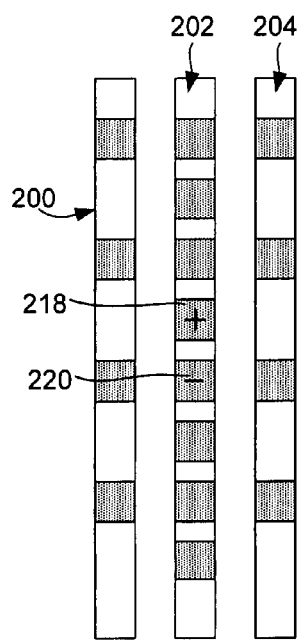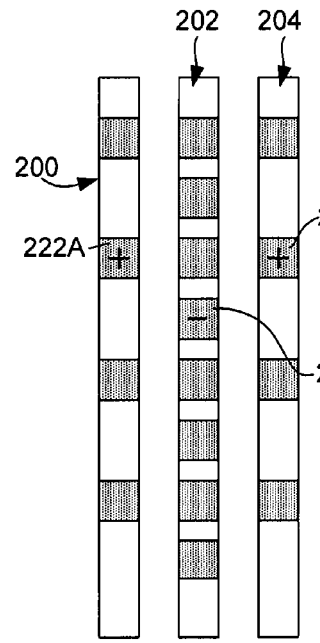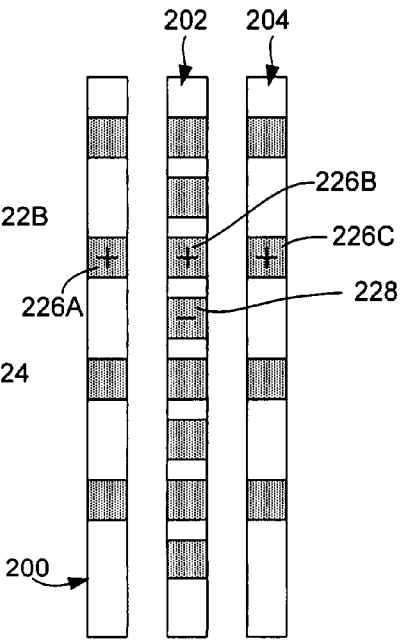
FIG. 20A  FIG. 20B  FIG. 20C

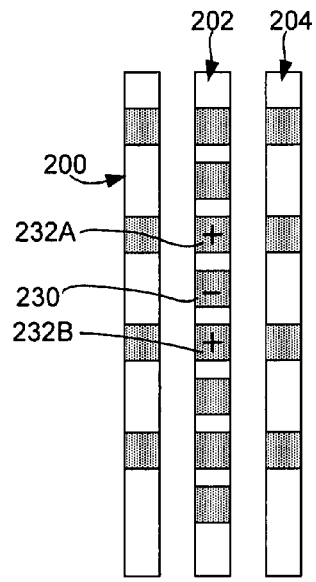
FIG. 21
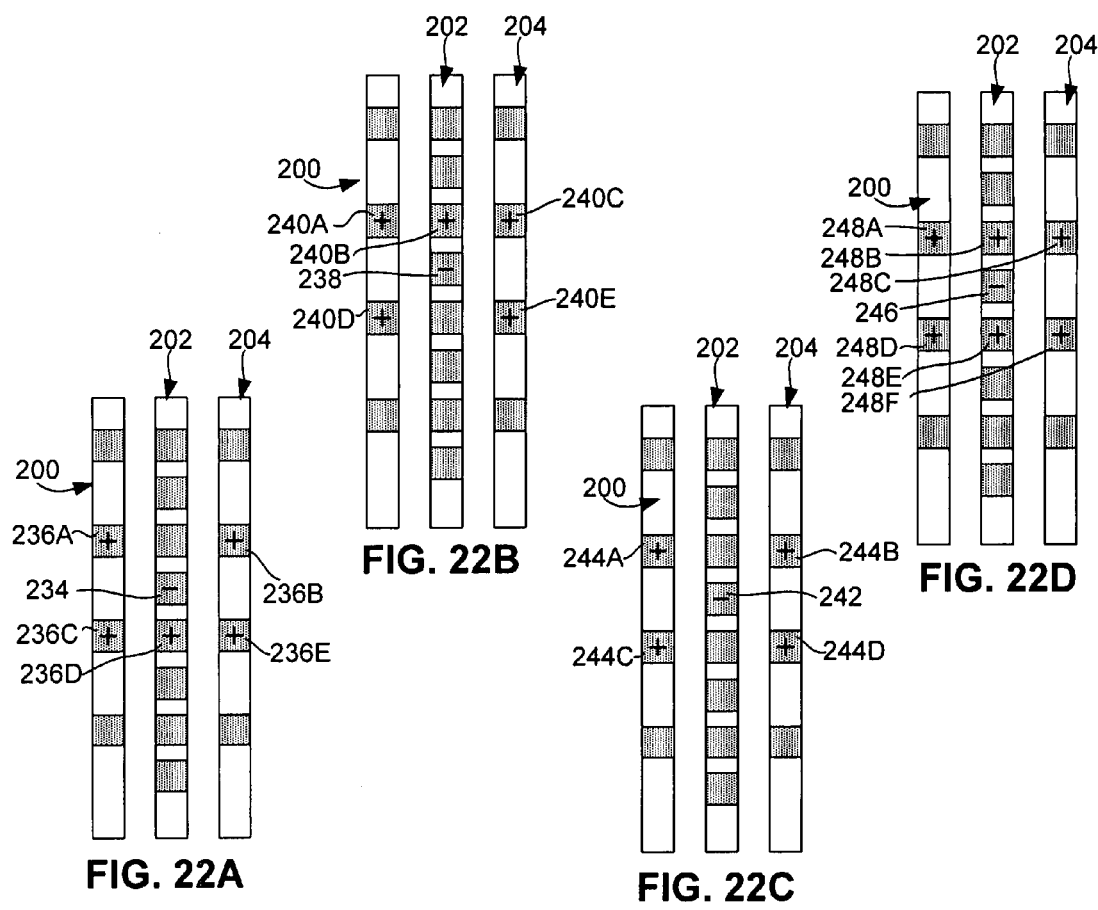
FIG. 22A  FIG. 22B  FIG. 22C  FIG. 22D

FIG. 27

|  | VDC (V) | Recruitment Ratio | Usage Range | Dmean (mm) | Area Factor (mm) | MIDspan (cm) | DRspan (cm) |
|---|---|---|---|---|---|---|---|
| Group A | 1.372 | 0.577 | 2.438 | 0.425 | 0.127 | 3.051 | 6.133 |
| Group B | 1.372 | 0.451 | 3.113 | 0.596 | 0.159 | -2.315 | 5.933 |
| Group C | 1.398 | 0.403 | 3.470 | 0.510 | 0.147 | 0.601 | 4.300 |
| Group D | 1.133 | 0.459 | 3.052 | 0.475 | 0.141 | 0.414 | 4.475 |
| Group E | 2.403 | 0.371 | 3.809 | 0.526 | 0.201 | 0.789 | 6.325 |

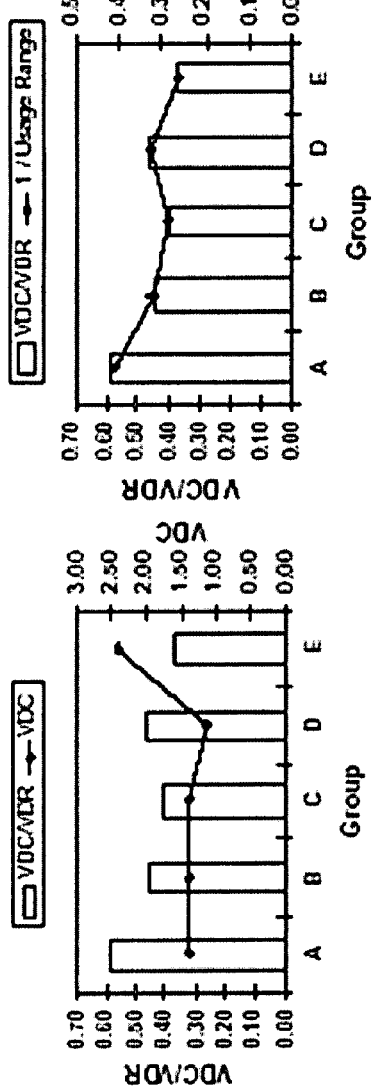
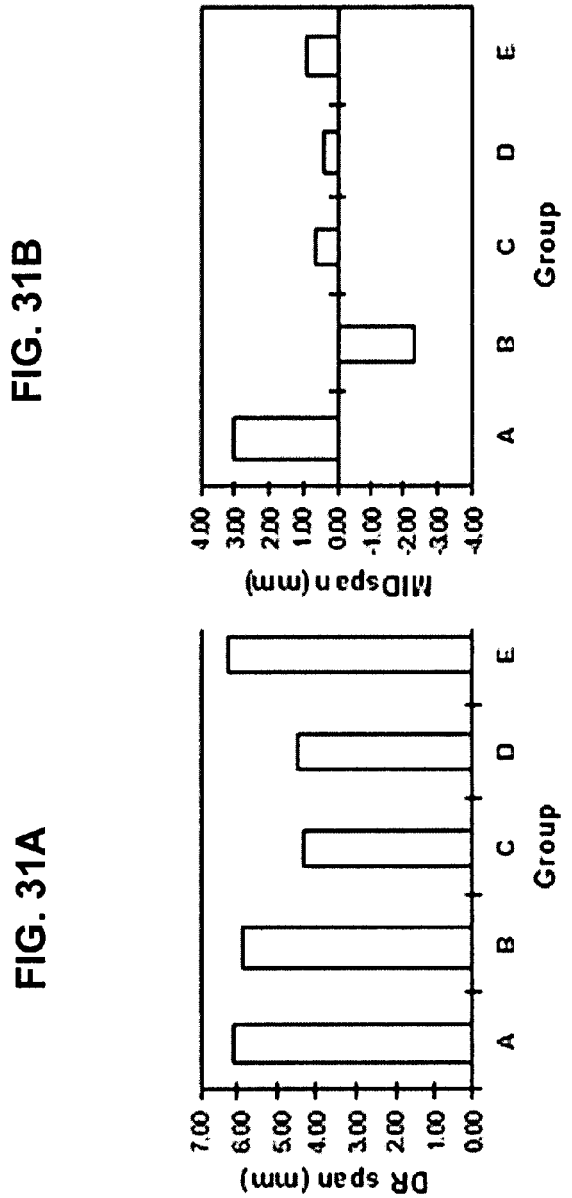
FIG. 31B
FIG. 31A
FIG. 32B
FIG. 32A

FIG. 34A

| VDC | 12.842 |
|---|---|
| VDC/VDR | 1.232 |
| VMAX | 14.588 |
| U.R. | 1.4 |
| IMAX | 19.766 |
| DMEAN | 0.037 |
| DMAX | 0.1 |
| X S.D. | 0.435 |
| AREA | 0.125 |
| AREA FACTOR | 0.043 |
| DR SPAN | 4.7 |

FIG. 34B

| VDC | 1.515 |
|---|---|
| VDC/VDR | 0.71 |
| VMAX | 2.986 |
| U.R. | 1.971 |
| IMAX | 5.853 |
| DMEAN | 0.354 |
| DMAX | 0.5 |
| X S.D. | 2.03 |
| AREA | 3.735 |
| AREA FACTOR | 0.087 |
| DR SPAN | 4 |

SELECTING ELECTRODE COMBINATIONS FOR STIMULATION THERAPY

This application claims the benefit of U.S. Provisional Application No. 60/817,735, filed Jun. 30, 2006, and U.S. Provisional Application No. 60/873,220, filed Dec. 6, 2006. The entire content of U.S. Provisional Application Nos. 60/817,735 and 60/873,220 is incorporated herein by reference.

TECHNICAL FIELD

The present invention relates to electrical stimulation therapy. More particularly, the present invention relates to techniques for selecting combinations of implanted electrodes for delivery of stimulation to a patient.

BACKGROUND

Implantable medical devices may be used to deliver electrical stimulation therapy to patients to treat a variety of symptoms or conditions such as chronic pain, tremor, Parkinson's disease, epilepsy, urinary or fecal incontinence, or gastroparesis. An implantable medical device may deliver electrical stimulation therapy via leads that include electrodes located proximate to the spinal cord, pelvic nerves, stomach, or within the brain of a patient. In general, the implantable medical device delivers electrical stimulation therapy in the form of electrical pulses.

A clinician may select values for a number of programmable therapy parameters in order to define the electrical stimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient. The clinician may also select as parameters particular electrodes within an array of electrodes located on, for example, one or two implanted leads, to be used to deliver the pulses, as well as the polarities of the selected electrodes. A group of parameter values may be referred to as a program in the sense that they drive the electrical stimulation therapy to be delivered to the patient.

The process of selecting values for the parameters that provide adequate results can be time consuming, and may require a great deal of trial and error before a "best" program is discovered. The "best" program may be a program that is better in terms of clinical efficacy (e.g., symptom relief, coverage area) versus side effects experienced and medical device performance characteristics (e.g., power consumption) than other programs tested. As a portion of the overall parameter selection process, the process of selecting electrodes and the polarities of the electrodes, e.g., the process of selecting electrode combinations, can be particularly time-consuming and tedious. The clinician may need to test all possible combinations of electrodes within the set implanted in the patient, or a significant portion thereof, in order to identify a "best" combination of electrodes and their polarities.

In some cases, the clinician may test combinations by manually specifying each combination to test based on intuition or some idiosyncratic methodology, and recording notes on the efficacy and side effects of each combination after delivery of stimulation via that combination. In this manner, the clinician is able to later compare and select from the tested combinations. As an example illustrating the magnitude of such a task, implantable medical devices commonly deliver spinal cord stimulation therapy (SCS) to a patient via two leads that include eight electrodes per lead and provide well over one million potential electrode combinations.

Prior to implanting an implantable medical device, a trial stimulator may be used to deliver stimulation, e.g., SCS, to the patient during a trial (or trialing) period. The trial stimulator may be an external stimulator coupled to one or more percutaneously implanted leads. The result of the trial period is a general indication as to whether stimulation will be an efficacious therapy for the patient. Based on the trial period, a decision as to whether to implant an implantable medical device and leads for chronic delivery of stimulation may be made. The lengthy trial and error process of selecting electrode combinations occurs not only prior to implanting the implantable medical device and leads, but may also occur periodically for the life of the therapy. For example, the lengthy trial and error process of selecting electrode combinations occurs only after implanting the implantable medical device and leads.

SUMMARY

In general, the invention is directed toward techniques for identifying combinations of electrodes from among an array of electrodes implanted within a patient and electrically coupled to a medical device. A selected subset of the electrodes located on one or more leads and the polarities of the electrodes of the subset collectively define an "electrode combination," which is also referred to as an "electrode pattern." An electrode combination defines a combination of single or multiple cathode electrodes and single or multiple anode electrodes. Stimulation current flows between the cathodes and anodes for delivery of electrical stimulation therapy.

In one embodiment, the invention is directed to techniques that first involve a preliminary determination of a class of electrode combinations that provide efficacious stimulation for the particular patient. In another embodiment, the invention is directed to techniques that involve a preliminary determination of a group of electrode combinations that provide efficacious stimulation for the particular patient, where the group of electrode combinations is a subset of combinations from two or more classes of electrode combinations. The techniques may be employed by either a clinician or patient, and may involve delivery of stimulation by an external medical device via percutaneously implanted leads during a therapy evaluation period or by an implanted medical device via implanted leads after a therapy system has been implanted for therapy delivery on a chronic basis. However, the therapy evaluation period is not limited to stimulation delivered via percutaneously implanted leads, but may include transcutaneously implanted leads or surgically implanted leads.

Some embodiments of the invention selectively test a plurality of combinations within at least two classes of electrode combinations. Based on the results of the testing, a class of electrode combinations may be identified as being best suited for the patient. A clinician may then test within the selected class to select one or more specific electrode combinations to implement in a therapy for the patient. Both the best suited class and electrode combination may be chosen based on various factors, such as clinical efficacy versus side effects experienced, and power consumption.

A first class of electrode combinations includes combinations with electrodes from one or two columns of electrodes within an array of electrodes. A second class of electrode combinations includes combinations with electrodes from at least three columns of electrodes within the array of electrodes. Accordingly, for selective delivery of stimulation via electrode combinations from both classes, a medical device, such as an external trial stimulator, is coupled to an implanted electrode array that includes at least three columns of electrodes. In a spinal cord stimulation (SCS) embodiment, the columns of the electrode array are arranged substantially longitudinally with respect to the spinal cord of the patient. The columns of electrodes may be disposed on three separate percutaneous leads, which may be substantially cylindrical, a single paddle lead, or a combination percutaneous and paddle leads.

The electrode combinations within the second class may include combinations with one or more cathodes along a middle column of electrodes, or combinations with one or more off-center cathodes, e.g., combination in which the middle column of electrodes does not include any cathodes. Within the second class of combinations are at least two subclasses of electrode combinations. A first subclass of the second class is transverse electrode combinations. A second subclass of the second class is longitudinal electrode combinations. However, the second class is not necessarily limited to these subclasses. Transverse electrode combinations include combinations with electrodes located in at least three columns, and include at least one anode on either side of a cathode. Transverse electrode combinations may include, for example, at least three electrodes arranged substantially along a line approximately perpendicular or otherwise transverse to a longitudinal axis of one or more lead bodies, and/or a longitudinal axis of a spinal cord. Delivery of stimulation via transverse electrode combinations may result in stimulation fields oriented substantially perpendicular or otherwise transverse to a longitudinal axis of one or more lead bodies, and/or a longitudinal axis of a spinal cord.

Longitudinal electrode combinations include electrodes from at least three columns of electrodes, with anodes of the electrode combination displaced substantially longitudinally on one or both sides of a cathode of the electrode combination. Longitudinal combinations may include, for example, at least one anode and one cathode arranged along a line approximately parallel or otherwise along a longitudinal axis of one or more lead bodies and/or a spinal cord. Delivery of stimulation via longitudinal electrode combinations may result in stimulation fields oriented substantially parallel to a longitudinal axis of one or more lead bodies, and/or a longitudinal axis of a spinal cord.

In other embodiments of the invention, a technique for identifying effective electrode combinations for a patient includes testing electrode combinations from within at least five groups of electrode combinations. The at least five groups of electrode combinations represent a range of stimulation fields that may be achieved within the first and second classes of combinations discussed above. That is, the combinations within the five or more groups of electrode combinations are a part of one or both of the first or second classes of combinations. For example, the first group may include combinations from both the first and second classes of combinations discussed above. In some embodiments, the at least five groups of electrode combinations includes at least six groups of electrode combinations. In one of the at least six groups of electrode combinations, one or more cathodes of the combinations are located off-center (i.e., the cathodes are not located on the middle/center column of electrodes).

Computer modeling of the stimulation field achieved with the five or more groups suggests that combinations from each group result in at least one substantially different metric value (e.g., usage range, which may be defined as the maximum tolerated amplitude of stimulation divided by the threshold amplitude for sensations or recruitment ratio) than another group. Thus, testing within the groups may enable a clinician to optimize certain metric values for a therapy program.

A first group of electrode combinations is characterized by the presence of caudal anodes, in which the anodes of the combination are located below (i.e., closer to the proximal end of the lead) the cathode(s) of the combination. A second group of electrode combinations is characterized by the presence of rostral anodes, in which the anodes of the combination are located above the cathode(s) of the combination (i.e., closer to a distal end of the lead). A third group of electrode combinations is characterized by the presence of a single anode above and a single anode below the cathode(s) of the combination. A fourth group of electrode combinations is characterized by the presence of multiple anodes above and below the cathode(s) of the combination. A fifth group of electrode combinations is characterized by the presence of transverse anodes, in which at least one anodes of the combination is located substantially transverse to a cathode of the combination. "Above" refers generally to a location closer to a distal end of the lead, while "below" refers generally to a location further from a distal end of the lead. In some cases, leads may be implanted within a patient such that the distal ends do not face the same direction, or that a distal end of one of the leads faces the feet of the patient rather than the head. Leads may also be implanted in certain regions of a patient such that the distal ends of the leads do not necessarily face the head or feet of a patient, e.g., on a surface of a brain of a patient.

A sixth group of electrode combinations, which is tested according to some embodiments of the invention, is characterized by the presence of one or more transverse or off-center cathodes, i.e., the cathodes of combinations within the sixth group are not located on the middle/center column of electrodes. Combinations within the sixth group may include characteristics of the other five groups of combinations. In other words, combinations within the sixth group may include rostral anodes, caudal anodes, and so forth.

Based on the results of the testing of electrode combinations within one or more of the groups, one of the groups of electrode combinations may be identified as being best suited for the patient. A clinician may then test within the selected group to identify one or more specific electrode combinations to implement into a therapy program (e.g., program into an electrical stimulator for chronic stimulation therapy) for the patient. As with the technique involving testing within two classes, when testing within groups, both the best suited group and electrode combination may be chosen based on various factors, such as clinical efficacy versus side effects experienced, and power consumption.

Upon finding a best suited class, group or electrode combination, the clinician or patient may utilize programming methodologies to fine-tune (i.e., further optimize) the selected class, group or electrode combination. The methodologies may include, for example, steering stimulation along or between leads to help find a preferred locus for delivery of stimulation from the combination, optimizing stimulation parameters (e.g., stimulation amplitude, pulse width, pulse rate, etc.), or generating additional combinations based on the best suited class, group or electrode combination, such as permutations of combinations within the best suited class or group, or permutations of the best suited electrode combination.

Identifying useful classes or groups of electrode combinations in accordance with the techniques described in the present disclosure prior to initiating other programming methodologies may help decrease the amount of time required to find one or more electrode combinations for programming into a medical device. Initially identifying the classes or groups of electrode combinations is a relatively time effective technique for identifying a useful electrode combination because the classes and groups of electrode combinations are representative of a broad range of therapeutic results that may be achieved by the many, and sometimes millions, of possible electrode combinations.

In some embodiments, the array of electrodes implanted within the patient includes three columns of electrodes. A first of the columns may include four electrodes, a second of the columns may include eight electrodes, and a third of the columns may include four electrodes. This arrangement may be referred to as a 4-8-4 arrangement of electrodes.

In some embodiments, a patient and/or clinician systematically tests an initial set of electrode combinations, e.g., six to eighteen combinations of electrodes. The initial set includes at least one electrode combination from each of the first and second class of electrode combinations or from each of the at least five groups of electrode combinations. Both transverse and longitudinal electrode combinations may be represented in the second class. Each combination of the initial set is tested for a relatively short duration of time (e.g., less than an hour). Based on the results of the systematic testing, the patient and/or clinician selects a narrower subset of combinations from the initial set, and tests each of the combinations in the narrower set for a longer duration of time (e.g., one or more days), during a therapy evaluation period. The testing may be done to achieve pain relief goals for the patient. Based on the testing of the narrower set, a clinician may decide which class of electrode combinations, or a particular electrode combination from within one of the classes, should programmed into a implanted medical device implanted in the patient for chronic delivery of stimulation, e.g., SCS.

In some embodiments, a clinician and/or patient selects a best electrode combination, class, or group based on testing electrode combinations from a library of combinations that includes a predetermined set of stored electrode combinations. In one embodiment, the stored combinations are representative of at least the first and second classes of combinations identified above (e.g., combinations utilizing one to two columns of electrodes, as well as combinations utilizing three columns of electrodes). In another embodiment, the stored combinations are representative of the five or more groups of combinations identified above. By selecting from a predetermined set of stored electrode combinations, embodiments of invention may allow the clinician or patient to identify the most effective class of electrode combinations, or in some embodiments, the most effective group of electrode combinations within the classes. By initially identifying a class of electrode combinations, the clinician or patient may be able to more quickly identify effective electrode combinations by testing combinations within the effective class (or group), rather than all possible combinations, after internalization of an implantable medical device.

In other embodiments, the invention is directed to computer-readable media containing instructions for causing a programmable processor to perform any of the methods described herein, such as selecting or delivering stimulation via an electrode combination from a stored set of electrode combinations that are representative of the first and second class of electrode combinations or the five or more groups of electrode combinations.

In another embodiment, the invention is directed to a device that includes a processor. The processor selects an electrode combination for delivery of neurostimulation therapy to a patient from a stored set of electrode combinations that are representative of the first and second class of electrode combinations or the five or more groups of electrode combinations. The device may be a programming device associated with one of a clinician and a patient, or a medical device configured to deliver electrical stimulation to a patient.

Embodiments of the invention may provide advantages. For example, electrode combinations within different classes or groups may result in different stimulation fields. Accordingly, testing at least one representative combination from each class and/or group may help decrease the amount a clinician may invest to select an effective electrode combination for a patient. The effect of the different stimulation fields may be characterized by a plurality of therapy (or "efficacy") metrics such as, but not limited to, the extent to which dorsal column fibers are stimulated, the ratio of dorsal column fiber stimulation to dorsal root stimulation, or the depth of tissue stimulated, which may be similar within a class, but different between classes. The therapy metrics may also help decrease the amount of time a clinician spends selecting an effective electrode combination. In some cases, the clinician may express a desired program in terms of clinically relevant therapy metrics.

Due to the anatomical and symptom differences between patients, one class of electrode combinations may be more effective for one patient than the other patients. Alternatively, one group of combinations from within the classes may be more effective than the other groups. Some embodiments of the invention may allow a clinician or the patient to identify the effective class, while other embodiments of the invention may allow the clinician or patient to identify the effective group. This identification may reduce the scope of a search for electrode combinations, and may also allow a more informed determination of what lead configuration, e.g., the number of leads or columns and rows of electrodes, to implant within the patient.

In one embodiment, the disclosure is directed toward a method comprising delivering stimulation to a patient via at least one of three columns of electrodes implanted within the patient, wherein the stimulation is delivered according to a trial electrode combination from each of at least five groups of electrode combinations during a therapy evaluation period. A first group is characterized by a rostral anode electrode pattern, a second group is characterized by a caudal anode electrode pattern, and a third group is characterized by a first cathode disposed between two anodes, the first cathode and anodes being located in a same column of electrodes. A fourth group is characterized by a second cathode disposed between a first row of anodes and a second row of anodes, and a fifth group is characterized by a transverse electrode combination, where anodes of the transverse electrode combination are displaced substantially transversely relative to a third cathode of the transverse electrode combination, and a stimulation field resulting from delivery of stimulation via the transverse combination is oriented substantially transversely relative to a target tissue for the stimulation.

In another embodiment, the disclosure is directed toward a system comprising a medical device, an array of implantable electrodes coupled to the medical device, where the array defines a first electrode column, a second electrode column, and a third electrode column, and a memory. The memory stores at least one electrode combination from each one of at least five groups of electrode combinations. The medical device delivers therapy to a patient via the array of implantable electrodes according to a trial electrode combination from each of the at least five groups. The at least five groups comprise a first group characterized by a rostral anode electrode pattern, a second group characterized by a caudal anode electrode pattern, a third group characterized by a first cathode disposed between two anodes, the first cathode and anodes being located in a same one of the first, second or third electrode columns, a fourth group characterized by a second cathode disposed between a first row of anodes and a second row of anodes, and a fifth group characterized by a transverse electrode combination, where anodes of the transverse electrode combination are displaced substantially transversely relative to a third cathode of the transverse electrode combination, and a stimulation field resulting from delivery of stimulation via the transverse combination is oriented substantially transversely relative to a target tissue for the stimulation.

In another embodiment, the disclosure is directed toward a medical device programmer comprising a memory that stores a plurality of electrode combinations for an electrical stimulator, and a processor. The plurality of electrode combinations includes at least one electrode combination from each of at least five groups of electrode combinations. The at least five groups comprise a first group characterized by a rostral anode electrode pattern, a second group characterized by a caudal anode electrode pattern, a third group characterized by a first cathode disposed between two anodes, the first cathode and anodes being located in a same column of electrodes, a fourth group characterized by a second cathode disposed between a first row of anodes and a second row of anodes, and a fifth group characterized by a transverse electrode combination, where anodes of the transverse electrode combination are displaced substantially transversely relative to a third cathode of the transverse electrode combination, and a stimulation field resulting from delivery of stimulation via the transverse combination is oriented substantially transversely relative to a target tissue for the stimulation. The processor controls delivery of electrical stimulation to a patient via the electrical stimulator in accordance with at least one electrode combination from the first, second, third, fourth, and fifth groups.

In another embodiment, the disclosure is directed toward a computer-readable medium comprising instructions. The instructions cause a processor to control an electrical stimulator to deliver electrical stimulation to a patient during a therapy evaluation period via an electrode combination from each of at least five groups of electrode combinations. The at least five groups comprise a first group of electrode combinations characterized by a rostral anode electrode pattern, a second group of electrode combinations characterized by a caudal anode electrode pattern, a third group of electrode combinations characterized by a first cathode disposed between two anodes, the first cathode and anodes being located in a same column of electrodes, a fourth group of electrode combinations characterized by a second cathode disposed between a first row of anodes and a second row of anodes, and a fifth group of electrode combinations characterized by a transverse electrode combination, where anodes of the transverse electrode combination are displaced substantially transversely relative to a third cathode of the transverse electrode combination, and a stimulation field resulting from delivery of stimulation via the transverse combination is oriented substantially transversely relative to a target tissue for the stimulation.

In another embodiment, the disclosure is directed toward a computing device comprising a memory comprising a plurality of electrode combinations and associated therapy metric values, a display, and a processor. The plurality of electrode combinations comprises at least one electrode combination from at least five groups of electrode combinations. The at least five groups comprise a first group characterized by a rostral anode electrode pattern, a second group characterized by a caudal anode electrode pattern, a third group characterized by a first cathode disposed between two anodes, the first cathode and anodes being located in a same column of electrodes, a fourth group characterized by a second cathode disposed between a first row of anodes and a second row of anodes, and a fifth group characterized by a transverse electrode combination, wherein anodes of the transverse electrode combination are displaced substantially transversely relative to a third cathode of the transverse electrode combination, and a stimulation field resulting from delivery of stimulation via the transverse combination is oriented substantially transversely relative to a target tissue for the stimulation. The processor generates a graphical display illustrating at least one electrode combination from the plurality of electrode combinations and the associated therapy metric value to a user via the display.

In another embodiment, the disclosure is directed toward a method comprising selecting a therapy metric, and selecting at least one group from a set of at least five groups of electrode combinations that optimizes the therapy metric. The set of at least five groups comprise a first group of electrode combinations characterized by a rostral anode electrode pattern, a second group of electrode combinations characterized by a caudal anode electrode pattern, a third group of electrode combinations characterized by a first cathode disposed between two anodes, the first cathode and anodes being located in a same column of electrodes, a fourth group of electrode combinations characterized by a second cathode disposed between a first row of anodes and a second row of anodes, and a fifth group of electrode combinations characterized by a transverse electrode combination, where anodes of the transverse electrode combination are displaced substantially transversely relative to a third cathode of the transverse electrode combination, and a stimulation field resulting from delivery of stimulation via the transverse combination is oriented substantially transversely relative to a target tissue for the stimulation.

The details of one or more embodiments of the invention are set forth in the accompanying drawings and the description below. Other features, objects, and advantages of the invention will be apparent from the description and drawings, and from the exemplary descriptions.

BRIEF DESCRIPTION OF DRAWINGS

FIG. 15 illustrates another graphical display generated via the first computer modeling example.

FIGS. 17A-B relate to a third computer modeling example, in which a plurality of electrode combinations from each of the two classes were modeled for two different cerebral spinal fluid (CSF) depths.

FIGS. 19A-C are schematic diagrams illustrating various representative electrode combinations from a first group of electrode combinations.

FIG. 20A-C are schematic diagrams illustrating various representative electrode combinations from a second group of electrode combinations.

FIG. 21 is a schematic diagram illustrating a representative electrode combination from a third group of electrode combinations.

FIGS. 22A-D are schematic diagrams illustrating various representative electrode combinations from a fourth group of electrode combinations.

FIG. 27 is an example chart for recording patient feedback to testing of combinations within each of at least five groups.

FIGS. 31A-B are graphs that chart results of computer modeling and compare the fiber selectivity attributes of five groups of electrode combinations.

FIGS. 32A-B are graphs that chart results of computer modeling and compare the dorsal root activation attributes of five groups of electrode combinations.

FIG. 34A is a table illustrating a plurality of metrics for the electrode combination shown in FIG. 33A.

FIG. 34B is a table illustrating a plurality of metrics for the electrode combination shown in FIG. 33C.

DETAILED DESCRIPTION

Figure 1:
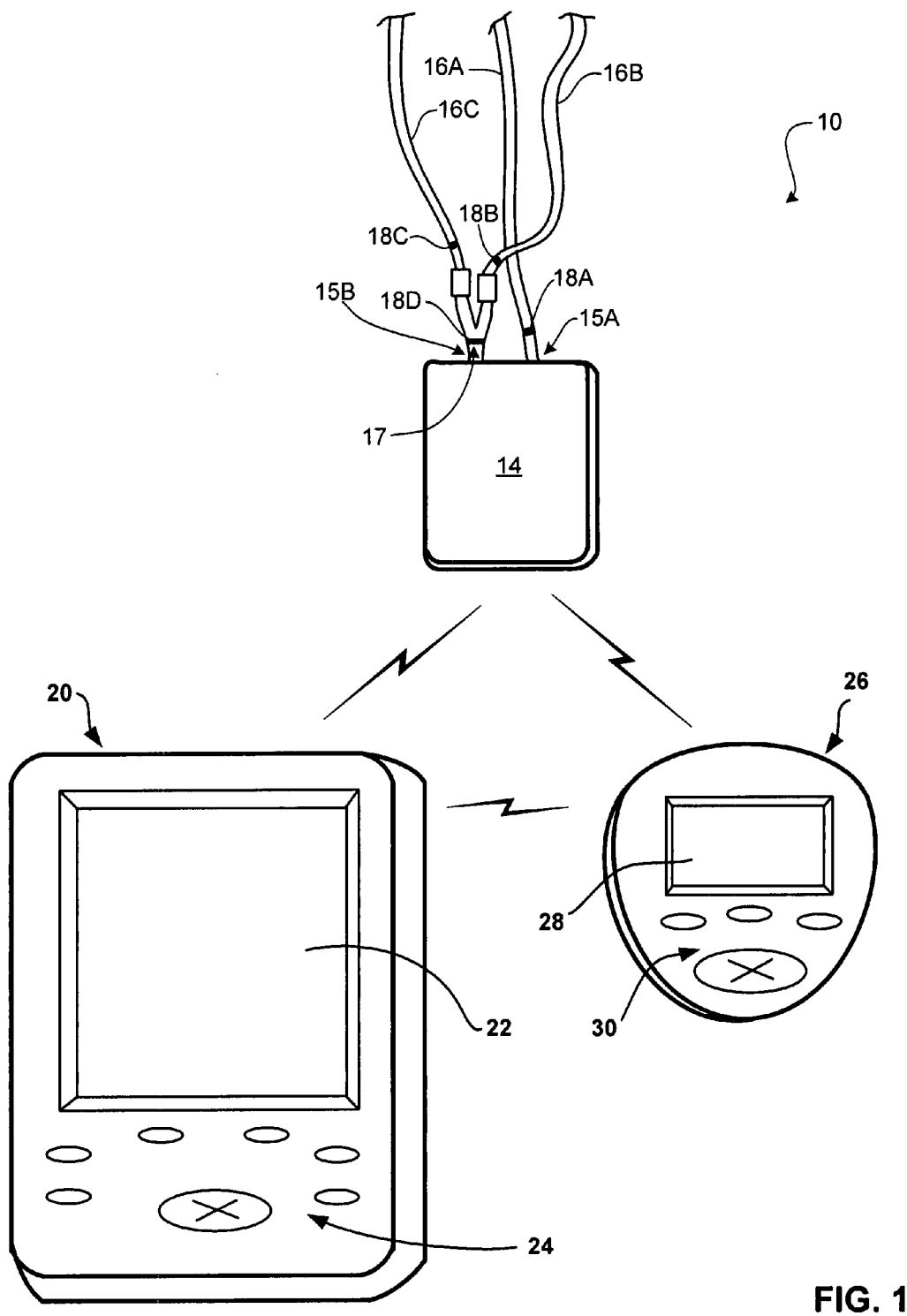
FIG. 1 is a schematic diagram illustrating an example system for programming electrical stimulation therapy for and delivering electrical stimulation therapy to a patient.

The present invention relates to methods and systems for identifying one or more combinations of electrodes for delivering electrical stimulation to a patient. As used herein, "electrode combination" refers to the particular arrangement of anodes and cathodes selected from an array of electrodes. In particular, the electrodes of a combination may be selected from among an array of electrodes implanted within a patient and electrically coupled to a medical device. The array of electrodes may be arranged in one or more columns, where the columns are disposed on one or more medical leads, such as percutaneous leads, implantable lead having a substantially cylindrical lead body or implantable leads having a paddle-shaped portion ("paddle" leads). "Column" is not intended to indicate that the electrodes in the column are aligned along a common axis, although there are embodiments in which the electrodes are aligned along a common axis. Rather, "column" refers to an arrangement in which electrodes are substantially aligned in a longitudinal direction (e.g., along a direction parallel to a longitudinal axis of elongated lead body).

In one embodiment, a class of electrode combinations that is best suited for delivering stimulation therapy to a patient is identified. By identifying a class of electrode combinations that provides efficacious stimulation during a therapy evaluation period, the number of electrode combinations that need to be tested during subsequent to implantation of a stimulation device may be decreased by limiting the tested electrode combinations to combinations from the identified class. Once a class of electrode combinations is identified, one or more specific electrode combinations from within the class may be selected for implementing into a therapy program for the patient. As used herein, reference to an "optimal" electrode combination for a particular patient is not necessarily the most optimal electrode combination that may exist out of all electrode combinations, but rather electrode combinations that provide positive and efficacious therapy for the patient.

In one embodiment, a combination of electrodes is selected by testing a patient response to electrode combinations within two classes of electrode combinations. An array of electrodes that includes at least three columns of electrodes may be used. A first class includes electrodes from one or two columns, while a second class includes electrodes from three columns. Based on the results of the testing within the two classes, a clinician may decide which class of electrode combinations, and possibly which electrode combination, provides the most efficacious therapy to a particular patient relative to the other classes. Delivery of stimulation via the electrode combinations may result in different electrical fields, which may in turn result in different therapeutic results for a particular patient. The selected class may determine the number of leads that are permanently (i.e., not temporarily) implanted in the patient for delivery of electrical stimulation on a chronic basis. The clinician may program an electrical stimulator (e.g., a neurostimulator) to deliver the stimulation therapy to the patient according to an electrode combination within the selected class. The one or more electrode combinations that are programmed into the medical device may be chosen after further testing within the selected class.

The first class of electrode combinations includes electrode combinations utilizing electrodes disposed on one or two columns of electrodes. Combinations within the first class may include, but are not limited to, a bipole combination (i.e., an anode and cathode disposed on a single column of electrodes or two columns of electrodes), a transverse bipole electrode combination (i.e., an anode is displaced substantially transversely relative to a cathode of the electrode combination, which is on an adjacent column of electrodes), and a guarded cathode disposed on one column (e.g., an arrangement of an anode, a cathode, and a second anode along a single column) or two columns (e.g., an arrangement of at least two anodes and a cathode on two columns). The first class includes both guarded and unguarded electrode combinations.

The second class includes electrode combinations utilizing electrodes from each of three columns of electrodes. Within the second class of electrode combinations are transverse electrode combinations and longitudinal electrode combinations. In a transverse electrode combination, two or more anodes of the electrode combination are displaced substantially transversely relative to a cathode of the electrode combination. A stimulation field resulting from delivery of stimulation via a transverse electrode combination is oriented substantially transversely relative to a target tissue for the stimulation. Computer modeling suggests that transverse electrode combinations provide the best selection of recruitment ratios (recruitment of the dorsal column versus dorsal root) compared to combinations from the first class and compared to longitudinal electrode combinations.

Also within the second class are longitudinal electrode combinations, which include combinations in which anodes of the electrode combination are displaced substantially longitudinally relative to a cathode of the electrode combination. A stimulation field resulting from delivery of stimulation via a longitudinal electrode combination is oriented substantially longitudinally relative to a target tissue for the stimulation. Computer modeling suggests that longitudinal electrode combinations provide dorsal column stimulation at the lowest relative voltage compared to combinations from the first class and compared to transverse electrode combinations.

When referring to a lead, the term "longitudinal" indicates a direction of elongation of the lead or lead body, or to the substantially common direction of elongation of a plurality of substantially parallel leads (including, without limitation, leads placed alongside one another in the epidural space). "Lateral," when referring to a lead, indicates a direction generally perpendicular to the longitudinal direction of the lead or substantially parallel leads. When referring to a spinal cord, "longitudinal," "lateral" and "medial" are used in their common medically accepted meanings, e.g., "longitudinal" indicates an axial direction of the spinal cord. The term "transverse," when referring to a lead or electrode array relative to the spinal cord, includes both the lateral direction relative to the spinal cord and diagonal directions relative to the spinal cord, but in either case the term "transverse" implies some crossing over a center line or point defined with respect to the spinal cord or a central lead. All such terms are intended to have approximate practical meanings in view of the flexible structure of exemplary preferred leads and the environment of use, rather than precise geometrical meanings.

In another embodiment, a useful electrode combination for use in delivering electrical stimulation to a patient is identified by testing a patient response to electrode combinations within at least five groups of electrode combinations. Each group may include combinations from within the first class, which includes electrodes from one or two columns of electrodes, and/or from within the second class, which includes electrodes from three columns of electrodes. An array of electrodes that includes at least three columns of electrodes may be used during the testing process. In general, in the descriptions of the five or more groups of electrode combinations provided below, reference to "above" and "below" refer to the location of one electrode with respect to another electrode. When a first electrode is "above" a second electrode, the first electrode has a longitudinal position that is a closer to a distal end of the lead (or furthest from the implanted medical device) than the second electrode. However, if the first and second electrodes are on different leads, the first electrode that is "above" the second electrode is closer to the distal ends of both of the leads, when the leads are implanted in the same substantially parallel orientation.

If the first and second electrodes are on different leads that are not implanted in the same orientation within a patient, one of the distal ends of the leads may be used as a reference point. Thus, the description of electrode combinations below also reference "rostral," which indicates an electrode location that is closer to a distal end of a lead and "caudal," which indicates an electrode location that is further from a distal end of lead relative to another electrode. In some cases, leads may be implanted within a patient such that the distal ends do not face the same direction, or that a distal end of one of the leads faces the feet of the patient rather than the head. Lead may also be implanted in certain regions of a patient such that the distal ends of the leads do not necessarily face the head or feet of a patient, e.g., on a surface of a brain of a patient. Thus, "rostral" in the context of the present description may also mean closer to a distal end of a lead or electrode array, and "caudal" in the context of the present description may also mean closer to a proximal end of a lead or electrode array.

A first group of electrode combinations is characterized by the presence of caudal anodes, in which the anodes of the combination are located below the cathode(s) of the combination. A second group of electrode combinations is characterized by the presence of rostral anodes, in which the anodes of the combination are located above the cathode(s) of the combination. A third group of electrode combinations is characterized by the presence of a single anode above and a single anode below the cathode(s) of the combination, which may be referred to as a "guarded cathode" electrode pattern. A fourth group of electrode combinations is characterized by the presence of multiple anodes above and below the cathode(s) of the combination. A fifth group of electrode combinations is characterized by the presence of transverse anodes, in which at least one anode of the combination is located substantially transverse to a cathode of the combination. A sixth group of electrode combinations is characterized by the presence of one or more off-center cathode. As one example, the sixth group of electrode combinations may include an electrode combination in which a center/middle column of electrodes in an array including at least three column of electrodes, is devoid of any cathodes. As another example, the one or more cathodes of the electrode combination may be along the first and/or third column of electrodes in a three-column array of electrodes.

Based on the results of the testing within the five or more groups, a clinician may identify which group of electrode combinations, and possibly which specific electrode combination, is the most efficacious relative to the other groups or combinations. Delivery of stimulation in accordance with each of the groups may result in different electrical fields, which may in turn result in different therapeutic efficacies for a particular patient. Based on the most efficacious group relative to the other groups, the clinician may further test combinations within the selected group, or may use at least one combination from the selected group as a starting point for identification of additional electrode combinations for testing. For example, one or more electrode combinations from the selected group may be a starting point for initiating another testing methodology to fine-tune the electrode combination (i.e., find an even more efficacious electrode combination, if possible). The resulting electrode combination may or may not be within the group that was selected as the most efficacious among the five or more initially tested groups.

The number of leads that are chronically (e.g., for a time greater than a temporary, trial period) implanted in the patient may be determined based on selected class or the group selected from the five or more groups of electrode combinations. The clinician may program an electrical stimulator (e.g., a neurostimulator) to deliver the stimulation therapy to the patient according to an electrode combination within the selected class or group. However, in some embodiments, the electrode combination that is programmed into the medical device may be selected after further testing within the selected class or group.

In another embodiment, a useful electrode combination to deliver electrical stimulation to a patient is identified by testing a patient response to electrode combinations within at least six groups of electrode combinations, using any of the techniques described herein with respect to the above-discussed five groups of electrode combinations. The six electrode combinations include the five groups mentioned above, and a sixth group characterized by electrode combinations including an off-center cathode. In each of the five groups mentioned above, the one or more cathodes of the electrode combination is disposed along a center column of the three-column electrode array. For example, if three leads are implanted, where each lead includes a column of electrodes, the one or more cathodes in the first five groups of electrode combinations are located on the center lead. In the sixth group of electrode combinations, the one or more cathodes are not on the center column of electrodes, but rather on either or both columns of electrodes next to the center column.

The techniques of the disclosure may also allow a clinician or patient to more quickly and easily identify preferred program groups during a programming session. Initially selecting a group that provides relatively efficacious stimulation therapy from among the five or more groups may minimize the number of possible electrode combinations that need to be tested before finding one or more effective, and in some cases, optimized, programs for a patient because multiple electrode combinations sharing stimulation characteristics may be eliminated as one or more groups of combinations are eliminated. That is, the five or more groups identified herein are categorized together based on many factors, including shared stimulation characteristics or metrics (e.g., computer modeled usage range or dorsal column voltage). The techniques of the invention may also allow the patient to be more readily provided with a greater number and variety of program groups, which the patient may evaluate at home, reducing the amount of time in a clinic setting required to identify preferable program groups for the patient.

FIG. 1 is a diagram illustrating an example system 10 for programming electrical stimulation therapy for and delivering electrical stimulation therapy to a patient. System 10 includes a medical device 14 that delivers stimulation to a patient (not shown). The medical device 14 may be an electrical stimulation generator, and may deliver stimulation to the patient in the form of electrical pulses or substantially continuous-time signals (e.g., sinusoidal signals). Medical device 14 may be implanted subcutaneously in the patient at a location selected by the clinician, or medical device 14 may be worn externally. For example, in some embodiments of the invention, medical device 14 may be a trial electrical stimulator, e.g., an external trial electrical stimulator.

In the illustrated example system 10, medical device 14 may deliver stimulation to the patient via leads 16A, 16B, and 16C (collectively "leads 16"). Leads 16 may be implanted proximate to a spinal cord of a patient, and the medical device 14 may deliver spinal cord stimulation (SCS) to the patient in order to, for example, reduce pain experienced by the patient. SCS may include, but is not limited to, delivery of stimulation via leads implanted epidurally or subdurally. The leads 16 may be substantially fixed in place near the implant site selected by the clinician using a device such as an adjustable anchor, fixation elements coupled to the leads 16 and engage with surrounding tissue (e.g., tines, barbs, hooks, and so forth) or by suturing the leads 16 in place. The leads 16 may be temporary for screening purposes or permanent for long-term therapy.

Although SCS is shown in FIG. 1, system 10 is useful in other electrical stimulation applications. In alternate applications, leads 16 may be positioned proximate to other nerves, organs, muscles, muscle groups or other tissue sites within a patient, which may be selected based on, for example, a therapy program selected for a particular patient. For example, one or more leads 16 may extend from medical device 14 to the brain (not shown) of a patient, and medical device 14 may deliver deep brain stimulation (DBS) to a patient to, for example, treat tremor or epilepsy. Medical device 14 may also deliver electrical stimulation therapy to a sacral nerve, a pudendal nerve, a perineal nerve or other areas of the nervous system, in which cases, leads 16 would be implanted and substantially fixed proximate to the respective nerve. As further examples, electrical stimulation therapy delivered via leads 16 may be useful for treating conditions such as pain, movement disorders, pelvic floor disorders, urinary or fecal incontinence, peripheral neuropathy or post-operative pain mitigation, ilioinguinal nerve stimulation, intercostal nerve stimulation, gastric stimulation for the treatment of gastric mobility disorders and obesity, muscle stimulation (e.g., functional electrical stimulation (FES) of muscles), for mitigation of other peripheral and localized pain (e.g., leg pain or back pain), or for deep brain stimulation to treat movement disorders and other neurological disorders. Accordingly, although SCS is referenced throughout the remainder of the disclosure for purposes of illustration, leads 16 may be adapted for use in a variety of electrical stimulation applications.

The invention is also applicable to subcutaneous stimulation applications. Moreover, the invention is not limited to systems in which a medical device 14 delivers electrical stimulation to the patient. For example, medical device 14 may include sensing electrodes for sensing a patient physiological parameter. As another example, medical device 14 may be configured to deliver another therapy, such as a drug delivery therapy, in addition to electrical stimulation therapy.

The medical device 14 delivers stimulation to the patient according to one or more programs. A program may include values for a number of therapy parameters, and the parameter values define the stimulation delivered according to that program. In embodiments where the medical device 14 delivers stimulation therapy in the form of electrical pulses, the parameters may include pulse voltage or current amplitudes, pulse widths, pulse rates, duty cycles and the like. The pulses may be independently variable (e.g., programmable) so that the voltage or current of each active electrode can be independently controlled. In current controlled embodiments, it is contemplated that each electrode could be an independently controllable current source or independently controllable current sink. An alternative embodiment of a current controlled-type medical device 14 may include one or more electrodes that are programmed to be a voltage reference with other electrodes programmed to be current sources or current sinks. Further, each of the leads 16 includes electrodes (not shown in FIG. 1), and the parameters for a program may include information identifying which electrodes have been selected for delivery of pulses according to the program, and the polarities of the selected electrodes.

A selected subset of the electrodes located on the leads 16 and the polarities of the electrodes of the subset collectively define an "electrode combination," which may also be referred to as an electrode pattern. Electrode combinations refer to combinations of single or multiple cathode electrodes and single or multiple anode electrodes. Stimulation current flows between the cathodes and anodes for delivery of electrical stimulation therapy.

In the embodiment of the medical device 14 shown in FIG. 1, the medical device 14 includes two lead connection ports 15A and 15B. Each lead connection port 15A and 15B is configured to receive connections to eight electrodes, and thus, is able to support a 4-8-4 electrode configuration. That is, the lead 16A including eight electrodes may be coupled to lead connection port 15A and a bifurcated lead extension 17 (also shown in FIG. 2B) including two leads 16B and 16C with four electrodes each may be coupled to the lead connection port 15B of the medical device 14 to form a 4-8-4 electrode configuration (shown in FIG. 3). In alternate embodiments, medical devices including greater or less than two lead connection ports and/or having the ability to receive connections to greater or less than eight electrodes may be employed. For example, in an alternate embodiment, the medical device 14 may be configured to receive and support sixteen electrodes in an arrangement other than a 4-8-4 arrangement (e.g., a 5-6-5 arrangement).

System 10 also includes a clinician programmer 20. The clinician programmer 20 may, as shown in FIG. 1, be a handheld computing device that permits a clinician to program electrical stimulation therapy for the medical device 14. The clinician programmer 20 includes a display 22, such as a LCD or LED display, to display information to a user. The clinician programmer 20 may also include a keypad 24, which may be used by a user to interact with the programmer 20. In some embodiments, the display 22 may be a touch screen display, and a user may interact with the clinician programmer 20 via display 22. In some embodiments, a user may also interact with the clinician programmer 20 using peripheral pointing devices, such as a stylus or mouse. The keypad 24 may take the form of an alphanumeric keypad or a reduced set of keys associated with particular functions. A clinician (not shown) may use the clinician programmer 20 to program electrical stimulation therapy for a patient, e.g., to select electrode combinations and create programs. The clinician programmer 20 supports telemetry (e.g., radio frequency (RF) telemetry) with the medical device 14 to download electrical stimulation parameters to the medical device 14 and, optionally, upload operational or physiological data stored by the medical device 14. In this manner, the clinician may periodically interrogate the medical device 14 to evaluate efficacy and, if necessary, modify the stimulation parameters.

System 10 also includes a patient programmer 26, which also may, as shown in FIG. 1, be a handheld computing device. A patient may use the patient programmer 26 to control the delivery of therapy by the medical device 14. For example, using patient programmer 26, the patient may select a current electrical stimulation therapy program or group of electrical stimulation therapy programs from among the programs or program groups preprogrammed by the clinician, or may adjust one or more stimulation parameters of a therapy program or program group, such as duration, amplitude, pulse width, and pulse rate, within an adjustment range specified by the clinician.

The patient programmer 26 may also include a display 28 and a keypad 30 to allow the patient to interact with patient programmer 26 and the medical device 14. In some embodiments, the display 28 may be a touch screen display, and the patient may interact with patient programmer 26 via display 28. In some embodiments, the patient may also interact with the patient programmer 26 using peripheral pointing devices, such as a stylus, mouse, or the like. The patient may interact with programmer 26 to select programs, including associated electrode combinations, to control the delivery of stimulation by medical device 14. A program may be associated with an identifier, such as an alphanumeric symbol or phrase, which may be displayed via display 28.

The clinician and patient programmers 20, 26 are not limited to the handheld computer embodiments illustrated in FIG. 1. Programmers 20, 26 may be any sort of computing device. For example, in some embodiments, a programmer 20, 26 may a tablet-based computing device, a desktop computing device, or a workstation.

The medical device 14, clinician programmer 20 and patient programmer 26 may, as shown in FIG. 1, communicate via wireless communication. The clinician programmer 20 and patient programmer 26 may, for example, communicate via wireless communication with the medical device 14 using radio frequency (RF) telemetry techniques known in the art. The clinician programmer 20 and patient programmer 26 may communicate with each other using any of a variety of local wireless communication techniques, such as RF communication according to the 802.11 or Bluetooth™ specification sets, infrared communication according to the IrDA standard, or other standard or proprietary telemetry protocols.

The clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, the clinician programmer 20 may communicate with one or both of the medical device 14 and the patient programmer 26 via remote telemetry techniques known in the art, communicating via a network, such as a local area network (LAN), wide area network (WAN), public switched telephone network (PSTN), or cellular telephone network.

In some embodiments, the clinician may use the clinician programmer 20 to create electrical stimulation therapy programs for programming into the medical device 14. As part of the program creation process, a clinician may employ the clinician programmer 20 to controls the medical device 14 to test electrode combinations in order to allow a clinician to identify an effective class of electrode combinations, an effective group of electrode combinations, and/or a particular electrode combination for a patient.

Figure 2A:
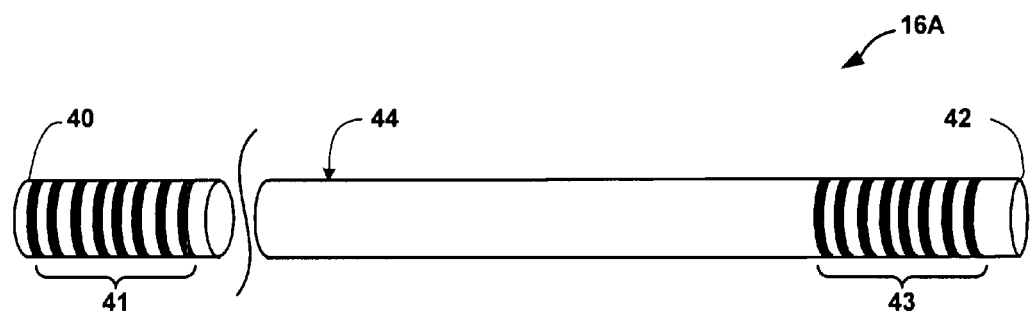
FIG. 2A is a perspective diagram illustrating an implantable medical lead of the system of FIG. 1.

As illustrated in FIG. 2A, exemplary lead 16A, which is representative of each of the leads 16 shown in FIG. 1, has a proximal end 40, a distal end 42, and a lead body 44 extending between the proximal end 40 and distal end 42. Eight connectors 41 (also known as electrical terminals or contacts) are located proximate to proximal end 40 of lead 16A and the distal end 42 has eight stimulation electrodes 43 with various standard pluralities. Connectors 41 have various standard pluralities for electrically coupling electrodes 43 to connection port 15A of the medical device 14. Typically, at least one conductor may be used to establish electrical communication between a single electrical connector 41/electrode 43 pair, although alternative examples include multiplexing or bus features within the lead to allow use of fewer conductors along the length of the lead 16A than the number of electrodes 43, as described in U.S. Pat. Nos. 6,473,653 and 6,038,480. As used herein, "conductive means" or "means for electrical communication between electrodes and electrical connectors" include the foregoing examples or any alternative structure that allows selection or electrical activation of one or more electrode.

In the context of a lead, "distal" means the longitudinal direction along the lead toward the free end of the lead (e.g., typically the end with tissue stimulating electrodes), and "proximal" refers to the longitudinal direction toward the end of the lead that is intended to be connected to a medical device or a lead extension that is intended to connect the lead with a medical device. Because some exemplary leads may be typically somewhat flexible and limp such that the distal and proximal ends of the leads in a mechanical sense could be brought together, it will be understood that proximal and distal refer to relative positions along the length of the lead rather than a coordinate grid in absolute space.

Figure 2B:
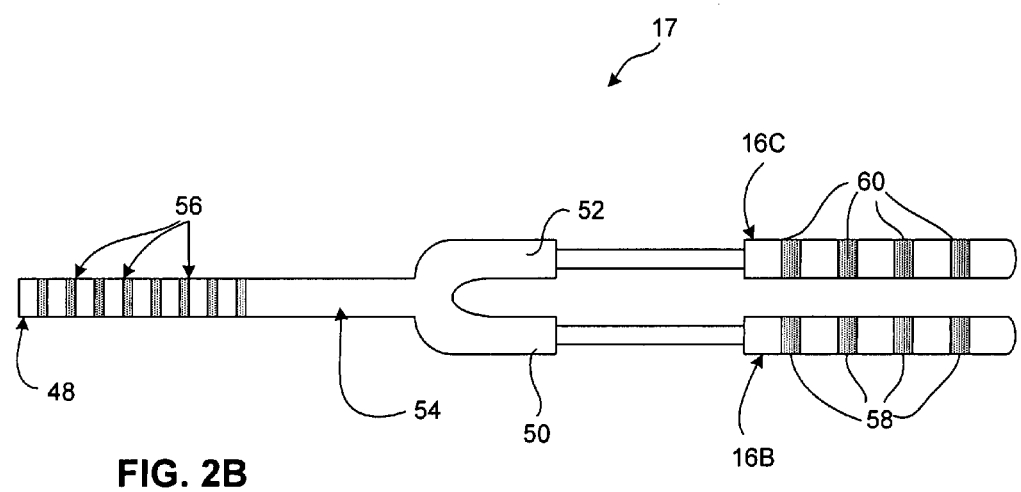
FIG. 2B is a perspective diagram illustrating a bifurcated extension, which may be used to attach two separate leads to a single medical device connection port.

FIG. 2B illustrates a bifurcated extension 17, which is used to form separate leads 16B and 16C of exemplary system 10. The bifurcated extension 17 may be, for example, a Model 37082 stretch-coil bifurcated extension available from Medtronic, Inc., Minneapolis, Minn. The bifurcated extension 17 enables the medical device 14, which includes two connection ports 15A and 15B, to support to three leads in, for example, a 4-8-4 electrode configuration. The bifurcated extension 17 includes a proximal end portion 48, distal end portions 50 and 52, and a lead body 54 extending between the proximal end portion 48 and distal end portions 50 and 52. The proximal end portion 48 has eight connectors 56 (also known as electrical terminals or contacts) for electrically coupling leads 16B and 16C to the medical device 14. For example, the proximal end portion 48 of bifurcated extension 17 may be introduced into the connection port 15B of the medical device 14.

As FIG. 2B illustrates, lead 16B is connected to the distal end portion 50 of bifurcated extension 16 and lead 16C is connected to distal end portion 52. Four stimulation electrodes 58 with various pluralities may be disposed on the lead 50 and four stimulation electrodes 60 with various pluralities may be disposed on the lead 52. In this way, the bifurcated lead extension 17 may be used to effectively connect two leads to a single connection port 15B (FIG. 1) of the medical device 14.

At least one example embodiment of the preferred stimulation leads 16 includes leads that are designed for percutaneous implantation, for example, through one or more needles. Such percutaneous leads typically have a generally cylindrical configuration with ring electrodes (e.g., electrodes 58 and 60) in the distal end portion and ring contacts in the proximal end portion. An alternative exemplary embodiment may involve use of a segmented or partial ring electrodes, each of which extends along an arc less than 360 degrees (e.g., 90-120 degrees) around the circumference of the lead.

Figure 37:
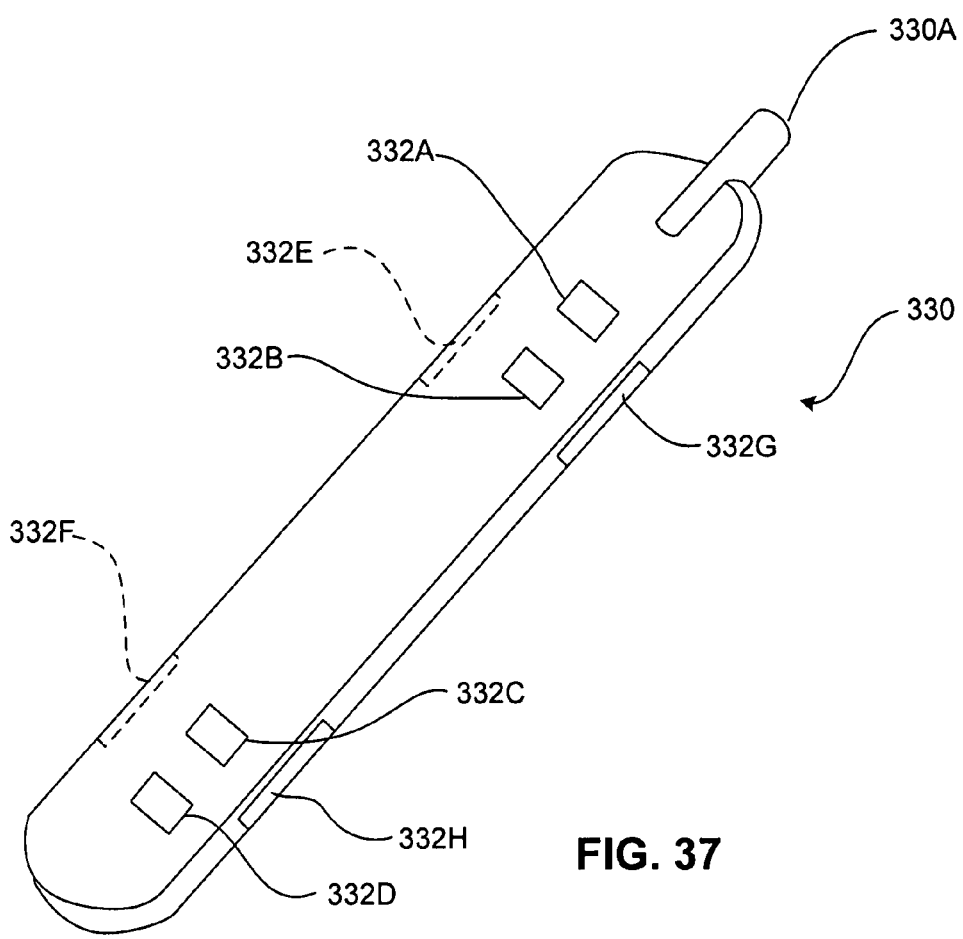
FIG. 37 illustrates an example of a paddle lead.

Furthermore, in some embodiments, a paddle lead is used in a system in accordance with the present invention, where the paddle lead includes one or more longitudinally extending columns of electrodes, where a "longitudinal" direction is substantially parallel to the elongation of the lead body to which the paddle lead is attached. Such a paddle lead may be used as an alternative to multiple leads, each lead having a longitudinally extending column of electrodes. An example of a paddle lead is shown in FIG. 37.

In embodiments in which the lead 116 is a paddle lead (shown in FIG. 19), electrodes may extend along one side of the lead body. Electrodes extending around a portion of the circumference of lead body or along one side of a paddle lead may be useful for providing an electrical stimulation field in a particular direction/targeting a particular therapy delivery site. For example, in a SCS application, the electrodes may be disposed along each of the leads 16 such that the electrodes face toward the spinal cord, or otherwise away from the epidermis of the patient. This may be an efficient use of stimulation because electrical stimulation of the epidermis may provide no useful, or at least very minimally useful, therapy to the patient. In addition, the use of segmented or partial ring electrodes may also reduce the overall power delivered to electrodes by the medical device 14 because of the efficient delivery of stimulation to the spinal cord (or other target stimulation site) by eliminating or minimizing the delivery of stimulation to unwanted or unnecessary regions within the patient.

In embodiments in which the electrodes extend around a portion of the circumference of a cylindrical lead or along one side of a paddle lead, the leads 16A, 16B, and 16C may each include one or more orientation markers 18A-C, respectively, (shown in FIG. 1) proximate to their respective proximal ends to indicate the relative location of the electrodes. The bifurcated extension 17 may include an orientation marker 18D instead of or in addition to markers 18B-C on leads 16B-C. The orientation marker 18 may be a printed marking on the lead, an indentation in the lead, a radiographic marker, or another type of marker that is visible or otherwise detectable (e.g., detectable by a radiographic device) by a clinician. The orientation markers 18 may help a clinician properly orient each lead 16 such that the electrodes carried by the respective lead 16 faces the desired direction (e.g., toward the spinal cord of a patient) within the patient. For example, orientation marker 18 may also extend around the same portion of the circumference of the lead 16 or along the side of the paddle lead as the electrodes. In this way, the orientation marker 18 faces the same direction as the electrodes, thus indicating the orientation of the electrodes to the clinician. When the clinician implants the leads 16 within a patient, the orientation marker 18 may remain visible to the clinician.

In at least one exemplary embodiment of the leads 16, the diameter of the ring electrode is slightly smaller than an outermost perimeter of the lead. This may help avoid direct contact between electrodes on adjacent leads. Alternatives include various structures or means, such as ribs, protuberances, flanges or bumps, which maintain some separation of electrodes on adjacent leads. Any such structure or arrangement constitutes an exemplary embodiment of a means for avoiding direct contact between electrodes on adjacent leads.

Figure 3:
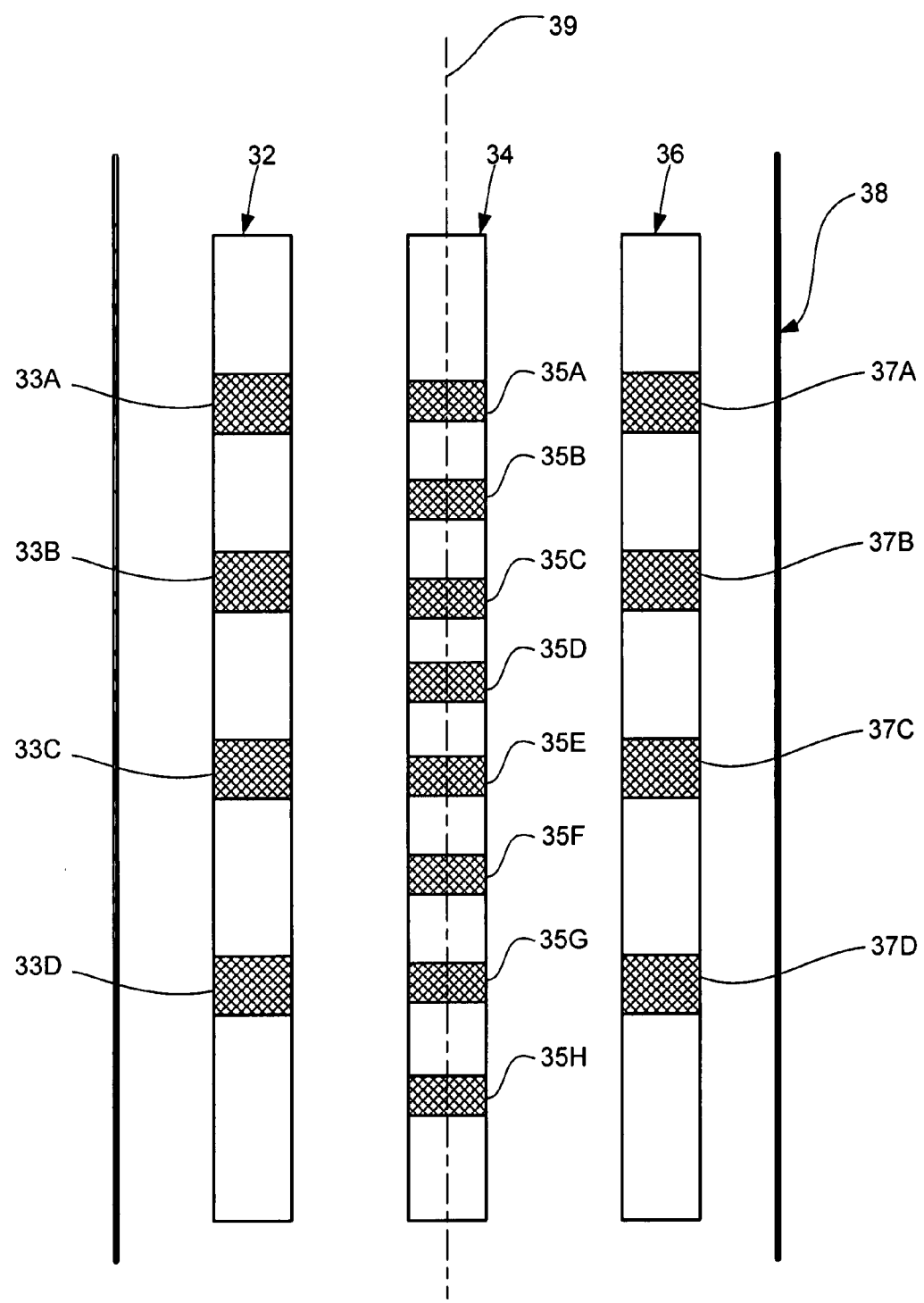
FIG. 3 is a schematic diagram of three columns of electrodes positioned relative to a spinal cord of a patient.

FIG. 3 is a schematic diagram of three columns 32, 34, and 36 of electrodes positioned relative to a spinal cord 38 of a patient. Columns 32, 34, and 36 may, for example, be disposed on three separate implantable leads (e.g., leads 16 of FIG. 1) or on a paddle lead, or a combination thereof. The columns 32, 34, and 36 of electrodes are oriented substantially parallel to the longitudinal midline axis 39 of the spinal cord 38. Further, the electrodes within the columns may also be oriented substantially along and/or parallel to a longitudinal axis of lead bodies that carry the electrodes. Column 34 may be considered a "center" column because of its arrangement relative to adjacent columns 32, 36 of electrodes. Thus, reference to a "center" or "middle" column 34 of electrodes does not refer to a relative arrangement between column 34 and midline axis 39 of spinal cord 38, but to the relative arrangement between adjacent columns 32, 34, and 36 of electrodes.

During the course of finding an efficacious therapy program for a patient, a clinician may adjust the position of the columns 32, 34, and 36 with respect to spinal cord 38. For example, the clinician may adjust one or more of the columns 32, 34, and 36 such that the columns 32, 34, and 36 are no longer centered with respect to the spinal cord 38 (e.g., columns 32, 34, and 36 may all be on one side of the spinal cord 38 midline axis 39). Or the clinician may move one or more of columns 32, 34, and 36 up or down along the longitudinal midline axis 39 of the spinal cord 38.

When implanting columns 32, 34, and 36 of electrodes, a clinician may implant all three columns at once or may "retrofit" an existing therapy system by adding one or two more columns of electrodes, depending upon the desired class of electrode combination to be implemented. For example, if a single column 34 of electrodes has been previously implanted in the patient, a clinician may utilize a bifurcated extension (e.g., bifurcated extension 17 of FIG. 2B) to implant two leads including columns 32 and 36 of electrodes on either side of the single column 34.

Column 32 includes four electrodes 33A-D, while column 34 includes eight electrodes 35A-H and column 36 includes four electrodes 37A-D. Thus, the set of electrodes in columns 32, 34, and 36 are arranged in a 4-8-4 arrangement. In other embodiments, the medical device 14 and/or the electrodes of leads 16 may be configured to support a different arrangement of electrodes, such as a 5-6-5 arrangement or a 2 (rows)×8 (columns) arrangement.

Electrodes 33A-D, 35A-H, and 37A-D are arranged in a column and a plurality of rows. Electrodes 33A-D are each in a different row, while electrodes 35A-H are each in a different row, and electrodes 37A-D are each in a different row. Electrodes 33A-D and electrodes 37A-D may be offset from each or may be aligned with each other (e.g., electrode 33A may be aligned with electrode 37A, electrode 33B may be aligned with electrode 37B, and so forth). Because of the arrangement of the rows of the electrodes 33A-D, 35A-H, and 37A-D with respect to each other, the position of an electrode combination along the length of the column (i.e., the "longitudinal position") may be adjusted. For example, if a simple transverse tripole electrode configuration was implemented, such that electrode 35E is a cathode and electrodes 33C and 37C are anodes, the longitudinal position of the transverse tripole configuration could be adjusted such that electrode 35A is the cathode and electrodes 33A and 37A are anodes.

As previously stated, in methods and systems in accordance with the invention, an electrode combination for a therapy program for a particular patient is selected by first testing from within selective classes or groups within the classes that are generally representative of a broad range of electrical fields that may be achieved through delivery of stimulation via the electrodes of one or more leads. The electrode combination may be selected during a trial period or during period that follows the trial period. The period that follows the trial period may be referred to as a follow-up period, which may be, for example, after an electrical stimulator and leads are implanted in patient. The follow-up period and the trial period may generally be referred to as a "therapy evaluation period." Although trialing periods are primarily referred to throughout the description, the methods and systems described herein are also applicable to follow-up periods or other therapy evaluation periods for a patient. In some cases, a clinician or patient may find that one or more previously selected electrode combinations may need further optimization. For example, the previously selected electrode combinations may no longer provide effective stimulation therapy due to a change in a patient physiological condition.

Techniques for further optimizing a previously selected electrode combination may include testing other combinations within a group or class, finding other combinations via automatic algorithms. The techniques employed for optimizing an electrode combination may or may not be patient directed (e.g., the patient may decide when to start and stop the searching for an effective electrode combination). A programming device may store the results and preferred combinations that result from the optimization.

In a first embodiment, an optimal electrode combination is selected by testing electrode combinations from within the two classes of electrode combinations described above, where electrode combinations represent both the transverse and longitudinal combinations of the second class. In another embodiment, an electrode combination is selected by first testing electrode combinations from within five or more groups of electrode combinations that may, for example, represent a range of electrical stimulation fields achieved by combinations from within the two classes discussed above. Upon finding the most optimal group(s) from among the five or more groups, the clinician or patient may continue to optimize the stimulation therapy by selecting an electrode combination from the most optimal group, and using the selected electrode combination as a starting point for a methodical electrode combination optimization process.

Examples of programming methodologies that may be used following identification of an optimal class or group of electrode combinations include, but are not limited to, those described in commonly-assigned U.S. patent application Ser. No. 11/402,652, entitled, "AUTOGENERATION OF NEUROSTIMULATION THERAPY PROGRAM GROUPS" and filed on Apr. 12, 2006, and commonly-assigned U.S. patent application Ser. No. 11/402,657, entitled, "RULE-BASED STIMULATION PROGRAM SEARCH" and filed on Apr. 12, 2006, which are each incorporated herein by reference in their entireties.

During the testing process, the trial electrical stimulator may be externally carried by the patient, and leads may be percutaneously implanted in the patient. For example, in one embodiment, three leads are percutaneously implanted in the patient (e.g., leads 16A, 16B, and 16 from FIGS. 2A and 2B above).

Figure 4:
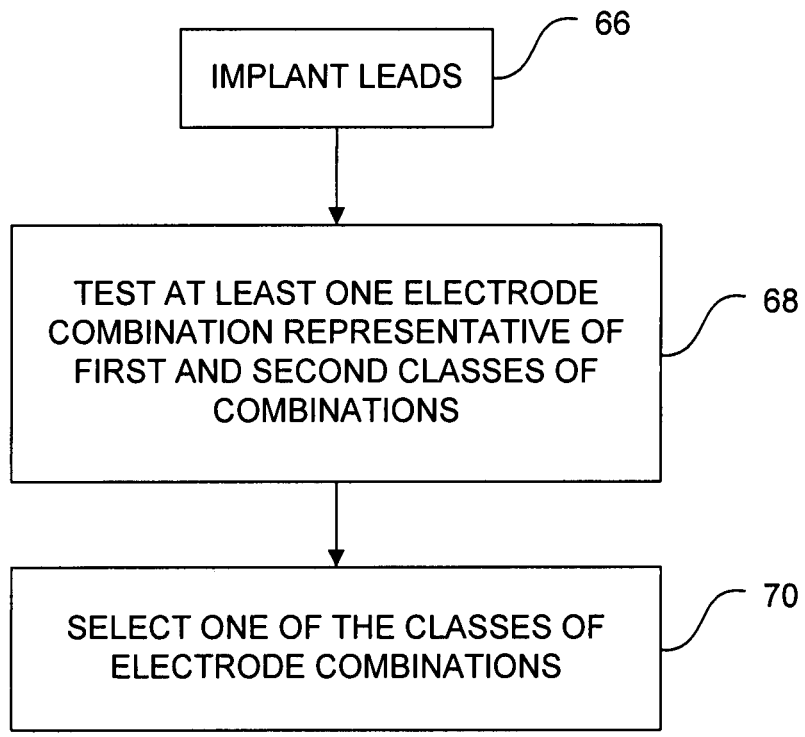
FIG. 4 is a flow chart illustrating one example process for selecting an electrode combination by testing within first and second classes of electrode combinations, where the first class includes combinations of electrodes from one or two columns, and the second class includes combinations of electrodes from three columns.

FIG. 4 is a flow chart illustrating one example method for selecting an electrode combination by testing within the first and second classes of electrode combinations. According to the example method, a clinician implants leads (e.g., leads 16 shown in FIGS. 1 and 2A-B) in a patient (66). The leads may be percutaneously implanted or surgically implanted. Percutaneous implantation of a lead, however, is typically less invasive than a surgical implantation procedure. The leads are electrically coupled to an electrical stimulator, such as the medical device 14 of FIG. 1. Next, at least one electrode combination representative of each of the two classes is tested, which may include testing at least one transverse and one longitudinal electrode combination (68). For example, the programmer and/or medical device can implement each of the electrode combinations for a duration of time, and the patient response can be tested. The patient response may, for example, indicate the area of paresthesia coverage, efficacy of the stimulation therapy delivered by the electrode combination or any side effects resulting from the stimulation. This response may be recorded within the stimulation device, via an external recording device, such as the patient programmer 26 or the clinician programmer 20 (FIG. 1) or by manually writing down notes relating to patient response to the tested electrode combination.

The electrode combinations that are representative of the first and second classes of electrode combinations may be predetermined and stored in a library of combinations that is stored in the medical device or a medical device programmer (e.g., clinician programmer 20 or patient programmer 26 shown in FIG. 1). The patient or clinician may select the programs to cause the programmer and/or medical device to implement the programs by interacting with the clinician programmer 20, the patient programmer 26, or another device configured to communicate with the medical device. Alternatively, the electrode combinations representative of the first and second classes may be automatically delivered to the patient, where each electrode combination is activated for a predetermined amount of time in order to allow substantially all of the effects of the electrode combination to be felt by the patient, such that the patient may provide meaningful feedback relating to the efficacy of the tested electrode combination.

When testing each electrode combination, it may be desirable for the patient to provide feedback on the efficacy of the electrode combination (e.g., side effects or clinical efficacy, or both). In order to identify the feedback with a particular electrode combination, an identifier, such as a graphic identifier (e.g., a number or letter) may be associated with each electrode combination. For example, when a particular electrode combination is being tested, the medical device or medical device programmer may display an identifier associated with the electrode combination so that the patient may record the feedback in reference to the identifier. The feedback may in the form of paresthesia maps, description of the paresthesia locations (e.g., strong and weak), the estimated percentage of coverage with paresthesia, description of comfort or discomfort, the estimated pain relief, side effects, degree of relief, rating, and a description of the activities helped/hindered. The feedback may also include patient activities that were performed and their quality (e.g., sleep, exercise, activities of daily living), McGill questionnaires, and the pain relief duration once, if ever, stimulation is stopped.

Figure 27:
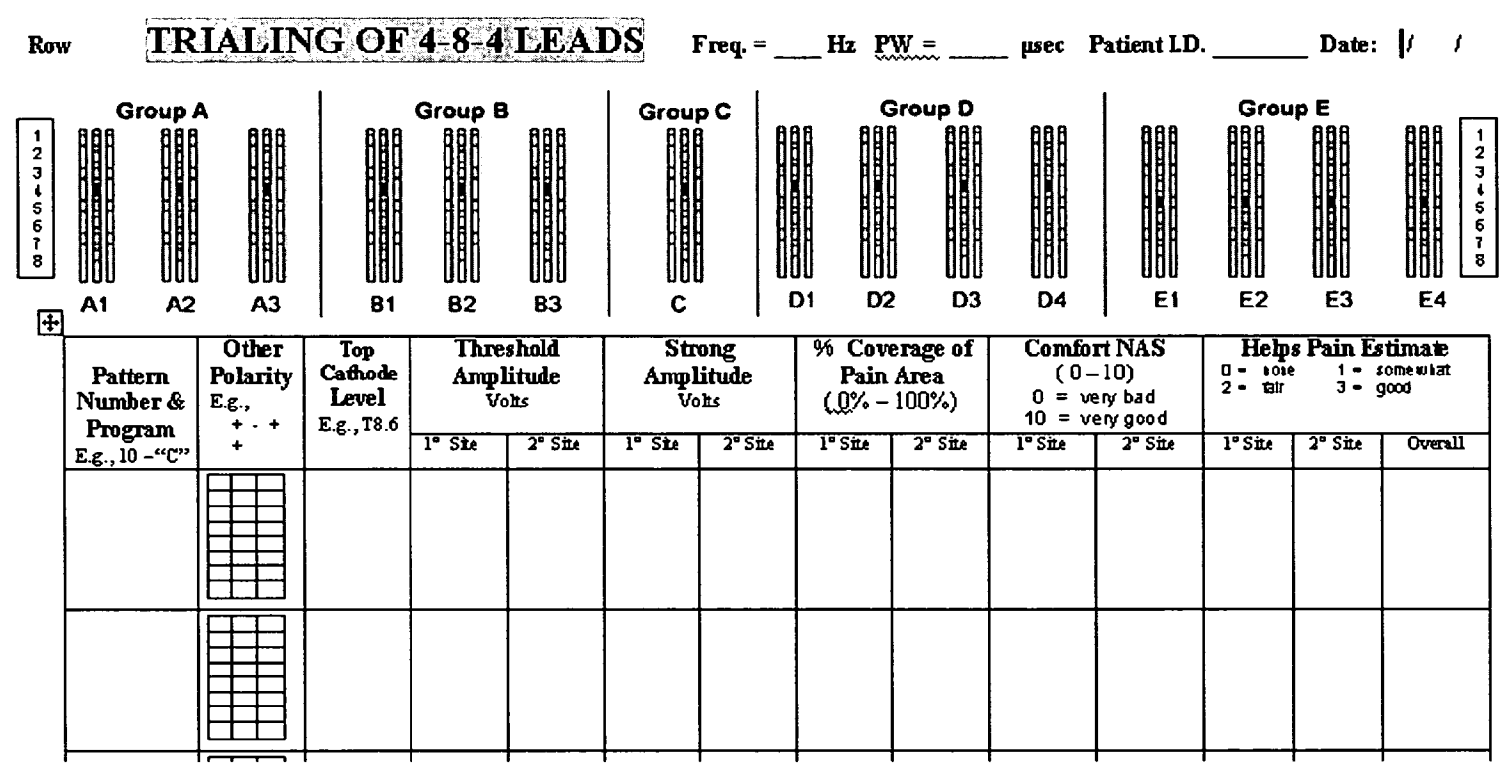

In one embodiment, the patient is provided with a patient data booklet that includes spaces for recording the "program" identifier, where the "program" is the identifier (e.g., the "program A" or "program 1") or the table shown in FIG. 27. The patient data booklet may include spaces for the patient or clinician to manually populate with information such as a program and associated zones of coverage (e.g., by providing a pictorial representation of a body and indicating on the pictorial representation or by identifying numbers associated with different zones of coverage), the duration the program was tested, stimulation current amplitude tested, estimated percentage coverage of pain area with paresthesia, a comfort rating, a pain utility estimate, side effects felt, and an overall rating. In addition, the patient data booklet may include areas for the patient or clinician to manually input feedback relating to the particular stimulation current amplitudes that provided efficacious therapy for a plurality of patient postures, such as sitting, lying down, standing, and walking. Other examples of data the patient data booklet may include are threshold current amplitudes determined by the each tested electrode combination. The patient data booklet may also include instructions for testing each "program."

In addition, the patient data booklet may be adapted to receive patient feedback for "best programs" selected from among a set of preliminary set of electrode combinations. The "best programs" identification technique is described in further detail below.

In other embodiments, the patient data booklet may be provided in electronic form, which is presented on a medical device programming, a personal digital assistant or another computing device. Alternatively, the patient data booklet may be presented via a remote user interface that is coupled to a client server. For example, the patient data booklet may be presented via a web page that the patient accesses from remote location. The patient or clinician may populate the electronic patient data booklet via a user interface, such as a keyboard or touch screen display. Through use of the graphical identifiers, the patient and clinician may be blinded as to the electrode combination being tested, as well as the class of the combination being tested at any given time during the trial period. When the trial is complete, the clinician may later associate the patient feedback with a particular electrode combination or class based on the graphical identifiers.

The best class of electrode combinations can be determined based on the results of the testing during the trial, e.g., based on the patient feedback (70). This information may be useful to a clinician in determining, for example, what configuration of leads, e.g., how many leads or columns of electrodes, should be implanted in the patient on a non-temporary, e.g., chronic, basis. For example, in some embodiments, after the trial period, one or more of the leads implanted in step 66 may be removed from the patient. For example, if three leads are implanted within the patient for the trial stage, and the trial testing results demonstrate that combinations from the first class provides the most positive patient feedback (e.g., most pain relief), only one or two leads may need to be implanted in the patient following the trial period. However, in some embodiments, the clinician may leave the trial leads implanted within the patient. If necessary, a position of one or more those leads may be adjusted.

Figure 5A:
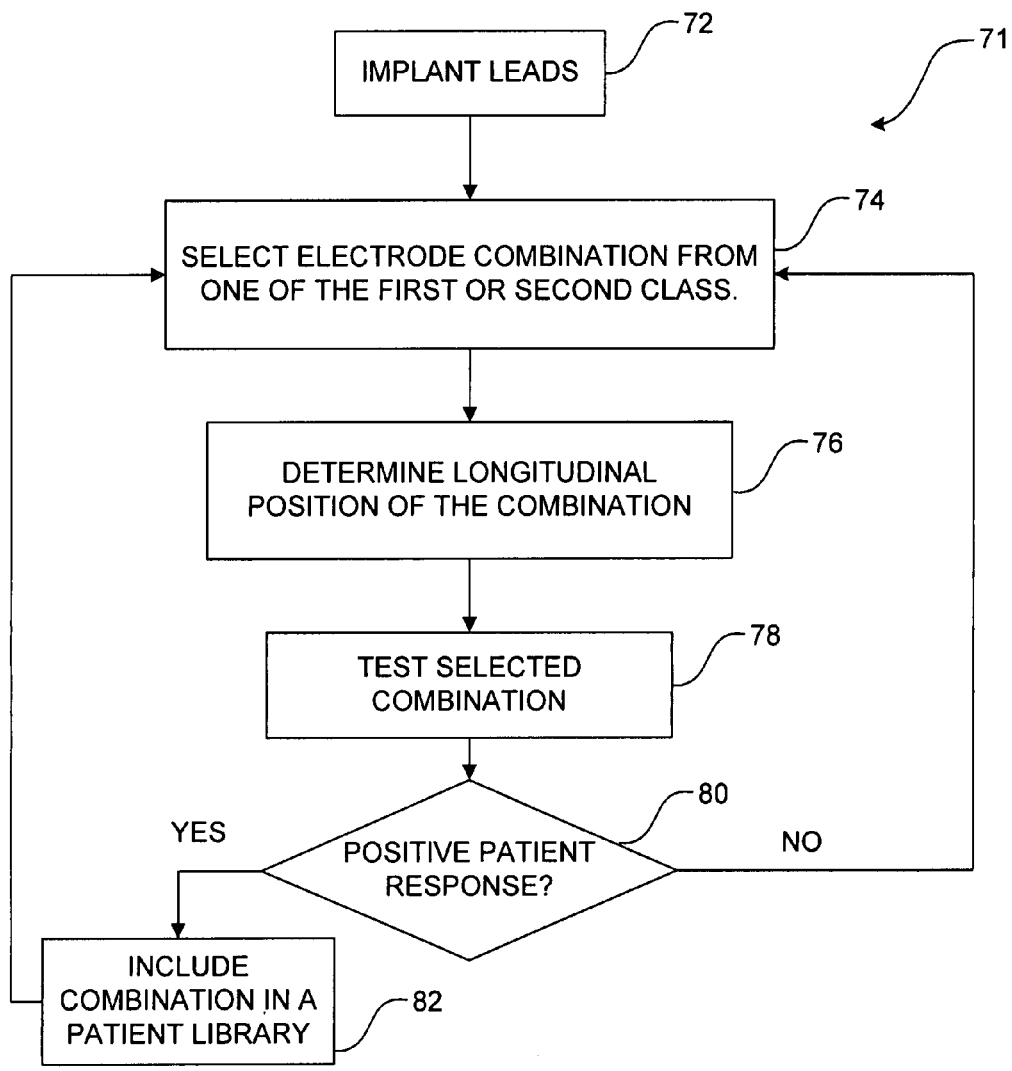
FIG. 5A is flow diagram illustrating another example process for selecting a class of electrode combinations.

FIG. 5A is flow diagram illustrating another example method 71 for selecting a class of electrode combinations.

Similar to the method shown in FIG. 4, leads are implanted in a patient (72). If a paddle lead including three or more columns of electrodes is used, a single paddle lead is implanted in the patient. An electrode combination from one of the first and second classes of combinations is selected, typically by a clinician (74). In one embodiment, the electrode combination is selected from a clinician library, which may include a plurality of electrode combinations in the various classes, and which the clinician may use to test the classes.

A longitudinal position of the selected electrode combination is determined, where the longitudinal position is the row position of the anode and cathode along the longitudinal axis of the lead (76). The longitudinal position may be determined using known methods, such as by selecting a test electrode combination, and "moving" the longitudinal position of the combination, e.g., by selecting similar combinations at different longitudinal positions within an electrode array, until a location best suited for the patient is determined (e.g., based on patient feedback as to the efficacy of the longitudinal position). For example, a methodology (e.g., implemented via a computer-readable medium) that steers stimulation along or between leads 200, 202, 204 to help find the optimal row for the combination, such as TargetStim™ available from Medtronic, Inc. of Minneapolis, Minn., may be incorporated into a programming device. Either the clinician programmer 20 (FIG. 1) or the patient programmer 26 (FIG. 1) may include a user interface that enables the clinician or patient to interact with the computer program, such as by up/down buttons, in order to steer the stimulation between the rows of electrodes on leads 16.

After a suitable longitudinal position is determined, clinician may test the electrode combination by instructing a medical device to implement the electrode combination on the leads for a relatively short duration (e.g., a few minutes) (78). This testing may involve increasing the voltage or current amplitude of the stimulation delivered via the combination, and identifying one or more effects, such as amplitude for paresthesia (the sensation of stimulation), amplitude for strong but comfortable stimulation, or the amplitude for intolerable stimulation. The clinician then determines whether the electrode combination is useful for providing therapy to the patient based on the patient response (80). If the patient provides positive feedback to the electrode combination (e.g., the tissue stimulation provides pain relief, provides an adequate therapeutic range between noticeable stimulation levels, and does not require high amplitudes for efficacy), the clinician may include the electrode combination in a patient library (82).

A clinician library typically includes combinations available to a clinician, whereas a patient library typically includes combinations available to a patient. Both a clinician and patient library may include electrode combinations specific to a patient. However, in some embodiments, the patient library may include initially tested electrode combinations that yield positive results for the patient, whereas the clinician library includes combinations that have not yet been tested. In other embodiments, the clinician library may include a set of electrode combinations that are tested on more than one patient, while the patient library includes electrode combinations specifically selected for a particular patient. In yet other embodiments, both the clinician library and the patient library may include electrode combinations that have been initially tested on a specific patient and that yield positive results for that patient.

The clinician library and/or patient library may be configurable for a particular clinician or for use with more than one clinician. For example, the clinician library may comprise multiple libraries, or different sequencing of a given library, for different patients, different pain locations, lead placements, patient symptoms, and so forth. In some cases, it may be found that certain electrode combinations work better in certain situations, and the sequence of the electrode combinations may be reorganized accordingly to present the most relevant combinations first or present the combinations that are expected to provide the best results first.

If desired, the clinician may repeat steps 74, 76, 78, and 80 to add more electrode combinations to the patient library. It is preferred that the clinician select at least one electrode combination from each of the two classes to test, and more preferable that the clinician also include at least one transverse combination and at least one longitudinal combination, e.g., combinations within the transverse and longitudinal subclasses, within the patient library.

If the electrode combination does not result in a positive response from the patient, the clinician may repeat steps 74-80 and select another electrode combination to test. This may be repeated until the clinician finds an electrode combination that yields positive results for the patient, or until the clinician adds a desirable number of electrode combinations to the patient library.

After the steps shown in FIG. 5A have been completed, the patient library includes one or more electrode combinations that have been identified to be potentially useful for the patient. The patient library may include electrode combinations from only one class, or from both classes.

Figure 5B:
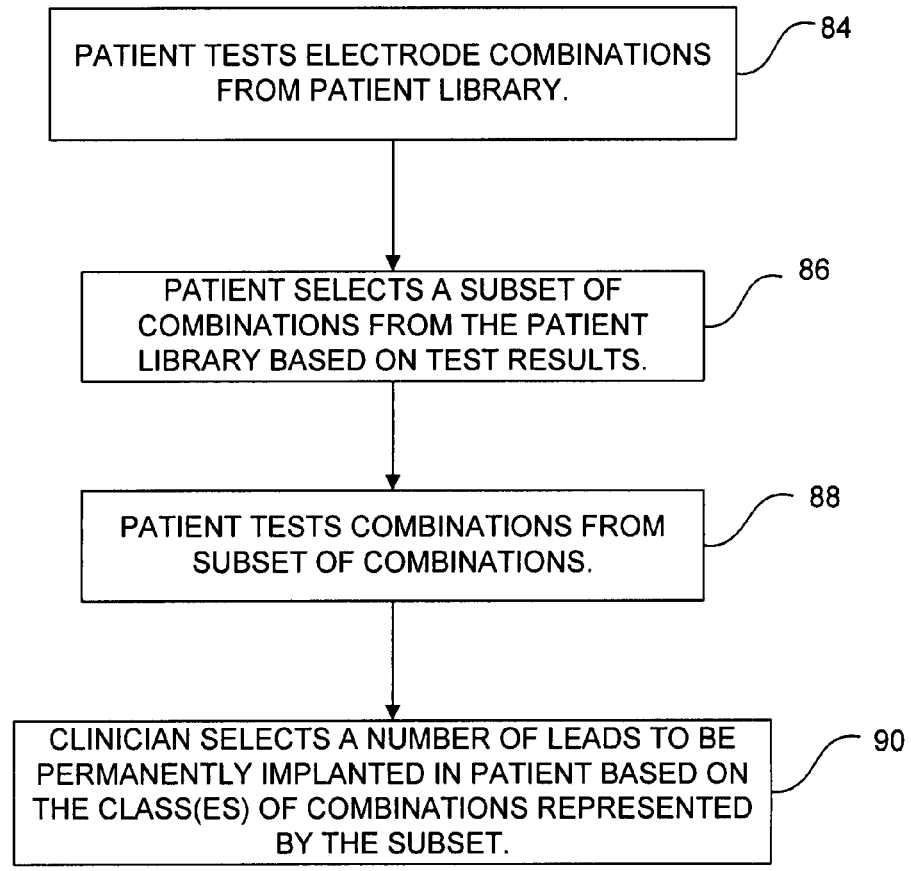
FIG. 5B is a flow diagram further illustrating the process of FIG. 5A, including steps a patient may undertake for identification of a class of electrode combinations.

FIG. 5B is a flow diagram illustrating a technique that may follow after a patient library including electrode combinations is created. The patient may test each of the electrode combinations in the library (84). For example, the patient may test the combinations at home over the course of a set duration of time (e.g., a week). The clinician may load the combinations from the patient library into the patient's external electrical stimulator or a programming device (e.g., patient programmer 26 shown in FIG. 1), and at home, the patient may select the combination to test (e.g., through a user interface on the electrical stimulator or a patient programming device for the electrical stimulator).

While the programmer provided to the patient for testing may include any suitable interface, in some embodiments, the clinician may implement measures to control the patient testing, which may occur outside of the clinic. In some embodiments, the order in which the programs are delivered to the patient for testing is patient directed. For example, the programmer may provide an interface for the patient to select a program from a menu of programs that were loaded into the programmer by the clinician. In this way, the patient may determine the order in which the programs are tested and may select the programs to test. In other embodiments, the patient options may be more limited. For example, the programmer provided to the patient may include up/down arrows (and in some embodiments, only up/down arrows), and the patient may only be able to sequentially scroll through the programs. In this way, the clinician may control the order in which the programs are presented to the patient for testing. As yet another example, the programmer may control the direction or speed of scrolling through the programs by the patient.

In other embodiments, the programmer may control the timing in which the programs are delivered to the patient. For example, the programs may be timed in a particular sequence (e.g., one program per day or per hour). Further, the programmer may be configured to qualify when a program has been sufficiently trialed by the patient. For example, the programmer may determine when a particular program was implemented by the patient's implanted or external stimulator for a certain amount of time, a threshold number of trials, during different times of the day, at least once for a certain number of days, and so forth. The programmer may include a user interface that selectively suggests settings that have not yet been tried or have not been sufficiently. In some embodiments, the programmer may limit the patient to trying only new programs and prevent the patient from trying programs that have been tried, such as by "hiding" the programs that have been tried. The programmer may also include an interface that presents some of the programs multiple times to confirm effects of the respective program.

In some cases, the patient may "blindly" test each combination. That is, the patient may not be aware of the class of electrode combination or specific combination being tested. Furthermore, the clinician may ask the patient to provide feedback from each of the tested electrode combinations, such as by providing the patient with a patient data booklet described above.

When the patient first tests each of the combinations in the library, each combination may be trialed for a relatively short duration of time, such as one-half hour to one hour each. During this phase of the patient testing, the patient may record feedback data relating to the testing of each electrode combination in the library, either through an electronic or non-electronic interface. The patient may further narrow down the combinations in the patient library to a subset of combinations that yield the best results (88). The subset of combinations that yield the best results may be automatically generated by the medical device or a programming device. For example, if the patient provides feedback relating to the trial of each electrode combination in the patient library via the patient programmer 26 (FIG. 1), a processor within the patient programmer 26 may order the patient library according to an "overall ranking" of the electrode combinations provided by the patient. The patient or the processor of the patient programmer 26 may then select a certain quantity of combinations that had the highest overall rankings. The overall ranking may take into consideration many different aspects of the patient feedback, such as an estimated percentage coverage of pain area with paresthesia, a comfort rating, a pain utility estimate, and/or side effects felt.

When the patient tests combinations from the subset of combinations generated from the patient library (88), the patient may test each of the combinations in the subset for a longer duration of time (e.g., one to three days), and record the results of the testing. Based on this testing, the patient may further narrow the number of combinations in the subset. The patient may return to the clinic with the results of the at-home testing.

The patient or clinician may also use programming methodologies (also referred to as optimization methodologies) to further optimize the anode and cathode patterns for each of the electrode combinations in the subset. The programming methodologies may be provided on patient programmer 26 (FIG. 1) or another programming device that provides a user interface. Any programming methodology that generates stimulation programs to assist a user, e.g., a clinician or patient, in searching for preferred stimulation programs may be used. In some embodiments, the programming methodologies may be rule-based, while in other embodiments, the programming methodologies may use an algorithm or a decision-tree type analysis to arrive at one or more electrode combinations for testing based on the starting combination found by identifying a useful class or group of combinations in accordance with the present disclosure.

For example, in one embodiment, the clinician or patient may implement the system and method described in U.S. patent application Ser. No. 11/402,657, entitled, "RULE-BASED STIMULATION PROGRAM SEARCH" and filed on Apr. 12, 2006, previously incorporated by reference. In U.S. patent application Ser. No. 11/402,657, one or more rules are applied to a "parent" program to generate a plurality of different "child" programs. The parent program may be a member program from one of the classes of electrode combinations previously described or one of the groups of electrode combinations previously described. Each child program may be a variation of the parent based on a modification of the electrode combination of the parent according to one of the rules. The child programs may be provided to a user, so that the user may test the efficacy of the child programs, assisting the user in identifying desirable programs. The child programs may be relatively minor variations of the parent program, e.g., adding a third anode, and the user may "fine tune" a generally desirable parent program by testing the child programs.

Each of the rules may define a respective electrode combination modification based on, as examples, the proximity of active electrodes to each other, the proximity of inactive electrodes to active electrodes, or the number of active electrodes. The rules may include, for example, adding an active electrode, removing or adding an active electrode, or changing the location of an active electrode. Some embodiments may apply one or more rules to one or more of the child programs to generate second generation child programs, to one or more of the second generation child programs to generate third generation child programs, and so on. Other programming methodologies may also be used to optimize an amplitude of the stimulation provided to the electrodes of the electrode combinations.

In another embodiment, a programming methodology described in commonly-assigned U.S. patent application Ser. No. 11/402,652, entitled, "AUTOGENERATION OF NEUROSTIMULATION THERAPY PROGRAM GROUPS" and filed on Apr. 12, 2006, which was previously incorporated by reference, may be used. For example, the programming methodology may include receiving rating information and information describing actual therapy effects for a plurality of tested programs, and receiving target therapy data describing target therapy effects. The techniques may include automatically generating a plurality of program groups based on target therapy effects or automatically generating plurality of program groups based on the rating information and a comparison of actual effects to the target therapy effects. Actual effects and target therapy effects may be, for example, actual perceived paresthesia areas and target paresthesia areas or predefined pain areas.

Examples of available programming methodologies include TargetStim™, Optimizer™, and AutoFill™, which are features available in neurostimulation systems from Medtronic, Inc. of Minneapolis, Minn.

A clinician may determine the class of electrode combinations that provided the best results for the patient based on this subset of combinations, which may affect the number of leads to be permanently (i.e., not temporarily) implanted in the patient (90). For example, if it is determined that a single column electrode combination from the first class provides the best results, the clinician implant a single electrode. On the other hand, if it is determined that a transverse tripole electrode combination from the first class of electrodes provides the best results, the clinician may need to implant three leads.

Figure 6:
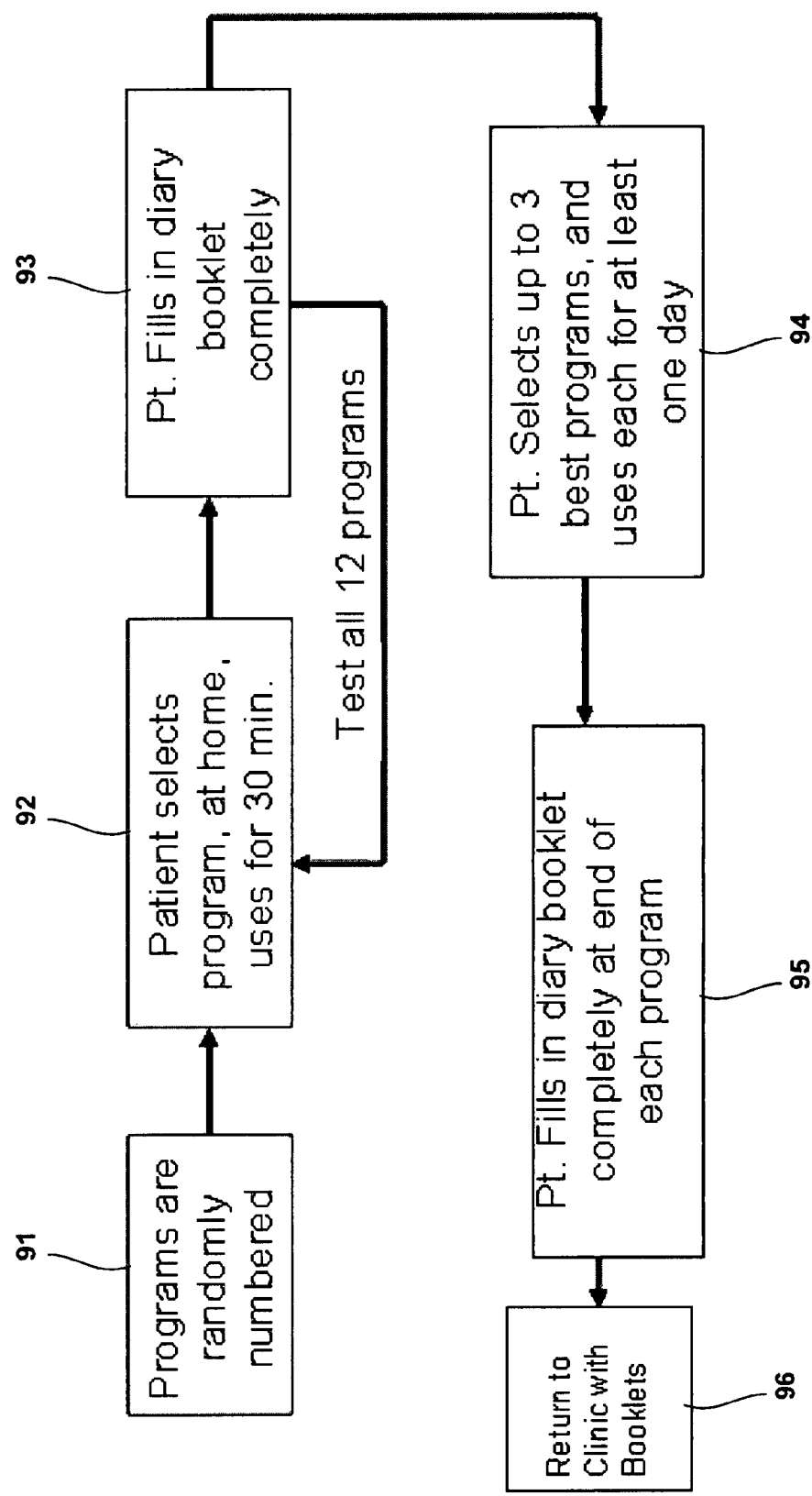
FIG. 6 is another flow diagram illustrating another example process for selecting a class of electrode combinations.

FIG. 6 is yet another flow diagram illustrating another exemplary process for selecting a class of electrode combinations that yields the best results for a patient. In FIG. 6, a plurality of therapy programs each including a different electrode combination are randomly numbered (91). The plurality of programs may include twelve programs that include electrode combinations representative of each of the two classes. The twelve programs may be, for example, the twelve programs shown in FIG. 10. The randomly numbered programs are programmed into the electrical stimulator or a programming device. The patient selects each program at home, and implements therapy delivery via the selected program for about 30 minutes (92). In other embodiments, other durations of time may be used to test each program. The patient may provide feedback for each tested program by filling in a patient data booklet (or a "diary booklet"), as described above, either via an electronic or nonelectronic interface (93).

Based on a first series of testing (92), the patient may select up to three "best" programs that provided the most effective therapy as compared to the other tested programs (94). The patient may provide feedback via a patient data booklet relating to the testing of the "best" programs (95). After testing each therapy program and the best programs within the tested set, the patient may return to the clinic with the feedback (96). In alternate embodiments, the number of programs tested, the duration of the testing, and the number of the "best" selected programs may differ.

Figure 7A:
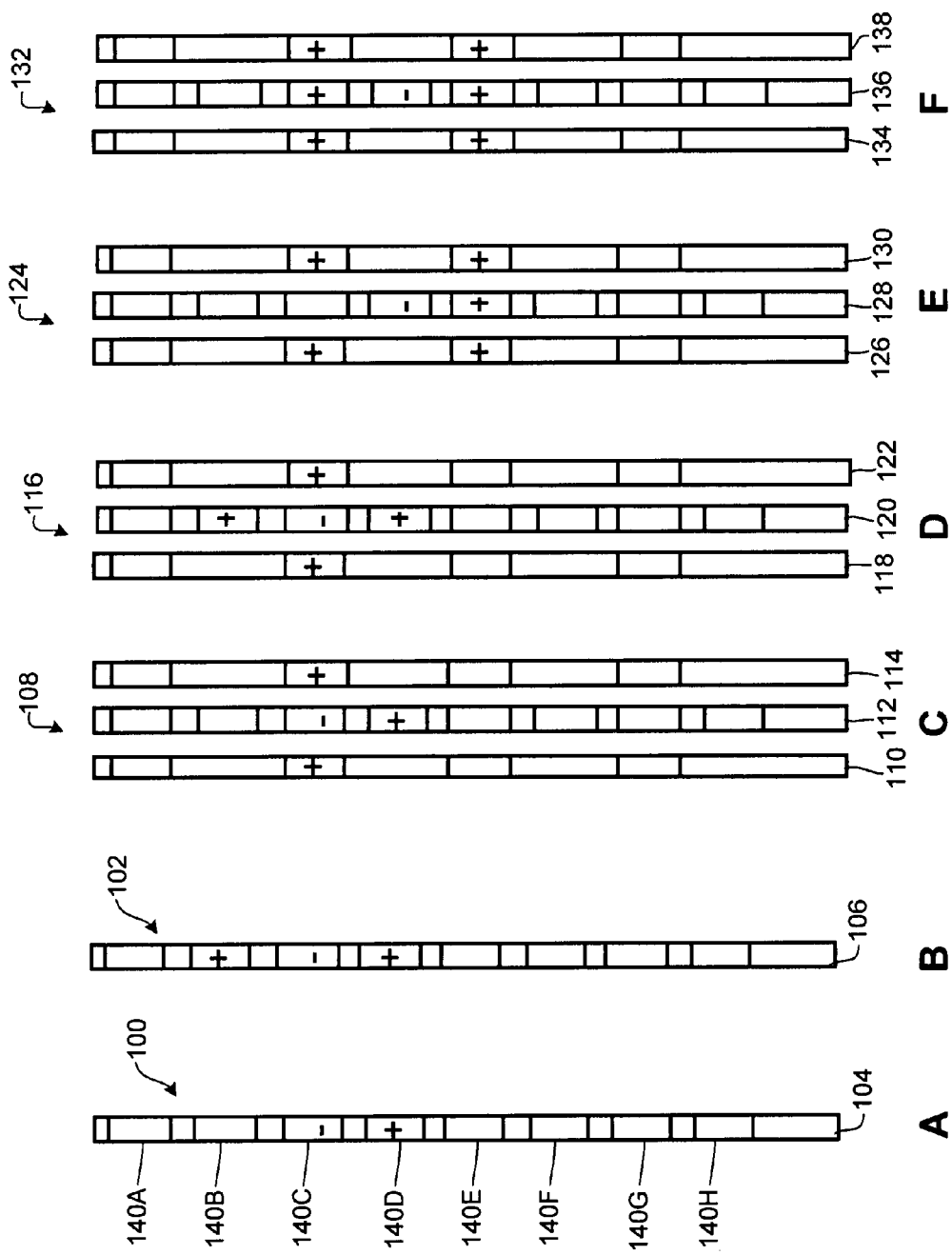
FIG. 7A illustrates schematic diagrams representative of various electrode combinations within the two classes.

FIG. 7A illustrates schematic diagrams representative of various electrode combinations within each of the two classes. The electrode combinations shown in FIG. 7A may make up one possible library of electrode combinations that may be tested during step 68 in the method of FIG. 4. FIG. 7A illustrates electrode combinations 100 and 102 on leads 104 and 106, respectively, that each include eight electrodes, where the combinations 100 and 102 are representative of the first class of electrode combinations. FIG. 7A also illustrates a first exemplary transverse electrode combination 108 on three leads 110, 112, and 114, a second exemplary transverse electrode combination 116 on leads 118, 120, and 122, where the combinations 108 and 116 are representative of the transverse class of electrode combinations. Also shown in FIG. 7A are a first exemplary longitudinal combination 124 on leads 126, 128, and 130, and a second exemplary longitudinal combination 132, on leads 134, 136, and 138. Electrode combinations 124 and 132 are representative of the longitudinal electrode combinations of the second class.

In FIG. 7A, a positive sign (+) indicates an anode while a negative sign (−) indicates a cathode. Furthermore, only the distal ends of each of the leads 104, 106, 110, 112, 114, 118, 120, 122, 126, 128, 130, 134, 136, and 138 are shown.

Leads 104 and 106 each include eight electrodes. For example, lead 104 includes electrodes 140A-140H. The first exemplary electrode combination 100 from the first class is a single lead bipole, where an anode and cathode are disposed on a single lead. The anode is electrode 140D while the cathode is electrode 140C. Of course, the longitudinal position of the anode and cathode may be changed in all the electrode combinations shown in FIG. 7A, where the longitudinal position is the position of the anode and cathode along the longitudinal direction of the lead 104. For example, the longitudinal position of the electrode combination 100 may be adjusted by providing current to electrodes 140B and 140C such that electrode 140B is the cathode and electrode 140C is the anode.

Figure 7B:
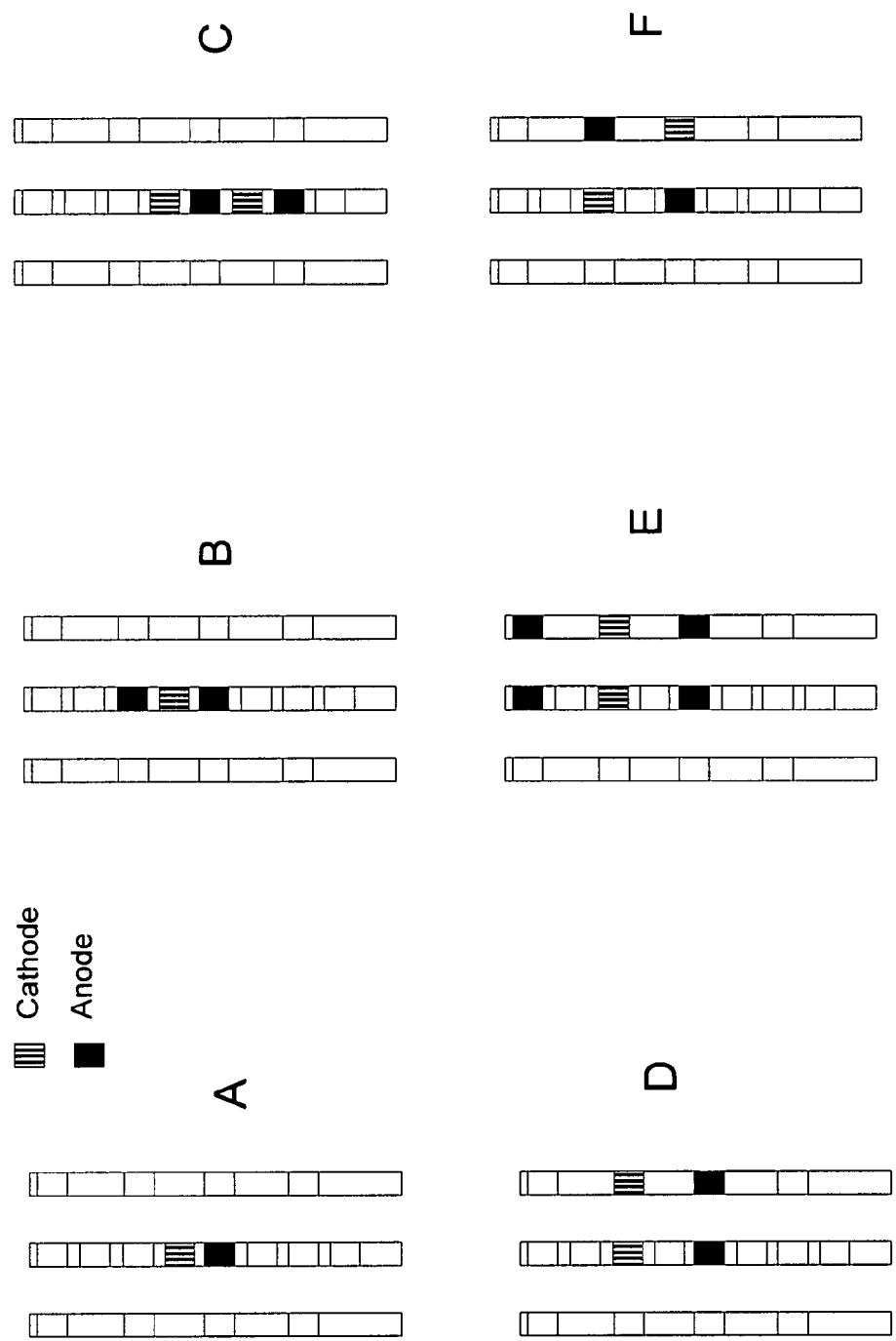
FIG. 7B illustrates schematic diagrams representative of various electrode combinations within the first class.

The second exemplary electrode combination 102 from the first class is a guarded cathode arrangement, where a cathode is centrally disposed between two anodes on a single lead. Other configurations of electrode combinations within the first class (i.e., utilizing one or two columns of electrodes) are contemplated. For example, electrode combinations formed by electrodes disposed on two leads may also be a part of the first class. FIG. 7B illustrates other examples of electrode combinations within the first class, including electrodes disposed on two leads.

Returning now to FIG. 7A, as previously discussed, the second class of electrode combinations includes combinations in which electrodes are disposed on at least three columns of electrodes. Within the second class are transverse and longitudinal combinations. In a transverse combination, at least three electrodes are arranged with a substantial transverse component relative to the tissue being stimulated (e.g., along a line that substantially departs from the longitudinal axis of the spine). The tissue may be any tissue site within a patient, such as neural tissue or muscular tissue. Examples of combinations representative of the transverse class include, but are not limited to, combinations 108 and 116 shown in FIG. 7A. Electrode combination 108 utilizes electrodes disposed on three leads 110, 112, and 114. Leads 110 and 114 are connected to a bifurcated extension, such as the bifurcated extension 17 shown in FIG. 2B. Each lead 110 and 114 includes four electrodes. Lead 112, on the other hand, is a lead such as the lead 16A shown in FIG. 2A, and includes eight electrodes.

In combination 108, a cathode is surrounded by three anodes. In combination 116, a cathode is centrally located between four anodes. These may also be referred to as "guarded cathode" configurations because anodes surrounding the cathode block the cathode field from stimulating dorsal fibers and roots. In contrast, an "unguarded cathode" configuration does not include anodes surrounding the cathode.

FIG. 7A further illustrates exemplary examples of longitudinal electrode combinations from within the second class. As previously discussed, in a longitudinal electrode combination, at least three anodes are arranged with a substantial longitudinal displacement relative to a cathode, and the electrodes of the combination are disposed on at least three columns of electrodes. Examples of longitudinal electrode combinations from the second class include, but are not limited to, the combination 124 and 132 in FIG. 7A. Combination 124 includes a cathode centrally disposed between five anodes, while combination 132 includes a cathode centrally disposed between six anodes. These may also be referred to as guarded cathode configurations because anodes surrounding the cathode block the cathode field from stimulating some of the dorsal fibers and roots.

The six electrode combinations illustrated in FIG. 7A may be included in either a patient or clinician library of electrode combinations that are stored in a medical device programmer or programming device. A clinician may choose to test only the six electrode combinations shown in FIG. 7A in order to select a suitable class of electrode combinations for a particular patient. A patient and/or clinician may systematically test each of the six electrode combinations according to one of the processes described in reference to FIGS. 4, 6, and 7.

Figure 33A:
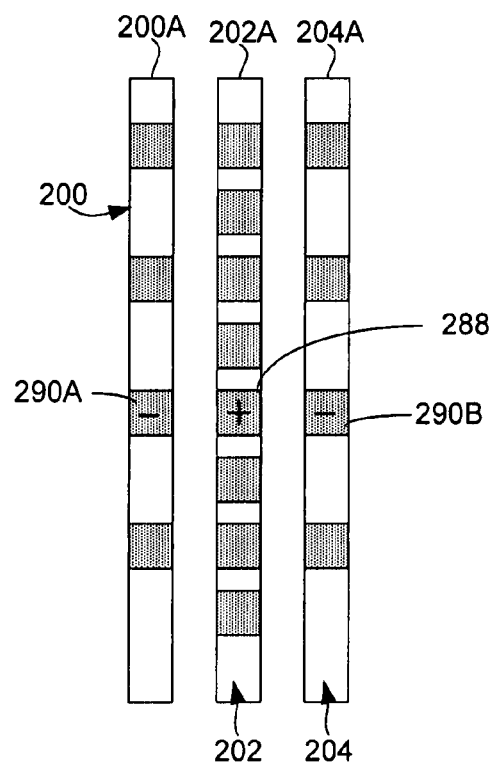
FIGS. 33A-C are schematic diagrams illustrating various representative electrode combinations from a sixth group of electrode combinations.
Figure 33B:
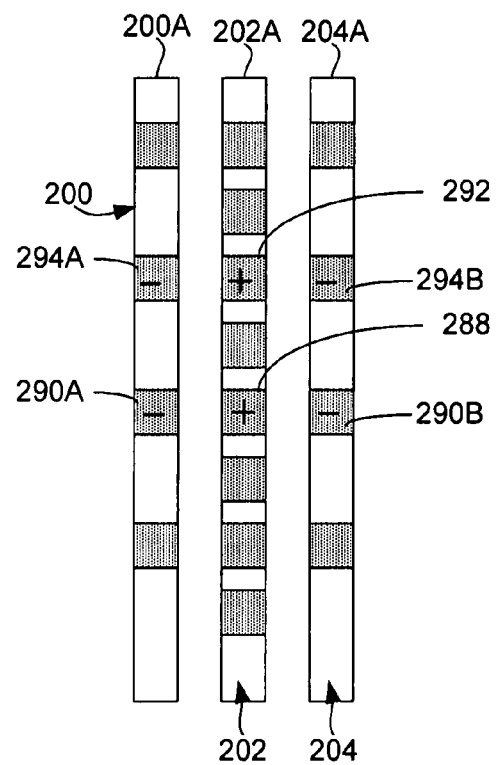
Figure 33C:
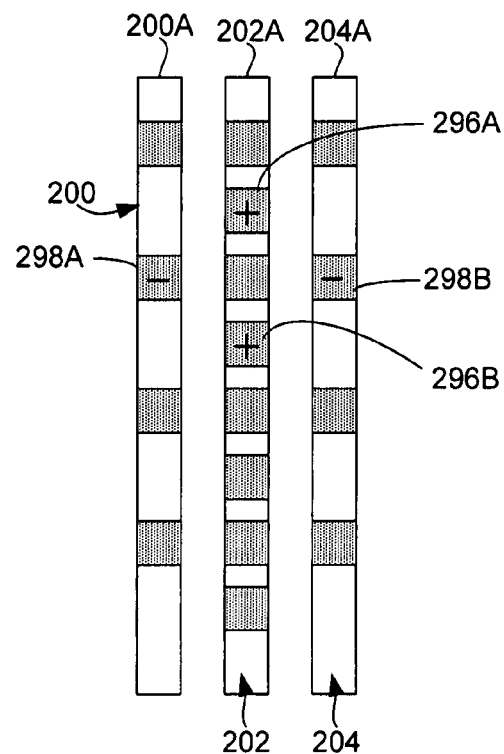

In FIG. 7A, each of the electrode combinations 108, 116, 124, and 132 representative of the second class include a cathode along a center column of electrodes. For example, electrode combination 108 includes cathode (−) along middle lead 112, which is disposed between leads 110 and 114. In other embodiments, a library of electrode combinations that may be tested during step 68 in the method of FIG. 4 may also include combinations representative of the second class that include one or more off-center cathodes. Examples of electrode combinations including off-center cathodes are shown in FIGS. 33A-C.

Figure 8:
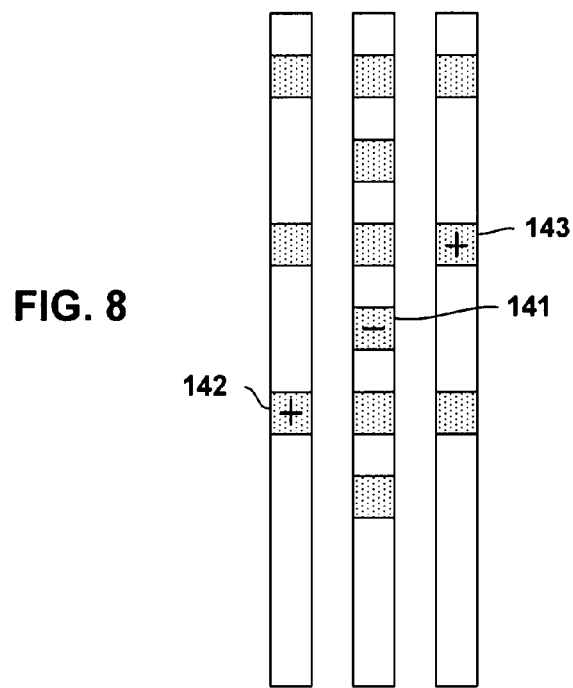
FIG. 8 illustrates an example of a slanted tripole electrode combination.
Figures 9A, 9B:
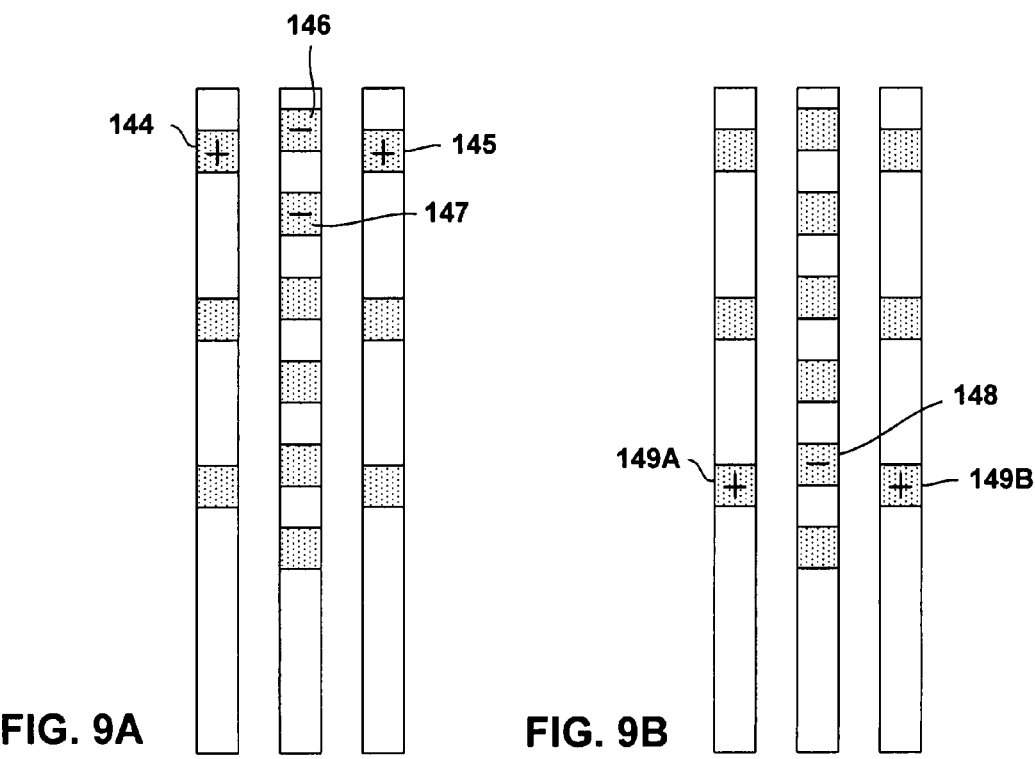
FIG. 9A illustrates a first example of an offset transverse electrode combination.
FIG. 9B illustrates a second example of an offset transverse electrode combination.

FIGS. 8 and 9A-B illustrate further examples of electrode combinations that may be included in a library of combinations to be tested or available to be tested by a clinician and/or patient. FIG. 8 illustrates an example of a slanted tripole, where a cathode 141 is longitudinally located between anodes 142 and 143, which are colinear, but are not exactly longitudinal or transversely aligned. The slanted tripole electrode combination is a hybrid of the longitudinal and transverse electrode combinations.

FIGS. 9A and 9B illustrate examples of offset transverse electrode combinations. In FIGS. 9A and 9B, the columns of electrodes, e.g., leads, are positioned such that electrodes of the array are not substantially aligned along common axes to form rows in the transverse direction. For example, in FIG. 9A, electrodes 144 and 145 are substantially aligned in a transverse direction, but electrodes 146 and 147 are offset from electrodes 144, 145. In FIG. 9A, two cathode electrodes 146, 147 are arranged on a center column of electrodes, while two anodes electrodes 144, 145 are displaced in a transverse direction on adjacent columns of electrodes. The effect of two active cathodes and two anodes in this displaced arrangement results in a substantially pure transverse electrode combination. In FIG. 9B, a cathode 148 and two adjacent anodes 149A, 149B are displaced in a transverse direction.

Both the slanted tripole and offset transverse electrode combinations are within the second class of electrode combinations because each combination includes electrodes disposed in three columns of electrodes.

Figure 10:
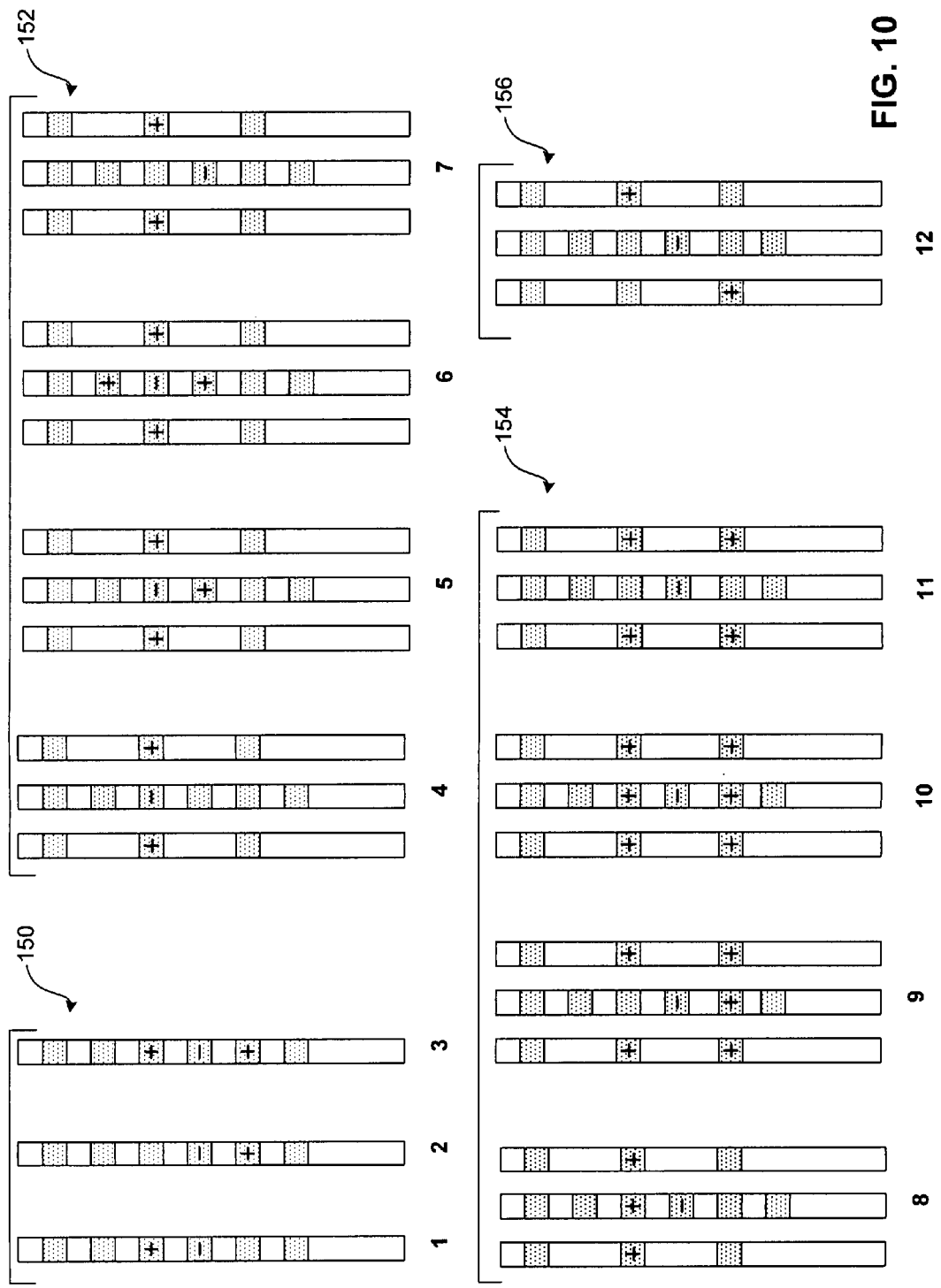
FIG. 10 illustrates a set of twelve electrode combinations that a clinician and/or patient may test, the set including combinations from each of the two classes.

FIG. 10 illustrates a set of twelve electrode combinations that a clinician and/or patient may test. These 12 combinations shown in FIG. 10 may be included, for example, in a clinician or patient library stored within a medical device programmer. Within the set of 12 combinations, group 150 includes combinations from the first class, group 152 includes transverse combinations from the second class, group 154 includes longitudinal combinations from the second class, and group 156 includes a slanted tripole combination, which may be categorized in the second class. Although the electrode combinations are shown on a 3×6×3 electrode array, in other embodiments, the electrode combinations may be achieved with other types of electrode arrays, such as a 4×8×4 electrode array.

Figure 11:
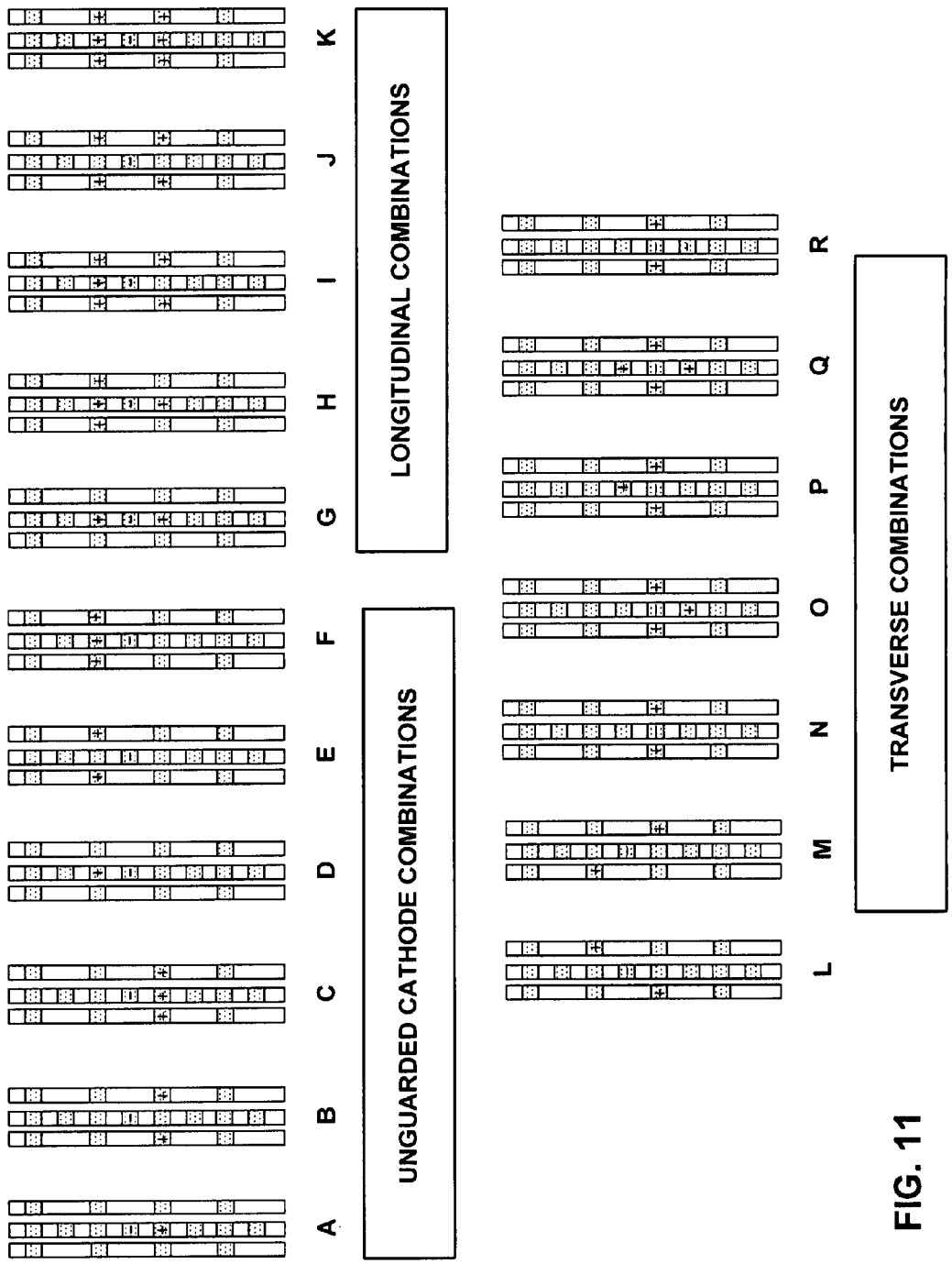
FIG. 11 illustrates schematic diagrams for a set of eighteen electrode combinations from each of the two classes that a clinician and/or patient may test.

FIG. 11 illustrates a larger set of 18 electrode combinations that a clinician and/or patient may test. These 18 combinations shown in FIG. 11 are representative of the first and second classes of combinations and may be included, for example, in a clinician or patient library stored within a medical device programmer. A patient and/or clinician may systematically test each of the 18 electrode combinations shown in FIG. 11 (e.g., according to one of the processes described in reference to FIGS. 4, 6, and 7) in order to find an optimal electrode combination or a set of combinations for programming into an electrical stimulator for permanent for long-term therapy.

Prior to the testing process, a plurality of therapy metrics for each of a plurality of electrode combinations may be generated using computer modeling software that simulates delivery of the stimulation via a particular electrode combination. Therapy metrics generally quantify a result of the delivery of stimulation via the electrode combination. The metrics may reflect an efficacy trend of the electrode combination and/or class of electrode combinations, and may thus be referred to as "efficacy metrics" or "therapy metrics." The results of the modeling may be saved within a database in a memory of a medical device programmer or another computing device. The computer modeling may be performed by a computer modeling system, such as the one available from the University of Twente, which compares the direct effects of electrical stimulation of the spinal cord of various electrode combinations and geometries. The computer model from the University of Twente consists of a volume conductor model of the spinal cord and its surroundings, and an electrical model of the myelinated nerve fibers in the spinal cord. The computer modeling is useful, as an example, in determining the differences between configurations in their activation of dorsal column (DC) versus dorsal root (DR) fibers.

A clinician may compare the efficacy metrics of each electrode combination to select which electrode combinations to include in a patient library of electrode combinations. The metrics may provide, for example, a starting point with which the clinician may be able to discern the relative therapeutic effects or electrical stimulation field characteristics of the electrode combinations relative to each other. The patient library of combinations is typically a subset of available electrode combinations that is available to the clinician, and which the clinician may be interested in testing. Commercially available software may be used to generate metrics for electrode combinations in a given library.

Figure 12:
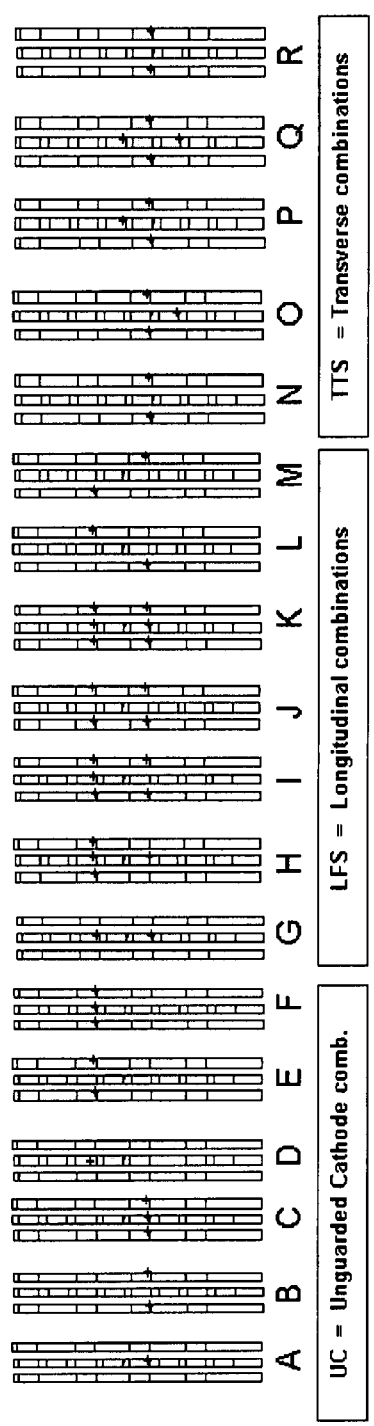
FIG. 12 illustrates a table listing a plurality of metrics for the eighteen electrode combinations shown in FIG. 11.

FIG. 12 illustrates an example of a table that provides the various efficacy metric values for the 18 electrode combination shown in FIG. 11. The table was generated using commercially available software coupled to spinal cord electrical models of the University of Twente. In particular, the efficacy metrics shown in FIG. 12 are:

| | |
|---|---|
| VDC (Volts): | the voltage that stimulates a dorsal column fiber on the midline at the boundary between white matter and cerebral spinal fluid (also referred to as dorsal column voltage). |
| VDR (Volts): | the voltage that stimulates a dorsal root. |
| VDC/VDR: | the ratio of dorsal column fiber threshold to dorsal root fiber threshold. VDC/VDR may also be referred to as the "recruitment ratio." In general, if VDC/VDR is greater than 1, then the dorsal root is recruited preferentially, and if VDC/VDR is less than 1, the dorsal column is recruited preferentially. |
| VMAX (Volts): | the assumed discomfort threshold, or about 1.4 * VDR. |
| UR: | usage ratio is the discomfort threshold divided by the paresthesia threshold |
| IMAX (milliamps): | about 1.4 * VDR divided by the electrode resistance. |
| DMEAN (millimeters): | the mean depth of recruited area from the middle of the dorsal spinal cord. |
| DMAX (millimeters): | the maximum depth within dorsal columns for which dorsal column fibers are recruited at a discomfort threshold (assumed to be 140% of VDR). |
| Area factor (millimeters): | Dmax or Dmean divided by the width at two standard |

| | |
|---|---|
| | deviations from the X (medial-lateral mean). |
| Area max (millimeters squared): | cross-sectional surface area of the recruited zone within the dorsal columns at max. |
| DR span (centimeters): | The distance of dorsal root activation at a maximum amplitude. |

The details of the computer modeling that was performed to arrive at the values in FIG. 12 are provided in below in the description of experiments and results.

Rather than testing all 18 electrode combinations shown in FIG. 12, a clinician may reference a table of efficacy metrics, such as the one shown in FIG. 12, to determine which electrode combinations and/or which classes of electrode combinations to test. For example, if the clinician desires to deliver a stimulation therapy according to an electrode combination that results in a high usage range (UR), the clinician may reference the table shown in FIG. 12 and compare the UR values for the eighteen electrode combinations. The table of FIG. 12 shows that electrode combinations D, G, N, P, and Q result in the highest relative UR values based on a computer modeling system, which is described below in reference to FIG. 15. Based on the UR values, the clinician may choose to test electrode combinations D, G, N, P, and Q, rather than testing all 18 combinations shown in FIG. 12. In an alternate embodiment, the clinician may choose to compare a different efficacy metric value. For example, it may be desirable to stimulate the dorsal column rather than the dorsal roots. Thus, it may be desirable for a clinician to select one or more classes or electrical combinations within the classes based on the VDC/VDR metric value. In another example, where a rechargeable stimulation system is not the most appropriate, and a system with a primary battery is used, an important efficacy metric may be VDC or IMAX, which are related to the stimulation amplitudes. On occasion, metric values may be close when comparing electrode combinations in both classes, hence, the choices for programs need not be limited to a single class based on the results of a trial period.

In other embodiments, the table shown in FIG. 12 may include any number of metrics a clinician may find useful to distinguish between electrode combinations, as well as metrics for any suitable number of electrode combinations. For example, the clinician may store upwards of hundreds to thousands of electrode combinations and associated metrics in a computing device, and reference the combinations and associated metrics when selecting an electrode combination for one or more patients.

Figure 13:
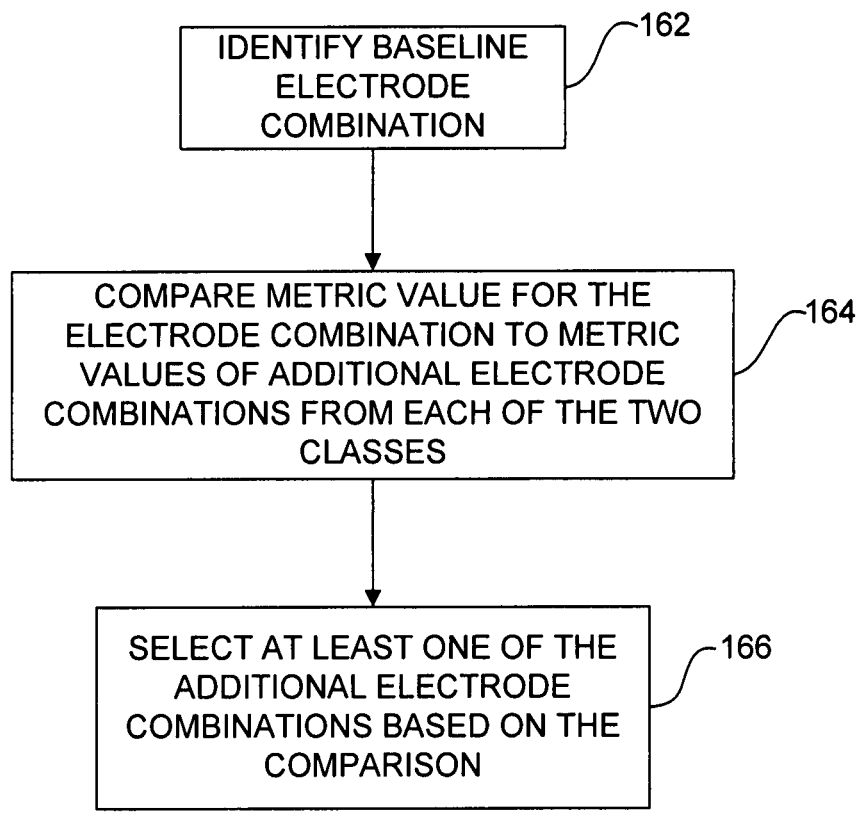
FIG. 13 is a flow diagram illustrating an example process for selecting one or more electrode combinations by comparing metric values for a plurality of combinations.

FIG. 13 illustrates a technique for selecting electrode combinations to test using a table of metric values such as the table shown in FIG. 12. A clinician identifies a baseline electrode combination by receiving feedback from a patient in response to the delivery of stimulation according to the electrode combination (162). The electrode combination may be identified by testing a plurality of electrode combinations and selecting the electrode combination yielding the most positive results. Alternatively, a single electrode combination may be chosen to be used as a baseline combination. Thereafter, the clinician compares a value of at least one metric for the baseline electrode combination to the metric values for a plurality of additional electrode combinations, where the additional electrode combinations are representative of the first and second classes of combinations (164). The metric values may be determined from experimental modeling, such as the computer modeling that was done for the table shown in FIG. 12. The clinician may choose which one or more metric values to focus on when comparing the metric values based on the patient response to the identified electrode combination.

The clinician may select one or more of the additional electrode combinations based on the comparison between the metric value(s) (166). Comparing metric values for a plurality of electrode combinations in the first and second classes may help narrow down the number of combinations that are tested in order to find the best suited electrode combination for the patient's therapy program. The metric may include, but are not limited to, a dorsal column current, usage range, a ratio of dorsal column stimulation threshold voltage to dorsal root stimulation threshold voltage, a recruitment area, an area factor, a maximum output voltage, or a dorsal column stimulation threshold voltage. Other metrics may also be calculated.

The present invention also contemplates a system in which a table of efficacy metrics is provided to a clinician for the purpose of selecting a class of electrodes combinations or set of electrode combinations to test. The information contained in the table may be in any form, and does not necessarily need to be provided in a table. For example, the information might also include graphical displays of the zone of recruited axons in a plane of the spinal cord that is transverse to the axis of the cord. Furthermore, the table may be electronic and include features for user interaction. For example, the system may prompt a user to select one or more efficacy metrics to view, or to input a target value of one or more efficacy metrics.

Alternatively, a computer program may select an optimal electrode combination based on the desired parameters for the metric, which may be entered into a computing system by the clinician or patient. In one embodiment, the computer program may select the optimal electrode combination based on patient testing (e.g., in accordance with the techniques shown in FIGS. 6B and 7). For example, after patient tests multiple electrode combinations at home, the patient may return to the clinic with a selected electrode combination that works relatively well, but results in some negative effect (e.g., the combination results in discomfort or motor effects at a relatively low amplitude setting). A computer program running on a programmer or other computing device, or another type of computerized process, may provide an interface for a clinician or patient to enter a desired parameter for a particular metric, or a particular metric to optimize.

For example, as described below with reference to FIG. 35, the clinician may interact with the user interface and select a metric, such as UR, from a pull-down menu and select an "increase" option/modifier. In one technique, the computer program may initially look within the selected class (or group, in the embodiments discussed below) of combinations resulting from the patient testing to find the best UR possible within the preferred class for the particular patient and direct the medical device to implement the combination for testing. If none of the combinations within the preferred class can satisfy the desired modification, the programmer might look to other classes for a candidate, perhaps with a notification to the user that the search is continuing outside the class indicated by the clinician to be preferred.

In some embodiments, the computing device running the application including the metric values may be able to scale the metrics based on a patient's response to a baseline electrode combination that is tested on the patient. For example, if patient data is taken, and the patient reports lead to a conclusion that the patient reality is 256% higher than the metric predicted, the device could scale all the metrics, so that changes predicted by the model should very closely match what would be found with that patient for all patterns/combinations. Alternatively, the clinician may manually scale the metric values.

Computer modeling that modeled an effect of electrode combinations from the first and second classes was performed. Three computer models are described below. The computer models were useful for comparing the stimulation fields generated by different electrode combinations from each of the two classes, as well as generating metric values for different electrode combinations.

Computer Modeling Example 1

Data relating to a plurality of electrode combinations was obtained using computer modeling of lower thoracic placement of electrodes using a first computer modeling technique. The data was for the electrode combinations that included electrodes within less than three columns (i.e., a combination from the first class), at least one transverse electrode combination, and at least one longitudinal electrode combination (i.e., combinations from the second class). In the first model, a McIntyre-Richardson-Grill myelinated fiber model was used, in which the medial dorsal column fiber is about 12.8 μm (31 nodes) with a 5.7 μm collateral (10 nodes) and the dorsal root fiber is about 15 μm (8 nodes) and attaches to the 12.8 μm (31 nodes) longitudinal fiber in the lateral dorsal column.

Three columns of electrodes were modeled, where the electrodes were arranged in a 4-8-4 arrangement. A low thoracic spinal cord model utilized in the first computer modeling example was built based on a University of Twente model. The model developed by the University of Twente simulates the effect of SCS on three-dimensional volume conductor model of the anatomical and electrical properties of the spinal area, and a model of the electrical behavior of myelinated nerve fibers in the same area. First, the volume conductor model is used to calculate the electrical field produced by anodal and cathodal electrodes at given potentials and specific positions. The electrical field is applied to the nerve fiber model to determine the extent to which dorsal column and dorsal root fibers are stimulated.

The neuron model was based on a McIntyre-Richardson-Grill axon model. The model also included a dorsal fiber pathway similar to University of Twente model, but in the present model, the fiber pathway was slightly extended to include more nodes in the dorsal root fiber. The computer model further utilized a constant pulse width at 210 μs (monophasic square pulse). Thresholds were obtained for a midline dorsal column fiber a branch node centered at the middle of the cathode, and for a lateral dorsal root fiber was moved in a Z-direction (i.e., along the longitudinal axis of the spinal cord) within the dorsal root span until the lowest threshold was obtained. Therefore, the modeled VDR and all calculations using VDR reflect the worse case.

In the first computer modeling example, measures of comparison between the different electrode combinations that were obtained include fiber selectivity (VDC/VDR), dorsal root span, VDC, discomfort threshold (1.4*VDR), usage range, recruited area, depth, width, mean, and standard deviation in an x-direction (medial-lateral) and Y (dorsal-ventral) directions, area factors, and power consumption, which was measured in current. An example table that was generated using the first computer model is shown in FIG. 12.

Figure 14:
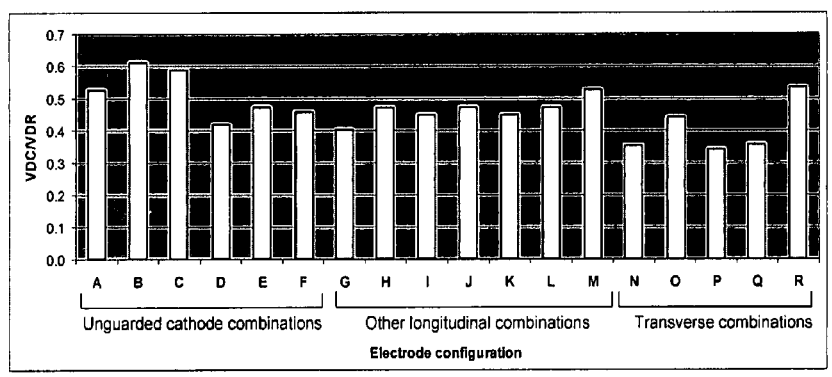
FIG. 14 illustrates a graphical display of therapy metric data generated for a plurality of electrode combinations according to a first example of computer modeling.

The first computer modeling technique may be employed to generate a table of metrics and associated electrode combinations, such as a table similar to the table shown in FIG. 12. In addition to or instead of the table, the first computer modeling technique, or any other computer modeling technique, may be used to generate other graphical displays for presenting the relative value of at least one metric for a plurality of electrode combinations. For example, as shown in FIG. 14, a chart illustrates the relative VDC/VDR (fiber selectivity) values for a plurality of electrode combinations designated A-R. A clinician may review the chart to quickly discern information about the electrode combinations, such as which electrode combination demonstrated the best fiber selectivity based on the computer modeling or how the fiber selectivity for one electrode combination compares to the other electrode combinations that were modeled.

FIG. 15 illustrates example graphical displays generated via the computer model, where the graphical display illustrates the zone of recruited axons (i.e., the recruitment area) in a plane of the spinal cord 167 that is transverse to the axis of the spinal cord for electrode combinations A and B, which may be combinations within the first class or the second class of electrode combinations. Similar graphical displays may be generated for each electrode combination simulated via the computer modeling software. In general, a clinician may review the graphical displays and compare the graphical representation of the recruited axons 168 and 169 in order to compare the recruitment areas for each of electrode combinations A and B.

Computer Modeling Example 2

A second computer modeling technique included calculating the direct effects of electrical stimulation of the spinal cord using various electrode combinations and geometries using a second computer model, the University of Twente Model. The spinal cord stimulation (SCS) computer model basically consists of a volume conductor model of the spinal cord and its surroundings, and an electrical model of the myelinated nerve fibers in the spinal cord.

Descriptions of the SCS computer model and of the methods applied in this report are described in a number of previously published papers, including: *How do geometric factors influence epidural spinal cord stimulation?* J. Holsheimer, J. J. Struijk, Stereotactic and Functional Neurosurgery, vol. 56, pp. 234-249, 1991, *Effects of electrode geometry and combination on nerve fiber selectivity in spinal cord stimulation*, J. Holsheimer, J. J. Struijk, N. Tas, Medical & Biological Engineering & Computing, vol. 33, pp. 676-682, 1995, *Optimum electrode geometry for spinal cord stimulation: the narrow bipole and tripole*, J. Holsheimer, W. A. Wesselink, Medical & Biological Engineering & Computing, vol. 35, pp. 493-497, and *Effect of anode-cathode configuration on paresthesia coverage in spinal cord stimulation*, J. Holsheimer, W. A. Wesselink, Neurosurgery, vol. 41, pp. 654-659, 1997.

Nerve fiber models: Once a potential field has been calculated, the excitation thresholds were determined for 2 types of myelinated nerve fibers using a rectangular voltage pulse of 210 μs: (1) Medial dorsal column (DC) fiber (12 μm) with collateral branches (4 μm) at every other node (2) Dorsal root (DR) fiber (15 μm) attached to a 12 μm lateral DC fiber. Parameters of both types of fibers were based on measurements on human myelinated nerve fibers.

The six electrode combinations shown in FIG. 7A were tested using a Medtronic Model 37082 bifurcated extension connected to one port of a Restore® implantable electrical stimulator and a 1×8 lead or extension into a second port (thus, resulting in a "4-8-4" electrode array). Reference is made to the alphabetic labels ("A," "B," etc.) in FIG. 7A, which are used to designate the electrode combinations. Electrode combination A is an example of an unguarded bipole electrode combination within the first class, and electrode combination B is an example of a guarded cathode electrode combination within the first class. Electrode combinations C-F are examples of guarded cathode electrode combinations within the second class. In the second computer model, the electrode contacts were modeled as rectangular voltage sources with a length of 3 mm and a width of 1 mm.

Figure 16A:
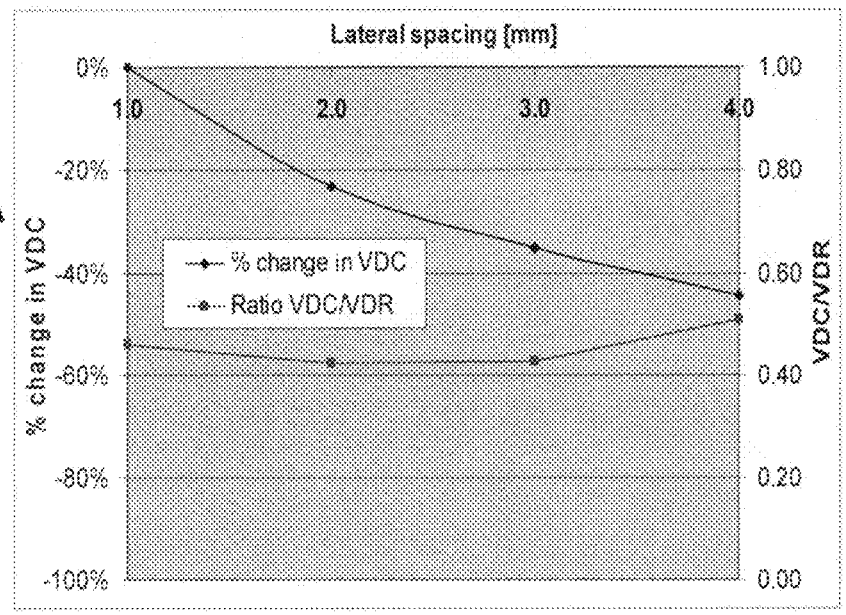
FIG. 16A-16B illustrate graphical displays generated via a second computer modeling example.

Effects of Lateral Spacing: Variation in lateral spacing between leads was modeled to characterize how it affects VDC and VDC/VDR. Combination 4C was used in the modeling. The results are summarized in FIG. 16A. FIG. 16A compares computer modeling results with 1×8 subcutaneous leads (about 4.5 mm center-to-center electrode spacing) guarded by two 1×4 leads (about 9.0 mm center-to-center electrode spacing) for each of the six electrode combinations shown in FIG. 7A (where the alphabetic label "A" in FIG. 7A corresponds to "4A" in FIG. 16A, and so forth for the labels B, C, D, E, and F). Lateral spacing of about 2 mm between each of the leads was used in the computer modeling, along with a 3.8 mm cerebral spinal fluid (CSF) thickness.

FIG. 16A shows that guarded cathode electrode combinations (4B-4F) within both the first and second classes result in a lower ratio of dorsal column stimulation threshold voltage to dorsal root stimulation threshold voltage (VDC/VDR) compared to an unguarded 2 electrode bipolar combination (4A). In general, guarding directly on either side of the cathode lowers VDC/VDR, but raises VDC, while guarding above and below the cathode lowers both VDC and VDC/VDR in most cases. Based on the modeling results, a clinician may select electrode combination 4D for implementation in a therapy program for a patient or for testing if preferential dorsal column threshold (i.e., the ability to reach deeper fibers within the spinal cord). On the other hand, the computer model suggests that combinations 4E and 4F may represent the best guarding combination for achieving low dorsal column stimulation threshold voltage (decreased current drain) relative to the simple two electrode bipolar electrode combination. Thus, if the clinician is interested in reducing power consumption of an electrical stimulation system, the clinician may select one of combinations 4E or 4F for testing on a patient.

FIG. 16A shows a small variation in VDC/VDR as a function of lateral spacing between about 1 and about 3 mm, suggesting that the guarded cathode electrode combination has a minimal effect on the ratio of desired to non-desired stimulation thresholds as a function of lateral spacing. Thus, based on the computer model, even if lateral spacing between adjacent leads is a consideration, the clinician may select any one the electrode combinations A-F (FIG. 7A). FIG. 16A also suggests there may be a benefit to increasing lateral spacing on VDC, which indicates, based on the second computer modeling, that larger lateral spacing may reduce the voltage required to achieve dorsal column stimulation without a significant tradeoff in the ratio of desired to non-desired stimulation thresholds.

Figure 16B:
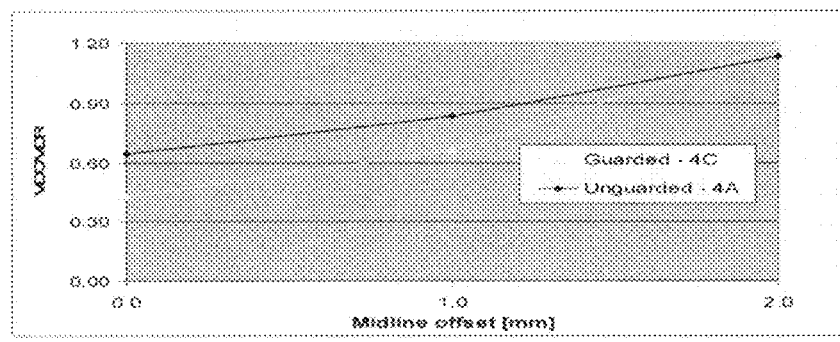

Another factor a clinician may consider when selecting a class of electrode combinations or specific combinations within the first or second classes for SCS is a distance of a lead and a midline of the spine of the patient. FIG. 16B shows computer modeling results of unguarded and guarded electrode combinations as the center lead is moved off of midline. Electrode combinations A and C (FIG. 7A) were used in the modeling with a lateral spacing of about 2 mm between leads. The modeling results shown in FIG. 16B suggests that a guarded cathode electrode combination maintains improved VDC/VDR versus a non-guarded cathode electrode combination up to a distance of about 2 mm off of midline. Based on computer modeling, selection of a guarded cathode electrode combination in the second class may reduce a dorsal column stimulation threshold voltage (VDC) and the ratio of dorsal column stimulation threshold voltage to dorsal root stimulation threshold voltage (VDC/VDR).

Computer Modeling Example 3

In a third computer modeling example, a plurality of electrode combinations from each of the two classes were modeled for two different cerebral spinal fluid (CSF) depths. A first depth of 3.8 mm represents a lower thoracic region of the spine and a second depth of 2.4 mm represents a cervical region of the spine. The electrode combinations that were tested are shown in FIG. 17A, and given the alphabetic designators A, B, C, D, E, and F. The third computer model suggested that guarded cathode electrode combinations (B-F) provide a lower recruitment ratio compared to unguarded bipolar electrode combination (A). Thus, if a clinician is interested in achieving a lower recruitment ratio, either electrode combination B from the first class or electrode combinations C-F may be selected as trial electrode combinations for further testing. A "trial, electrode combination" does not necessarily indicate that the electrode combination is tested during a trialing period, but may also include other therapy evaluation periods. On the other hand, if the clinician is interested in achieving a relatively high recruitment ratio, the clinician may select electrode combination A, which falls within the first class of electrode combinations as further testing. If electrode combination A is selected for use in chronic therapy delivery for the patient, the clinician may implant a single lead, rather than two or three leads, because only a single column of electrodes is necessary to achieve the combination A shown in FIG. 17A.

As indicated in FIG. 17A, the third computer model suggested that electrode combination D, which falls within the second class, has a lowest relative recruitment ratio, which indicates that in this modeling at least, combination D may be best for preferential dorsal column threshold (ability to reach to deeper fibers). FIG. 17B is a chart that measures a percent change in VDC (dorsal column voltage) for electrode combinations B-F relative to combination A. According to the third computer model, electrode combinations E and F provide the lowest VDC relative to pattern A, which decreases current drain. By decreasing current drain, the battery life of a medical device may be extended. The modeling shown in FIG. 17C suggests that at least according to the computer modeling used, longitudinal electrode combinations require the lowest amplitude relative to the other electrode combinations tested in order to achieve the same or similar dorsal column voltage.

Figure 18A:
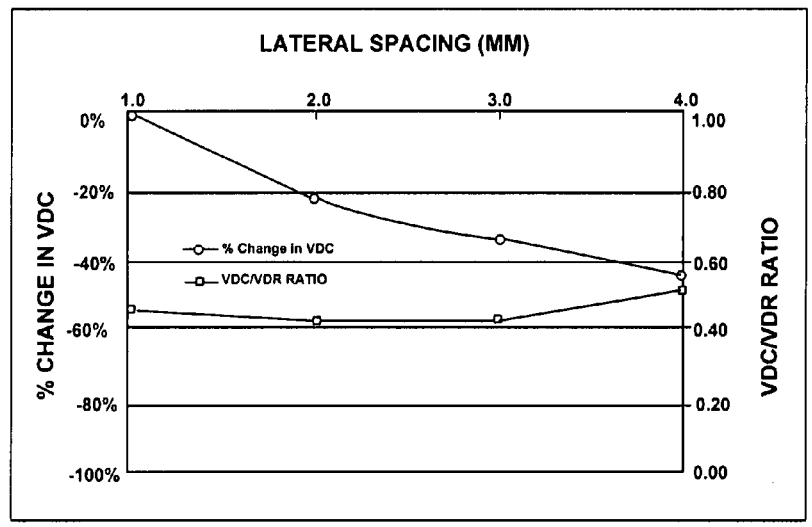
FIGS. 18A-C illustrate the results of computer modeling comparing different values for various electrode combinations.

The third computer modeling example also suggests a relationship between the electrode combinations from the first and second classes and an effect on recruitment ratio depending on the lateral spacing between columns of electrodes (e.g., lateral spacing between columns 32 and 34 of electrodes shown in FIG. 3). For example, FIG. 18A is a graph showing the effects of lateral spacing between columns of electrodes in a transverse electrode combination, which is within the second class. The graph shown in FIG. 18A was generated with the third computer model. As FIG. 18A shows, there is a relatively small change in recruitment ratio for a lateral spacing between about 1 mm and about 3 mm. After an approximately 3 mm spacing, however, the model shows that the recruitment ratio is increased. Thus, the third computer modeling example suggests that adjacent columns of electrodes may be spaced in a range of at least about 1 mm to about 3 mm between adjacent columns of electrodes without a significant tradeoff in the ratio of desired to nondesired stimulation thresholds.

Figure 18B:
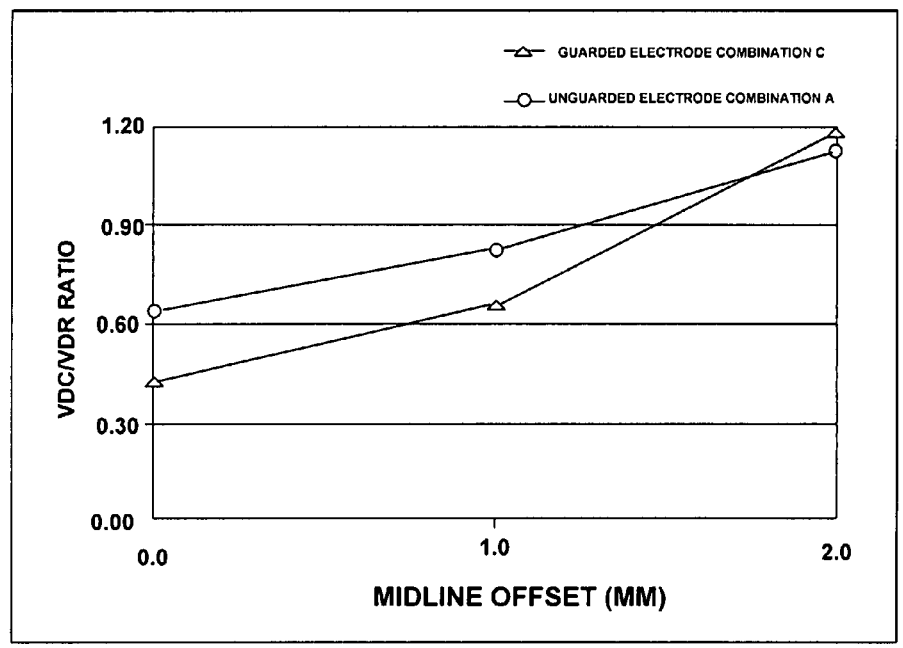

FIG. 18B is a graph comparing the recruitment ratio for unguarded and guarded cathode electrode combinations (which are shown in FIG. 18B) relative to a midline offset. A "midline offset" refers to the lateral offset from the midline of a spine, where the lateral direction is substantially perpendicular to a longitudinal axis of an elongated spine. As FIG. 18B shows, the guarded transverse electrode combination exhibits a better recruitment ratio compared to the unguarded bipole combination at up to about 1.8 mm off the midline of the spine. Thus, a clinician may prefer to test guarded transverse electrode combinations over an unguarded bipole electrode combination if one or more leads are to be implanted within a patient at a location that is offset up to about 1.8 mm from a midline of the spine.

Figure 18C:
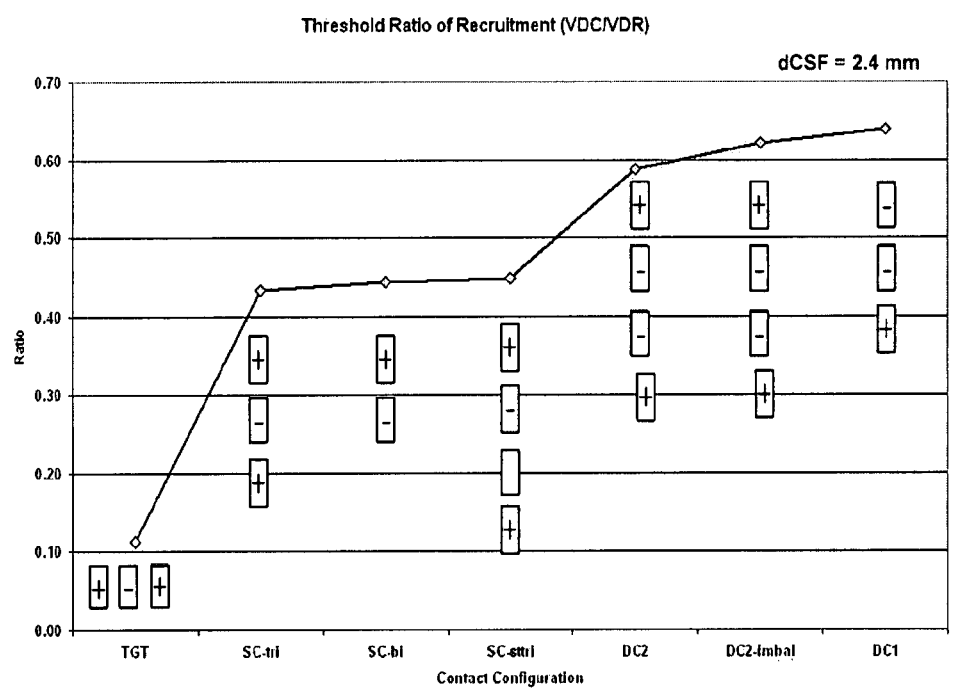

FIG. 18C is a graph comparing recruitment ratios for electrode combinations including one cathodes with electrode combinations including two cathodes. The modeling results shown in FIG. 18C suggest that a broader range of recruitment ratios may be obtained with electrode combinations including one cathode versus two. Accordingly, if a clinician is interested in achieving a broader range of recruitment ratios, the clinician may test electrode combinations within the first and second classes that include a single cathode.

In another embodiment, one or more optimal combinations of electrodes from among an array of electrodes implanted within a patient may be identified by initially testing electrode combinations representative of five or more groups of combinations. A preliminary determination of a group of electrode combinations that provide efficacious stimulation for the particular patient is first identified in order to minimize the number of electrode combinations that are tested, which helps efficiently identify effective electrode combinations for a particular patient. The techniques may be employed by either a clinician or patient, and may involve delivery of stimulation by an external medical device via percutaneously implanted leads during a trial period.

FIGS. 19A-23D are conceptual diagrams illustrating the representative electrode combinations from five groups of combinations that may be tested in accordance with the second embodiment. In each of FIGS. 19A-23D, distal portions of three leads 200, 202, and 204 are shown. However, three leads do not necessarily need to be implanted in order to implement the electrode combinations shown in FIGS. 19A-23D, because in some cases only one or two columns of electrodes may be used. In addition, in an alternate embodiment, a paddle lead may be used instead of three leads 200, 202, and 204.

Combinations representative of the first group of combinations are shown in FIG. 19A-C. The first group of electrode combinations (Group A) is characterized by the presence of caudal anodes, in which the anodes of the combination are located below the cathode(s) of the combination. As previously described, a "caudal" electrode is closer to a proximal end of a lead relative to another electrode. Thus, in Group A, a "caudal anode" indicates that anodes of the combination are closer to a proximal end of a lead than the cathodes of the combination. In FIG. 19A, a single anode 206 is disposed on the middle lead 202 and a single cathode 208 is located on lead 202 above the anode 206. In one embodiment, leads 200, 202, 204 are implanted in a patient such that center lead 202 is generally aligned with a midline of the patient. In that embodiment, the cathode 208, which is located on the middle lead 202, is referred to as a "midline cathode."

If a single lead is implanted within a patient, the combination shown in FIG. 19A may be implemented via any one of leads 200, 202 or 204. Cathode 208 is located closer to distal ends 200A, 202A, and 204B of leads 200, 202, and 204. In typical implant situations, the distal end of the lead 200A, 202A, 204A is rostral, and the proximal end is caudal. In FIG. 19B, two anodes 210A, 210B are located on leads 200, 204, respectively, and cathode 212 is located on middle lead 202 in a row above anodes 210A, 210B. In FIG. 19C, three anodes 214A-C are in substantially aligned rows on each lead 200, 202, 204 and cathode 216 is located on lead 202 in a row above anodes 214A-C.

Combinations representative of the second group of electrode combinations are shown in FIGS. 20A-C. The second group of electrode combinations (Group B) is characterized by the presence of rostral anodes, in which the anodes of the combination are located above the cathode(s) of the combination. In FIG. 20A, a single anode 218 is disposed on lead 202 and a single cathode 220 is located on lead 202 below the anode 218. Again, if a single lead is implanted within a patient, the combination shown in FIG. 20A may be implemented on any one of leads 200, 202 or 204. The particular lead 200, 202 or 204 may be selected based on, for example, the alignment with the midline of the patient. Anode 218 is located closer to distal ends 200A, 202A, and 204B of leads 200, 202, and 204. In FIG. 20B, two anodes 222A and 222B are located on leads 200, 204, respectively, while cathode 224 is located on lead 202 in a row below anodes 222A and 222B. In FIG. 20C, three anodes 226A-C are located in substantially aligned rows on each lead 200, 202, 204, and cathode 228 is located on lead 202 in a row below anodes 226A-C.

An electrode combination representative of the third group of electrode combinations is shown in FIG. 21. The third group of electrode combinations (Group C) includes guarded cathode configurations characterized by the presence of a single anode above and a single anode below the cathode(s) of the combination. In FIG. 21, a single cathode 230 is located on lead 202, while anodes 232A and 232B are above and below, respectively, the cathode 230. If a single lead is implanted within a patient, the combination shown in FIG. 20A may be implemented on any one of leads 200, 202 or 204.

Electrode combinations representative of the fourth group of electrode combinations are shown in FIGS. 22A-D. The fourth group of electrode combinations (Group D) is characterized by the presence of multiple anodes above and below the cathode(s) of the combination. In FIG. 22A, a cathode 234 is located on lead 202 in a row between anodes 236A-E. Anodes 236A-B are located in a row above cathode 234 on leads 200, 204, respectively, while anode 236C-E are located in a row below cathode 234 on leads 200, 202, 204, respectively. In FIG. 22B, the electrode combination is similar to that shown in FIG. 22A, where a cathode 238 is also located on lead 202 in a row between anodes 240A-E. However, the electrode arrangement is reversed in that three anodes 240A-C are located in a row above cathode 238, while two anodes 240D-E are located on leads 200 and 204 in a row below cathode 238.

In FIG. 22C, cathode 242 is located on lead 202, while anodes 244A-D are located in rows above and below cathode 242. In particular, anodes 244A-B are located on leads 200 and 204, respectively, in substantially aligned rows above cathode 242, while anodes 244C-D are located on leads 200 and 204, respectively, in substantially aligned rows below cathode 242. In FIG. 22D, cathode 246 is located on lead 202, while anodes 248A-F are located in rows above and below cathode 246. In particular, anodes 248A-C are located on leads 200, 202, and 204, respectively, in a row above cathode 246, while anodes 248D-F are located on leads 200, 202, and 204, respectively, in a row below cathode 246.

Figure 23A:
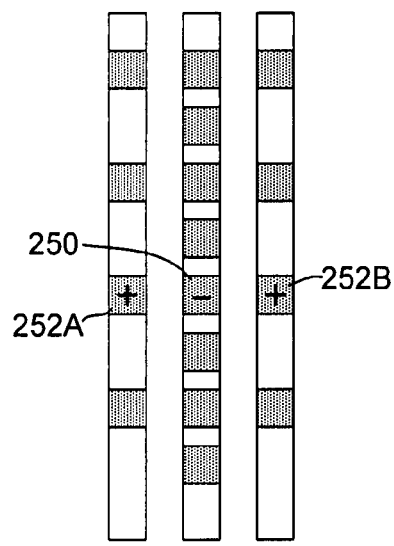
FIGS. 23A-D are schematic diagrams illustrating various representative electrode combinations from a fifth group of electrode combinations.
Figure 23B:
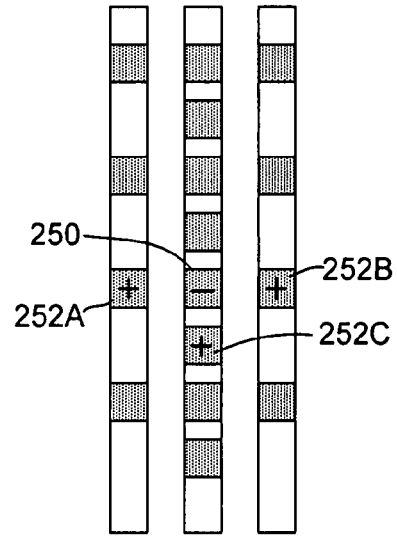
Figure 23C:
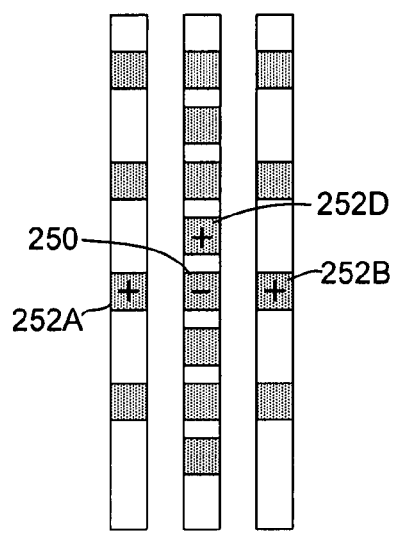
Figure 23D:
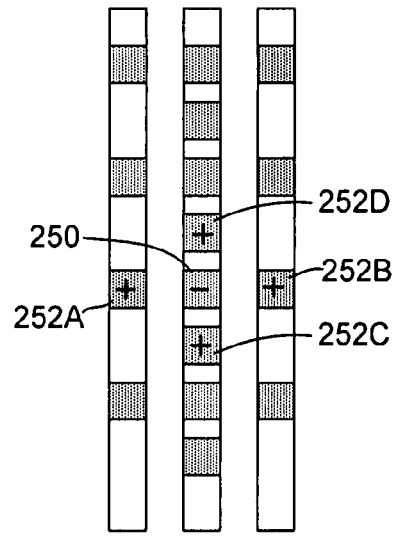

Electrode combinations representative of the fifth group of electrode combinations are shown in FIGS. 23A-D. The fifth group of electrode combinations (Group E) is characterized by the presence of transverse anodes, in which at least one anode of the combination is located substantially transverse to a cathode of the combination. In FIG. 23A, for example, a cathode 250 is located on lead 202 and in the same row as anodes 252A-B, which are located on adjacent leads 200, 204, respectively. The electrode combination shown in FIG. 23B is substantially similar to that shown in FIG. 23A, however, another anode 252C is located on lead 202 in a row below cathode 250. Similarly, the combination shown in FIG. 23C is similar to that shown in FIG. 23A, except that another anode 252D is located on lead 202 in a row above cathode 250. FIG. 23D is another conceptual diagram of an electrode configuration within the fifth group. The combination shown in FIG. 23D is a combination of those shown in FIGS. 23B-C, where cathode 250 is located on lead 202, and is surrounded by anodes 252A-D.

The five groups of electrode combinations are not limited to the electrode combinations shown in FIGS. 19A-23D, which are merely representative of the multitude of possible combinations meeting the criteria of one of the five groups, where the five groups are identified as Groups A-E. Other combinations may be within Groups A-E. For example, in other combinations of the five groups, the longitudinal position of each of the combinations may be different than that shown in FIGS. 19A-23D (i.e., the combination may be shifted away from ("down") or closer to ("up") the lead distal ends 200A, 202A, 204A. Alternatively, one or more anodes or cathodes may be shifted up or down, while the other anodes or cathodes remain in the position shown in FIGS. 19A-23D. Other permutations of the combinations may also be included in Groups A-E.

Figure 24:
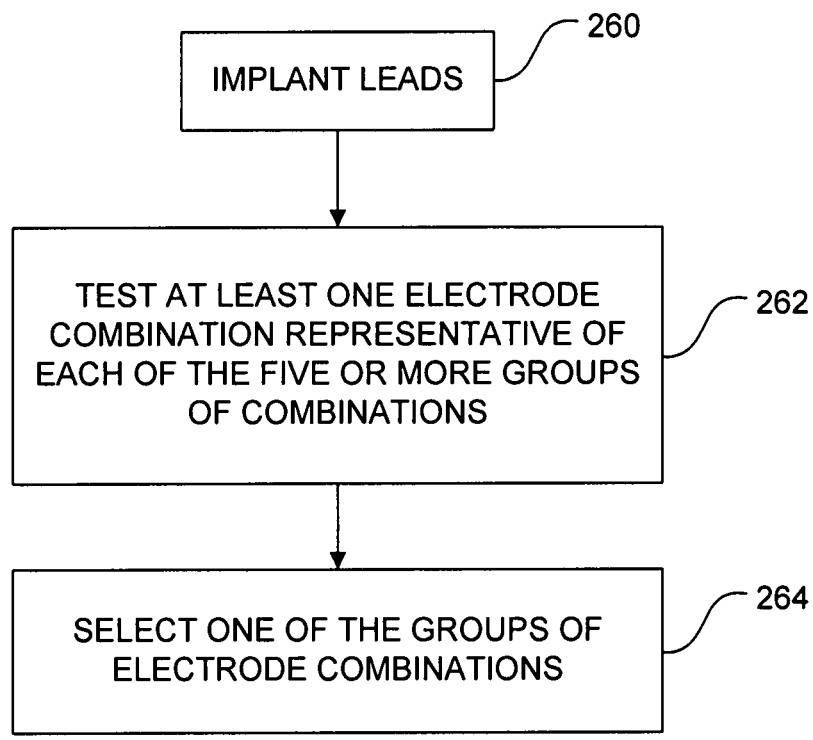
FIG. 24 is flow diagram illustrating an example process for selecting a group of electrode combinations that yields desired results for a patient.

FIG. 24 is a flow diagram illustrating an example method for selecting a group of electrode combinations from among a plurality of groups of electrode combinations, e.g., Groups A-E. Leads are implanted in a patient (260). If a paddle lead including multiple columns of electrodes is used, a single paddle lead may be implanted in the patient. Alternatively, there may be a paddle lead with two columns of electrodes, and a percutaneous lead with a single column of electrodes. As previously discussed, one or more leads may already be implanted in the patient, and so the clinician may retrofit the existing leads to achieve the desired configuration of leads (e.g., a 4-8-4 configuration or a 5-6-5 configuration). Following implantation of the leads (260), an electrode combination from one of the five representative groups of combinations is selected, for example by a clinician, medical device programmer or another computing device (262). In one embodiment, the electrode combination is selected from a clinician library, which may include a plurality of electrode combinations in the various groups, and which the clinician may use to test combinations within the groups. For example, the clinician library may include two combinations from each of Groups A, B, D, and E, and the combination illustrated in FIG. 21 from Group C. The clinician and/or patient may then select one or more groups of combinations that results in effective therapy for the patient or are more effective as compared to the other tested groups (264).

As discussed below, the clinician may further test within the selected groups or may utilize the selected group(s) as a starting point for initiating another testing methodology for further fine-tuning an electrode combination. While an effective electrode combination or nearly-effective electrode combination may be found among tested combination from Groups A-E of, it may be desirable to fine-tune the electrode combination by testing similar electrode combinations and/or implementing algorithms that, for example, generate electrode combinations based on the selected group, or test combinations at different longitudinal positions, mirror image combinations, and other permutations of one or more electrode combinations from the selected groups.

Figure 25:
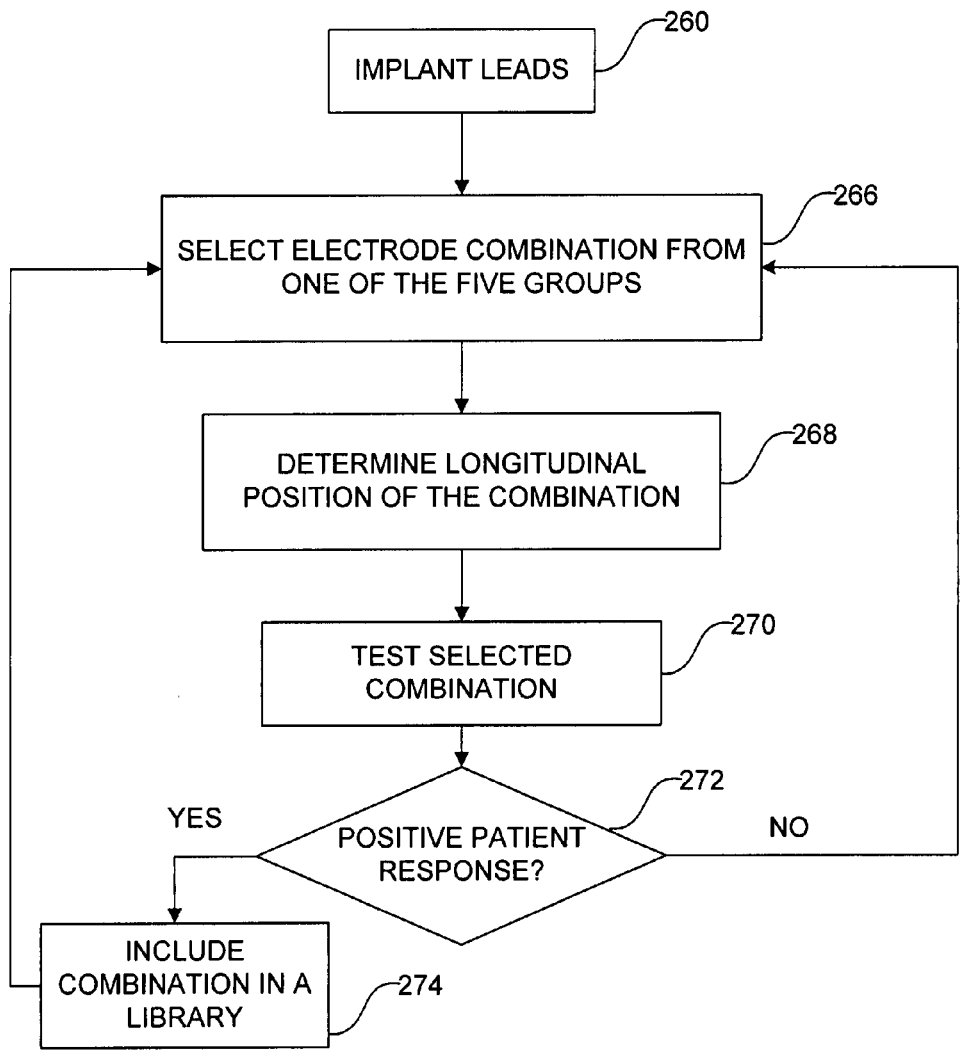
FIG. 25 is flow diagram illustrating another example process for selecting a group of electrode combinations that yields desired results for a patient.

FIG. 25 is a flow diagram illustrating another example method for selecting a group of electrode combinations from among a plurality of groups of electrode combinations, e.g., Groups A-E. Leads are implanted in a patient (260), and an electrode combination from one of Groups A-E is selected (266). Initially, at least two combinations from each of Groups A, B, D, and E are stored in a programmer, such as a screening or clinician programmer. The combinations may include, for example, the combinations shown in FIGS. 19A-23D. As in the example method of the first embodiment in which a class of electrode combinations is selected, discussed with reference to FIG. 5A, a longitudinal position of the selected electrode combination is determined (268). The longitudinal position may be determined using known methods, such as by selecting a test electrode combination, and "moving" the longitudinal position of the combination, e.g., by selecting similar combinations at different longitudinal positions within an electrode array, until a location best suited for the patient is determined (e.g., based on patient feedback as to the efficacy of the longitudinal position or any resulting side effects). Automated methodologies for finding an effective longitudinal position may be employed, such as TargetStim™, which is available from Medtronic, Inc. of Minneapolis, Minn.

Upon finding a useful longitudinal position for the combination (268), the clinician may test the electrode combination by instructing a medical device to implement the electrode combination on the leads for a relatively short duration (e.g., a few minutes) via the programmer (270). This testing may involve increasing the voltage or current amplitude of the stimulation delivered via the combination, and identifying one or more effects, such as amplitude for paresthesia (the sensation of stimulation), strong but comfortable stimulation, or intolerable stimulation. The clinician may then determine whether the electrode combination is suited for the patient based on the patient response (272). If the patient provides positive feedback for the electrode combination (e.g., the tissue stimulation provides pain relief, results in a minimal number of side effects, provides an adequate therapeutic range between threshold levels, and does not require high amplitudes for efficacy), the clinician may include the electrode combination in a patient library or a clinician library (274). If desired, the clinician may repeat steps 266, 268, 270, 272 and 274 to add more electrode combinations to the patient library or the clinician library. It is preferred that the clinician test at least one electrode combination from each of Groups A-E because of the varying therapeutic effects the combination's of Groups A-E may provide based on computer model predictions.

If the electrode combination does not result in a positive response from the patient, the clinician may repeat steps 266, 268, 270, 272 and 274, and select another electrode combination to test. This may be repeated until the clinician finds an electrode combination that yields positive results for the patient, or until the clinician adds a suitable number of electrode combinations to the patient library. Alternatively, a patient may generate the patient library outside of the clinic by performing steps 266, 268, 270, 272, and 274.

After the steps shown in FIG. 25 have been completed, the library (patient, clinician, or otherwise generated) includes one or more electrode combinations that have been identified to be potentially suitable for the patient. The library may include electrode combinations from only one group, or from all five groups.

Figure 26:
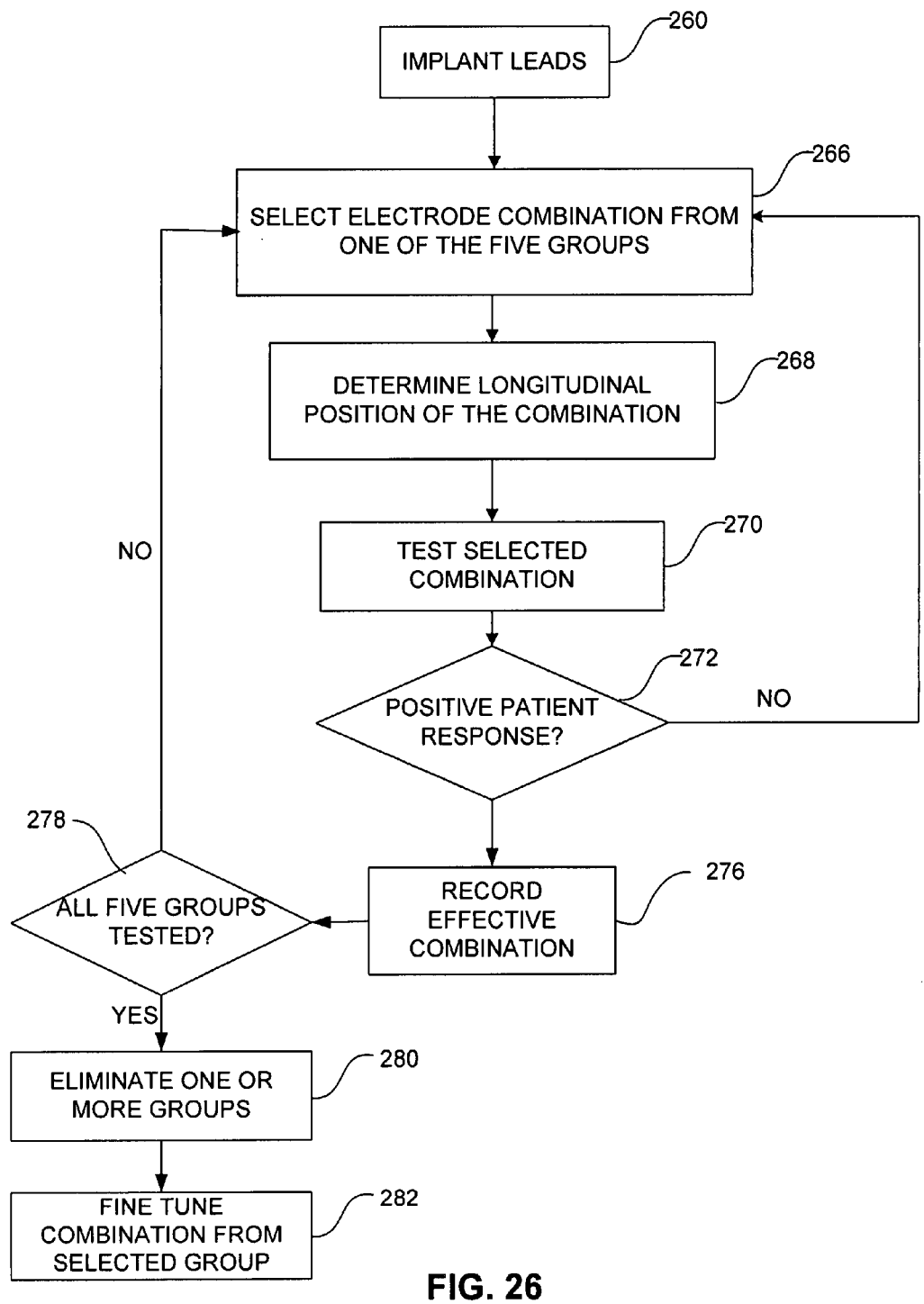
FIG. 26 is flow diagram illustrating another example process for selecting a group of electrode combinations that yields desired results for a patient, where the process include refining the selected group or selected combinations within the group.

In an alternate method, as shown in FIG. 26, the clinician may record each effective electrode combination or the group to which the electrode combination belongs resulting from the testing of Groups A-E for use in further optimization (276). The electrode combinations that yielded a positive result during the initial testing of the five groups (i.e., the "subset" of combinations) may be recorded in the patient programmer, the clinician programmer, the implantable or external stimulator, another computing device or any suitable type of log or journal (276). The clinician may determine whether combinations from each of Groups A-E have been tested (278). If not, the steps 266, 268, 270, 272 and 276 may be repeated until combinations from the five groups have been tested. In some embodiments, it may not be necessary to re-determine an effective longitudinal position of each combination (268).

If the subset of combinations spans more than one of Groups A-E of electrode combinations, the clinician may retest the combinations within the subset in order to eliminate one or more groups (280). Alternatively, the clinician may test another combination from the groups represented by the subset in order to eliminate one or more groups (280). For example, if the subset consists of the combination shown in FIG. 19A of the first group and the combination shown in FIG. 20A of the second group, the clinician may retest the combinations of FIG. 19A or FIG. 20A and/or the clinician may test the other combinations within the first and second groups (e.g., the combinations shown in FIGS. 19B-C and FIGS. 20B-C).

If desired, the clinician may utilize all of the electrode combinations resulting from the initial testing within the five groups in the optimization process described below, rather than eliminating one or more groups within the subset.

Upon completion of the initial testing of combinations representative of the five groups (Groups A-E), the clinician may implement another programming methodology in order to further optimize and refine the stimulation parameters, which include an electrode combination (282). For example, the clinician may utilize known methodologies, such as the ones described above with reference to FIG. 5B, using the recorded electrode combination(s) or an electrode combination representative of the recorded group(s) as a starting point for the optimization methodology. The resulting, refined electrode combination may or may not be a part of the same one of Groups A-E identified using the techniques described above, or any of Groups A-E. The optimization methodology may, for example, lead to testing outside of the five groups.

Fine-tuning the one or more combinations (282) may be used to develop a library of electrode combinations for further testing by the patient or clinician. For example, the technique shown in FIG. 6B or 7 with respect to the embodiment involving testing combinations from two classes may be also be used with the embodiment involving testing combinations from Groups A-E. Furthermore, in some embodiments, the clinician may manually, or with the aid of a computing device such as a programmer, order the five or more groups according to one or more user-selected criteria. The criteria may include, for example, patient needs, a clinician preference, pain location(s) of the patient, lead implant sites, and so forth. The ordering may rank the different groups based on the selected criterion. For example, if the clinician orders the group according to the one that provides the best stimulation for treating lower back pain, the programmer may rank Groups A-E accordingly. The ordering may be based on the effects for a particular patient, which may be based on testing one or more programs within each group, or may be based on a general set of therapy metrics or other therapy efficacy indicators that are not specific to a particular patient.

Thus, in one embodiment, following formulation of the library from the fine-tuning or the patient library developed in the technique shown in FIG. 25, the patient may test each of the electrode combinations in the library in accordance with the technique shown in FIG. 6B or 7 or a similar technique. During the patient testing, such as when the patient first tests each of the combinations in the library for a relatively short duration of time, the patient may record feedback data relating to the testing of each electrode combination in the library, such as in a patient data booklet previously described, the table shown in FIG. 27, or by inputting feedback data into a computing device (block 86 of FIG. 5B). The table shown in FIG. 27 provides different sections for receiving data, such as the pattern number or program for the electrode combination tested, a section for recording another combination tested if the combination was not provide with a pattern number or program number by the clinician, the top cathode level (i.e., the particular electrode having the most caudal cathode), the threshold amplitudes tested, coverage areas of pain relief, and different ratings, e.g., a comfort rating and an overall rating. The table shown in FIG. 27 may be provided in electronic form or on paper. The patient may further narrow down the combinations in the patient library to a subset of combinations that yield the best results (block 88 of FIG. 5B). For example, the patient may test each of the combinations in the subset for a longer duration of time (e.g., one to three days), and record the results of the testing. Based on this testing, the patient may further narrow the number of combinations in the subset.

A clinician may determine which of Groups A-E of electrode combinations provided the best results for the patient based on this subset of combinations, which may affect the number of leads to be permanently (i.e., not temporarily) implanted in the patient (block 90 of FIG. 5B). For example, if it is determined that a single column electrode combination from the first class provides the best results, the clinician may implant a single lead. On the other hand, if it is determined that a transverse tripole electrode combination from the first class of electrodes provides the best results, the clinician may need to implant three leads or a paddle lead including at least three columns of electrodes.

The technique illustrated in FIG. 6 may be modified to select a group of electrode combinations that yields the best results for a patient. For example, rather than testing twelve electrode combinations representative of each of the two classes, the patient may test the combinations shown in FIGS. 19A-23D that are representative of Groups A-E or other electrode combinations that are representative of Groups A-E. In alternate embodiments, the number of programs tested, the duration of the testing, and the number of the "best" selected programs may differ.

Figure 28:
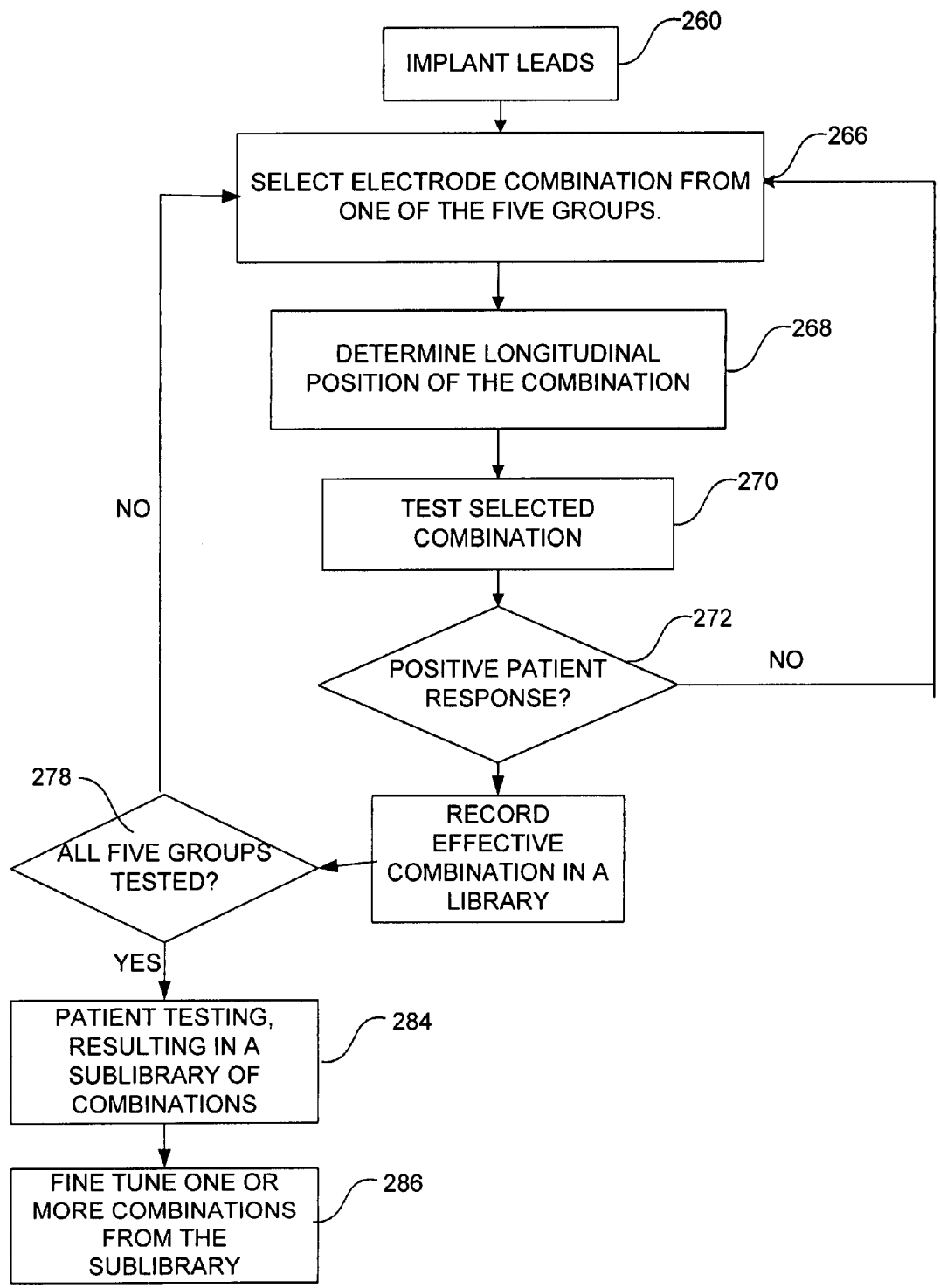
FIG. 28 is a flow diagram illustrating another example process for selecting a group of electrode combinations that yields desired results for a patient.

In some embodiments, the fine-tuning of a best-suited electrode combination may occur after patient testing of combinations from within Groups A-E. FIG. 28 illustrates one example technique in which an electrode combination is fine-tuned using an optimization methodology after the patient testing. Following testing one or more combinations from Groups A-E and recording the combinations that yield a positive result in a library (276), the patient may further test the programs within the library (284). For example, the patient may test the combinations within the library on an out-clinic basis following the technique illustrated in FIG. 5B (particularly blocks 84, 86, and 88) or FIG. 6. A sublibrary of one or more effective electrode combinations may result from the patient testing (284). The clinician or patient may then fine-tune one or more combinations from the sublibrary by, for example, initiating an optimization methodology for each of the combinations in the sublibrary (i.e., using each of the combinations in the sublibrary as a starting point for the optimization methodology) (286).

Figures 29, 30:
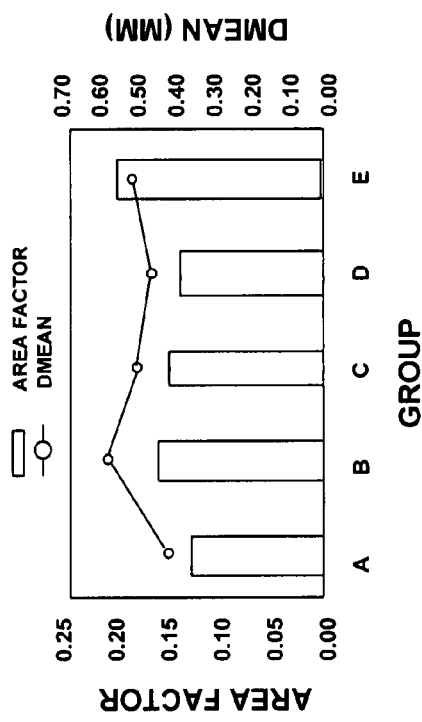
FIG. 29 is a table listing a plurality of metrics for five groups of electrode combinations.
FIG. 30 is a graph comparing the relative performance of electrode combinations from within five groups with respect to area factor and mean depth of dorsal column recruitment (DMEAN).

As in the previous embodiment, a clinician may reference a table of efficacy metrics, such as the one shown in FIG. 29, to minimize the number of electrode combination groups to test. The clinician may, for example, follow the technique shown in FIG. 13. In particular, the clinician may refer to the table of efficacy metrics in order to determine which electrode combinations and/or which groups of electrode combinations are best suited to optimizing one or more metrics for a particular patient. The efficacy metrics shown in FIG. 29 are similar to those shown in FIG. 12, and include VDC (dorsal column voltage), VDC/VDR (recruitment ratio), usage range, DMEAN (the mean depth of the recruited area), area factor (medial-lateral mean), mid-span (the middle of the excited DR span relative to a center of the cathode of the combination, where a positive number indicates a rostral direction relative to the cathode and a negative indicates a caudal direction with respect to the cathode), DR span (the distance (in centimeters) of dorsal root activation at the maximum amplitude). Other metrics could also be calculated in other embodiments.

The values shown in FIG. 29 are representative of the mean value for each of Groups A-E, and were formulated using a finite element computer program (Ansoft Maxwell 3D, available from Ansoft Corporation of Pittsburgh, Pa.) and a neuron simulation program (NEURON, which is available from Yale University) to predict the effects of spinal cord stimulation using various electrode combinations in a 4-8-4 arrangement of electrodes, where the center lead (including a 1×8 electrode arrangement) was centered on a midline and the CSF thickness was about 3.8 mm. The metric values shown in FIG. 29 are merely representative of one computer model, and other computer models may yield different results. However, it is believed that the metric values shown in FIG. 29 are useful for comparing the metrics of the electrode combinations of Groups A-E.

A clinician may access a database including a plurality of electrode combinations of Groups A-E and associated therapy metric values in order to quickly ascertain the therapy attributes of each of the combinations. For example, the clinician may refer to the table shown in FIG. 29, or another table or data structure including metrics for the electrode combinations of Groups A-E, in order to quickly ascertain the features of the combinations. For example, if the clinician desires to deliver a stimulation therapy according to an electrode combination that results in a high UR, the clinician may reference the table shown in FIG. 29 and compare the UR values for Groups A-E. The table of FIG. 28 shows that electrode combinations within Groups B and E result in the highest relative UR values based on a first computer modeling system, which was described above in reference to FIG. 15. Based on the UR values, the clinician may choose to test electrode combinations Groups B and E, rather than testing combinations from all five groups. In an alternate embodiment, the clinician may choose to compare a different efficacy metric value.

The present invention also contemplates a system in which a table of efficacy metrics is provided to a clinician for the purposes of selecting at least one of Groups A-E of electrodes combinations or set of electrode combinations to test. The information contained in the table may be in any form, and does not necessarily need to be provided in a table. For example, the information might also include graphical displays of the zone of recruited axons in a plane of the spinal cord that is transverse to the axis of the cord. Furthermore, the table may be electronic and include features for user interaction. For example, the system may prompt a user to select one or more efficacy metrics to view, or to input a target value of one or more efficacy metrics. Alternatively, a computer program may select an optimal electrode combination based on the desired parameters for the metric, which may be entered into a computing system by the clinician.

FIG. 30 shows a graph that may be presented to a clinician via a display of a computing device, where the graph may be useful for comparing the performance of Groups A-E with respect to area factor and DMEAN. The results of the computer modeling shown in FIGS. 29 and 30 suggest that combinations from Group B provide the best depth of stimulation penetration (DMEAN), but with relatively broad activation (area factor) relative to Groups A and C-E. The computer modeling also suggests that combinations from Group E provide a relatively good balance between depth of penetration (DMEAN) and narrow activation with the dorsal columns (area factor). Other useful graphical displays include graphical displays of the zone of recruited axons (i.e., the recruitment area) in a plane of the spinal cord that is transverse to the axis of the spinal cord. Such graphical displays may be similar to the graphical display shown in FIG. 15.

FIGS. 31A-B chart results of the computer modeling and compare the fiber selectivity attributes of each of Groups A-E. FIG. 31A is a graph comparing the VDC/VDR from the computer modeling with the VDC for each of Groups A-E. FIG. 31B is a graph comparing the VDC/VDR from the computer modeling with a value equal to about (1/UR). The results of the computer modeling results of FIG. 29 and illustrated in FIGS. 31A-B suggest that Group E provides the best recruitment of dorsal column fibers versus dorsal root fibers (i.e., RR) compared to the other groups, as well as the best UR. For each of Groups A-E, the RR was inversely related to UR.

FIGS. 32A-B chart results of the computer modeling and compare the dorsal root activation attributes of each of Groups A-E. FIG. 32A is a graph comparing the DR span of each of Groups A-E, while FIG. 32B is a graph comparing the mid-span values for each of Groups A-E. The results of the computer modeling shown in FIG. 29 and FIGS. 32A-B suggest that the electrode combinations of Groups C and D exhibit the shortest span of dorsal root activation. Activation of dorsal roots can be focused near the cathode with the electrode combinations within Groups C-E (as shown in FIG. 32B), spread rostrally (toward the head of the patient) with the electrode combinations within Group B, or spread caudally (toward the feet of the patient) with the electrode combinations within Group A.

In other embodiments, one or more optimal combinations of electrodes from among an array of electrodes implanted within a patient may be identified by initially testing electrode combinations representative of any suitable number of groups of combinations, where each group has different electrode combination characteristics that may result in the different electrical stimulation fields when stimulation is delivered via the particular electrode combinations representative of the groups. The techniques described herein are not limited to testing within five or six groups of electrode combinations, but may also include testing within fewer than five groups of electrode combinations or greater than six groups.

In one embodiment, one or more optimal combinations of electrodes are identified by initially testing electrode combinations representative of six groups of combinations. The six groups of electrode combinations include Groups A-E described above as well as a sixth group (referred to as "Group F") characterized by one or more off-center cathodes. Just as with the previously described technique that included testing within five groups of electrode combinations, in a technique that includes testing within six groups of electrode combinations, a preliminary determination of a group of electrode combinations that provide efficacious stimulation for the particular patient is made in order to minimize the number of electrode combinations that are tested. For example, any of the techniques shown in FIGS. 24-26 and 28 with respect to testing combinations representative of five groups of electrodes may be adapted to testing combinations representative of six groups of electrodes (Groups A-F). Any of the techniques described herein may be employed by either a clinician or patient, and may involve delivery of stimulation by an external or implanted medical device via percutaneously or surgically implanted leads during a trial period.

Each of Groups A-E is characterized by an electrode combination that includes one or more cathodes along a center column of electrodes. For example, as shown in FIG. 19B, an electrode combination of Group A includes cathode 212 along middle lead 202. In contrast, Group F includes one or more off-center cathodes. Based on computer modeling, it is believed that electrode combinations that include at least one off-center cathode are useful for recruiting the dorsal root more preferentially than combinations that include a centrally-located cathode.

Examples of electrode combinations representative of Group F are shown in FIGS. 33A-C. Other electrode combinations including off-center cathodes are contemplated. In FIG. 33A, a single anode 288 is disposed on middle lead 202 and cathodes 290A and 290B are located on adjacent leads 200, 204, respectively. As FIG. 33A illustrates, cathodes 290A and 290B are off center relative because cathodes 290A-B are not located on center lead 202. In the 4×8×4 electrode configuration shown in FIG. 33A, anode 288 and cathodes 290A-B are in the same row of electrodes. In one embodiment, leads 200, 202, 204 are implanted in a patient such that center lead 202 is generally aligned with a midline of the patient. In that embodiment, anode 288, which is located on middle lead 202, may be referred to as a "midline anode."

FIG. 33B illustrates an electrode combination that includes anode 288 and cathodes 290A-B of the combination shown in FIG. 33A, in addition to anode 292 along middle lead 202, and cathodes 294A-B on leads 200, 204 adjacent to middle lead 202. Anodes 292 and cathodes 294A-B are arranged similarly to anode 288 and cathodes 290A-B.

FIG. 33C illustrates another electrode combination within Group F. The combination includes two center anodes 296A-B along middle lead 202 and two off-center cathodes 298A-B on leads 200 and 204, respectively. In embodiments in which the combination shown in FIG. 33C is achieved on a 4×8×4 electrode configuration as shown in FIG. 33C, anodes 296A-B are located on separate rows of electrodes, and cathodes 298A-B are located on separate rows and columns of electrodes.

FIG. 34A illustrates table 300 of therapy efficacy metric values that were calculated for the electrode combination of Group F shown in FIG. 33A using the commercially available finite element software Ansoft Maxwell 3D, available from Ansoft of Pittsburgh, Pa. Representations for white and gray matter of the spinal cord, dura mater, CSF, epidural fat, and vertebral bone were based on the geometries of the University of Twente low-thoracic model. Voltage boundary conditions were used in the computer model to calculate the electric field generated by a particular electrode combination. A neuron simulation program (Neuron v. 5.8, available through the web site of Yale University of New Haven, Conn.) is used to calculate the response and thresholds of DC and DR fibers.

The therapy metric values shown in table 300 suggest that the off-center cathode combination shown in FIG. 33A, and possibly the other off-center cathode electrode combinations of Group F, result in a relatively high recruitment ratio (VDC/VDR). As previously discussed, a VDC/VDR value over one suggests that the dorsal root is preferentially recruited. Compared to, for example, the electrode combinations comprising middle cathodes that were modeled with respect to the table shown in FIG. 12, the off-center cathode combination results in a relatively high VDC/VDR.

Depending on the placement of the electrode array relative to a patient's torso, a relatively high recruitment ratio (VDC/VDR) may result in paresthesia felt above the waistline, which may be beneficial for treating back pain. When the electrode combination shown in FIG. 33A is used to deliver therapy to a patient and middle lead 202 is substantially along a midline of the patient's back, it is believed that cathodes 290A-B shield the dorsal fibers along the midline, thereby preferentially recruiting the dorsal roots.

The computer modeling shown in FIG. 34A also suggests that the modeled combination from Group F results in a relatively low DMEAN, which is indicative of the mean depth of the recruited area from the middle of the dorsal spinal cord. As compared to the combinations modeled in FIG. 12, the off-center cathode combination results in a relatively low DMEAN.

FIG. 34B illustrates table 302 of therapy efficacy metric values that were calculated for the electrode combination of Group F shown in FIG. 33C using the same commercially available finite element software Ansoft Maxwell 3D and the University of Twente low-thoracic model geometries. The therapy metric values shown in table 302 suggest that the off-center cathode combination shown in FIG. 33C, results in a higher recruitment ratio (VDC/VDR) than the electrode combinations comprising one or more middle cathodes (e.g., the combinations modeled to generate the table of efficacy metric values shown in FIG. 12), but a relatively low recruitment ratio as compared to the electrode combination shown in FIG. 33A. Thus, the modeling suggests that stimulation delivered via the electrode combination including a single anode 288 and two cathodes 290A-B results in a more preferential recruitment of the dorsal roots compared to the dorsal fibers. In other words, stimulation delivered via the electrode combination including two anodes 296A-B and two cathodes 298A-B results in a more preferential recruitment of the dorsal fibers compared to the dorsal roots.

In addition, the efficacy metrics shown in table 302 also suggest that the combination shown in FIG. 33C, which includes two anodes 296A and 296B, has a lower dorsal column voltage (VDC) compared to the combination shown in FIG. 33C. VDC represents the voltage for stimulating a dorsal column fiber on the midline at the boundary between white matter and cerebral spinal fluid (also referred to as dorsal column voltage). Thus, the lower VDC of the electrode combination shown in FIG. 33C also suggests that the combination shown in FIG. 33C results in a more preferential recruitment of the dorsal fibers compared to the dorsal roots.

In Tables 300 and 302 of FIGS. 34A an 34B, respectively, the therapy metric "X. S.D." indicates a standard deviation of the lateral spread of the activation of the dorsal column fibers from a midline of the patient's spine. The higher X. S.D. metric for the electrode combination shown in FIG. 33C compared to the combination shown in FIG. 33A (a value of 2.03 compared to 0.435) indicates that the combination of FIG. 33C results in a wider stimulation pattern than the combination of FIG. 33A.

A table of therapy metric values, e.g., a table similar to the table shown in FIG. 12 including more than one electrode combination within Group F, i.e., electrode combinations including off-center cathodes, may be generated using any suitable computer modeling technique, such as the McIntyre-Richardson-Grill myelinated fiber model or the University of Twente model described above. As described below with respect to FIG. 35, a clinician may select one or more electrode combinations to test based on a table of therapy efficacy metrics. In one embodiment, the modeling results may be incorporated into a software program executing on a computing device to present a relatively easy user interface with which the clinician may select electrode combinations within one of Groups A-F (or within one of the two classes).

In some cases, one or more electrode combinations for a particular patient may be selected by initially testing within the first and second classes of electrode combinations, and determining whether to implant one, two or three columns of electrodes in the patient. Thereafter, the clinician and/or patient may test electrode combinations representative of Groups A-E or combinations representative of Groups A-F that are relevant to the particular electrode column configuration selected for the patient.

As previously indicated, in some cases, a clinician may select electrode combinations to test using a table of metric values, such as, but not limited to, the table shown in FIG. 12 or the table shown in FIG. 29. For example, the clinician may compare at least one metric value for a baseline electrode combination (i.e., a combination tested on a patient) to the metric values for a plurality of additional electrode combinations, where the additional electrode combinations are representative of the first and second classes of combinations or the five groups (Groups A-E) of combinations. The clinician may search for an electrode combination that has a different a metric value than the baseline electrode combination. The metric may include, but are not limited to, a dorsal column current, usage range, a ratio of dorsal column stimulation threshold voltage to dorsal root stimulation threshold voltage, a recruitment area, an area factor, a maximum output voltage, or a dorsal column stimulation threshold voltage. Other metrics could also be calculated by a computer model.

In another embodiment, a table of efficacy metrics is provided to a clinician for the purposes of initially selecting a class of electrodes combinations or set of electrode combinations to test.

In either embodiment, a computer program or another automated program may be presented to a clinician on a computing device. The computing device may present a user interface, such as the schematic user interface shown in FIG. 35, with which the clinician may interact. For example, the clinician may enter one or more baseline electrode combinations to modify in screen 310. The baseline electrode combination may be an electrode combination that has been initially tested on the patient or one selected from a table of combinations and corresponding metric values. For example, the initially tested baseline combination may result in a UR that is too low. While the baseline electrode combination is indicated to be "Electrode Combination 1" in FIG. 35, in other embodiments, any suitable system of identifying a particular combination may be used.

Figure 35:
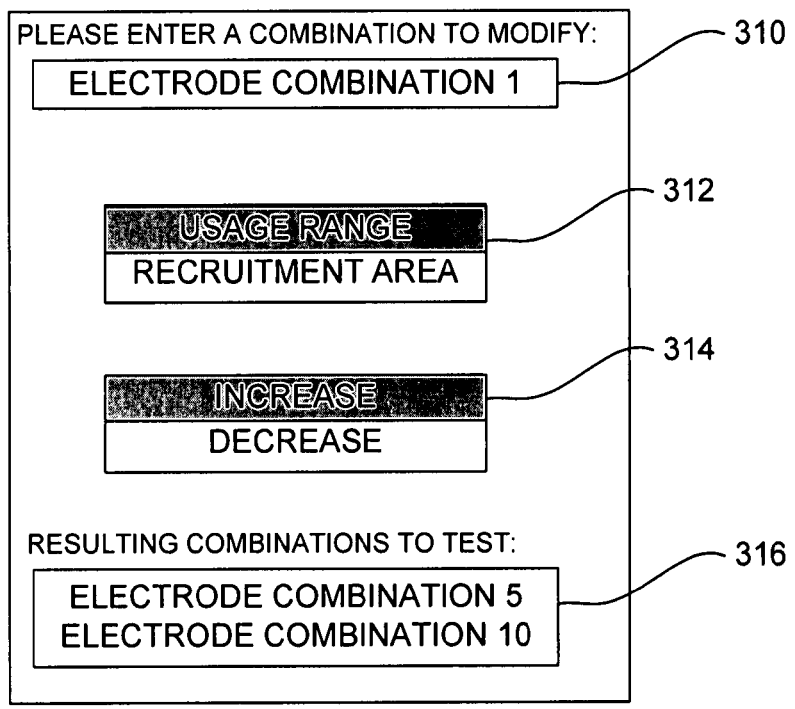
FIG. 35 is a conceptual user interface for a computer program that enables a clinician to select one or more metric values to modify based on a baseline electrode combination.

The clinician may interact with a computer program via user interface shown in FIG. 35 to indicate to the computer program that the clinician wishes to determine an electrode combination that results in a UR that is greater than the baseline combination. For example, the clinician may interact with the user interface and select one or more metrics to modify in menu 312, which may be a pull down menu or a scroll menu and select an "increase" or "decrease" option/modifier in menu 314. The menu 314 may be up/down arrows in another embodiment. The computer program may then output one or more combinations in screen 316 that meet the criteria indicated by the clinician (i.e., increase or decrease the selected metric based on the baseline combination entered in screen 310). Alternatively, the computer program may output one or more classes or groups of electrode combinations in screen 316 that meet the criteria indicated by the clinician.

In one technique, the computer program may initially look within the same class or group of combinations as the baseline combination in order to find a combination that meets the metric value requirements inputted by the clinician, and then direct the medical device to implement the combination for testing. The baseline combination may also be representative of a preferred group or class. In another embodiment, rather than entering a baseline combination to test, the clinician may indicate the preferred class or group. If none of the combinations within the preferred class or group can satisfy the desired modification, the programmer might look to other classes for a candidate, perhaps with a notification to the user that the search is continuing outside the class indicated by the clinician to be preferred.

In some cases, the clinician may not wish to search for combinations outside of the preferred class or group. For example, after initially testing combinations from each of the two classes and/or each of the five or six groups, the clinician may select a preferred class or one or more preferred groups. The clinician may then employ a computer program to optimize one or more therapy metrics from among the preferred group. After the initial testing within the classes and/or groups, the clinician may not wish to essentially "reverse" progress made during the initial step, and accordingly, in such cases, the clinician may customize the computer program to operate under a rule set that causes the computer program to search within the preferred class or group. However, in some cases, the clinician may still choose to search outside of a preferred class or group.

Figure 36:
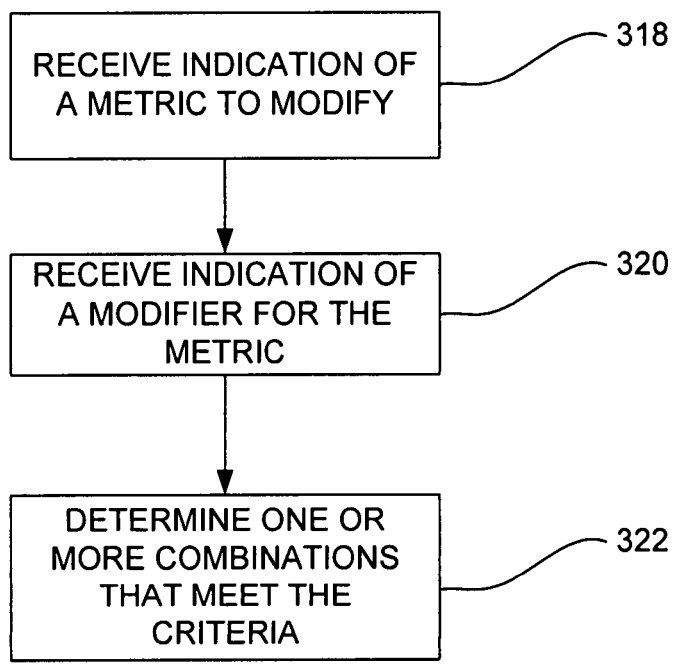
FIG. 36 is a flow diagram illustrating an example process of determining one or more electrode combinations that meet criteria indicated by a clinician.

FIG. 36 is a flow chart illustrating a technique for selecting one or more combinations or a class or group of combinations to test based on an indication of a criteria from a clinician. As discussed in reference to FIG. 35, the criteria may be in the form of a metric to modify, and a modifier for the metric. In the technique shown in FIG. 36, after receiving an indication of one or more metrics to modify (318), and one or more modifiers for the metric (320) (e.g., increase or decrease), one or more combinations (or a class or group of combinations) that meets the criteria is determined (322). The combinations that meet the criteria may be determined, for example, by referencing a table of metric values (e.g., as shown in FIG. 29) or by a similar method.

Furthermore, although leads including substantially cylindrical lead bodies are used in the examples of the invention, the present invention is applicable to combinations of electrodes disposed on a paddle lead. FIG. 37 is a picture illustrating an example of a paddle lead 330. As FIG. 37 illustrates, the paddle lead 330 is a paddle shaped, and is typically disposed at a distal end of a lead body (not shown), which connects proximal end 330A of paddle lead 330. Paddle lead 330 includes electrodes 332A-H arranged in a two dimensional array. Electrodes 332A-D make up a column, while electrodes 332E-F make up another column, and electrodes 332G-H make up another column.

Figure 38:
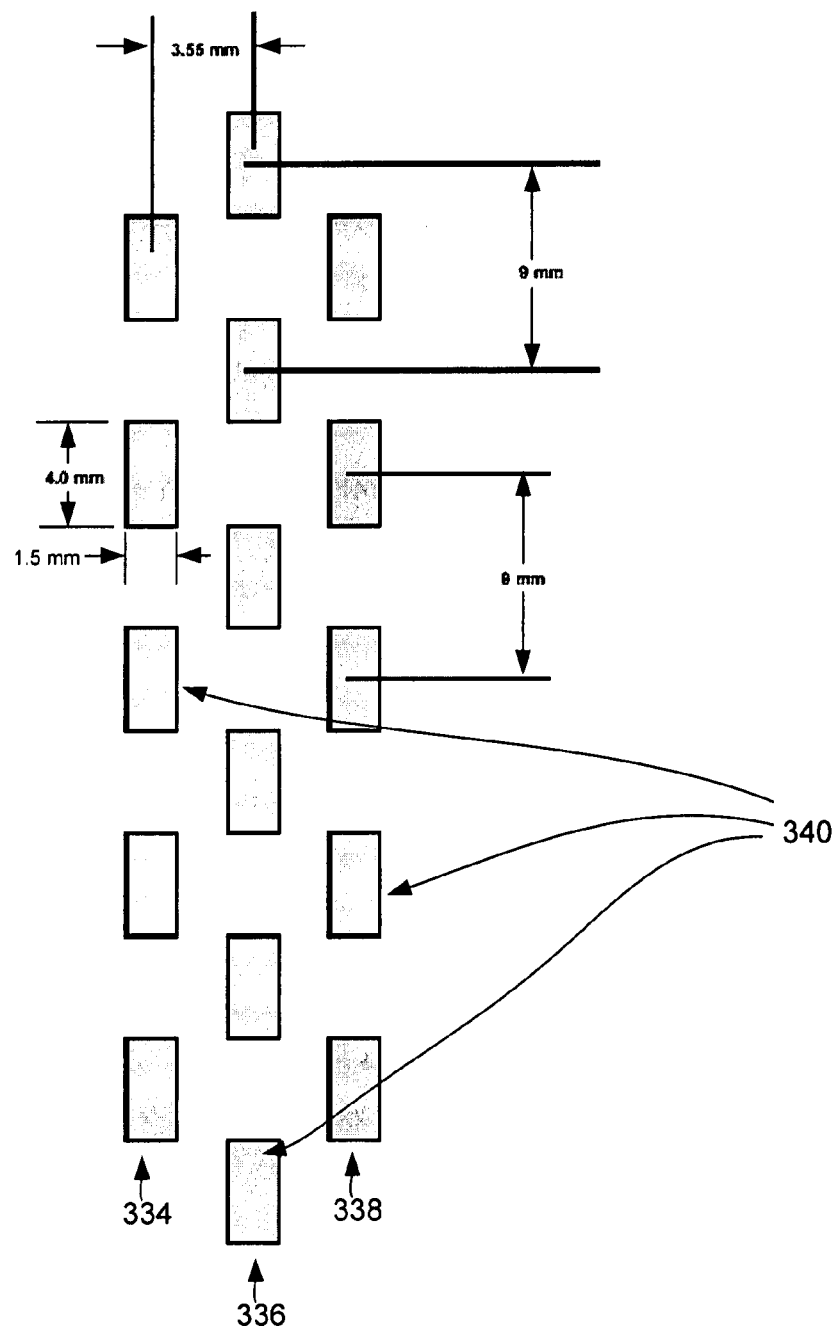
FIG. 38 is a schematic diagram of a 5-6-5 electrode arrangement defined by three columns of electrodes.

FIG. 38 is a conceptual diagram of a 5-6-5 electrode pattern, which includes a first column 334 of five electrodes, a second column 336 of six electrodes, and a third column 338 of five electrodes. Example dimensions for one embodiment of a 5-6-5 electrode pattern are also shown in FIG. 38. In particular, in the embodiment shown in FIG. 38, each electrode 340 is about 4 mm by about 1.5 mm, and each row within the columns 334, 336, 338 are separated by about 9 mm (measured from a center of one electrode 340 to an adjacent electrode 340 in the column). Each column 334, 336, 338 of electrodes are separated by about 3.55 mm, which is measured from center of one electrode 340 to an adjacent electrode 340 in the adjacent row. Computer model-generated metrics can be calculated for electrode combinations using the dimensions and patterns available with the lead shown in FIG. 38, just as they were done for three columns of leads in a 4-8-4 array of electrodes in the embodiments described above.

U.S. Patent Application Publication No. 2006/0122678, which was published on Jun. 8, 2006 and has common ownership with the present application, describes an implantable neurostimulation lead kit that may be used in accordance with the techniques described herein. U.S. Patent Application Publication No. 2006/0122678 is herein incorporated by reference in its entirety. Furthermore, all patents and publications referenced in the description and figures are herein incorporated by reference in their entirety.

In each of the techniques described above, when testing two or more electrode combinations, the system and method described commonly-assigned U.S. patent application Ser. No. 11/352,389, entitled, "SHIFTING BETWEEN ELECTRODE COMBINATIONS IN ELECTRICAL STIMULATION DEVICE" and filed on Feb. 10, 2006, which is incorporated by reference in its entirety, may be employed. U.S. patent application Ser. No. 11/352,389 describes a technique for shifting between two electrode combinations. An amplitude of a first electrode combination is incrementally decreased while an amplitude of a second, or subsequent, electrode combination is concurrently incrementally increased. The stimulation pulses of the first and second electrode combinations are delivered to the patient interleaved in time. In this manner, the invention provides for a smooth, gradual shift from a first electrode combination to a second electrode combination, thereby allowing the patient to maintain a continual perception of stimulation. Such shifting may be used to identify a longitudinal position for an electrode combination, or may be used as a technique to make minor modifications to a selected electrode combination from a selected one of groups of electrode combinations, i.e., as a technique to fine tune such an electrode combinations.

In other embodiments, other techniques for shifting between two or more electrode combinations may be employed. For example, the stimulation energy may be time-interleaved between electrode combinations, as described in commonly-assigned U.S. patent application Ser. No. 11/401,100 by Steven Goetz et al., entitled, "SHIFTING BETWEEN ELECTRODE COMBINATIONS IN ELECTRICAL STIMULATION DEVICE," and filed on Apr. 10, 2006, the entire content of which is incorporated herein by reference. In the time-interleave shifting embodiment, the amplitudes of the first and second electrode combinations are ramped downward and upward, respectively, in incremental steps until the amplitude of the second electrode combination reaches a target amplitude. The incremental steps may be different between ramping downward or ramping upward. The incremental steps in amplitude can be of a fixed size or may vary, e.g., according to an exponential, logarithmic or other algorithmic change. When the second electrode combination reaches its target amplitude, or possibly before, the first electrode combination can be shut off.

As another example, electrical stimulation and in particular, the current, between two electrode combinations of respective therapy programs may be shifted between electrodes of two electrode combinations by reducing an amplitude delivered to an electrode of one combination relative to the increase in amplitude an electrode of another combination. In such embodiments, the electrical stimulator may include at least two current sources.

In the electrode combinations described herein, regardless of whether the combination is from one or more of the classes or at least five groups of electrode combinations described above, such as Groups A-F, stimulation signals including different stimulation characteristics, e.g., stimulation amplitudes, may be provided to at least two of the electrodes of the combination. For example, stimulation signals comprising different stimulation amplitudes may be provided to cathodes 290A and 290B of the electrode combination shown in FIG. 33A. The amplitude of stimulation or other stimulation characteristic that is provided to each of the cathodes 290A and 290B may be determined during a trial phase. For example, the amplitudes provided to cathodes 290A and 290B may be optimized using a programming methodology (also referred to as optimization methodologies), which may or may not be the same as a programming methodology used to further optimize the anode and cathode patterns. In some cases, a difference in stimulation amplitudes between the stimulation signal provided to cathodes 290A and 290B may result in a stimulation field that is no longer representative of Group F of electrode combinations.

Furthermore, in each electrode combination that includes two or more cathodes, stimulation may be provided to the cathodes substantially simultaneously or within a range of time that results in stimulation pulses that contribute to a substantially common electrical field.

Various embodiments of the invention have been described. These and other embodiments are within the scope of the following example descriptions. Furthermore, although the present invention has been described with reference to a spinal cord stimulation application, the present invention is not limited to such an embodiment. Rather, the present invention also applies to other therapy applications in which electrical stimulation is delivered to a patient via one or more columns of electrodes.

The invention claimed is:

1. A method comprising delivering stimulation to a patient via at least one of three columns of electrodes implanted within the patient, wherein at least one of the three columns of electrodes extends in a longitudinal direction wherein the stimulation is delivered according to a trial electrode combination from each of at least five groups of electrode combinations during a therapy evaluation period, wherein a first group is characterized by a rostral anode electrode pattern, a second group is characterized by a caudal anode electrode pattern, a third group is characterized by a first cathode disposed between two anodes, the first cathode and anodes being located in a same column of electrodes, a fourth group is characterized by a second cathode disposed between a first row of anodes and a second row of anodes, and a fifth group is characterized by a transverse electrode combination, wherein anodes of the transverse electrode combination are displaced substantially transversely relative to a third cathode of the transverse electrode combination and relative to the longitudinal direction, and a stimulation field resulting from delivery of stimulation via the transverse combination is oriented substantially transversely relative to a target tissue for the stimulation.

2. The method of claim 1, further comprising:
   selecting the trial electrode combination from one of the at least five groups;
   delivering stimulation via electrodes at a plurality of longitudinal positions of the columns of electrodes;
   receiving feedback from the patient relating to delivery of stimulation at each of the longitudinal positions; and
   selecting one of the longitudinal positions based on the feedback,
   wherein delivering stimulation according to the trial electrode combination from each of the at least five groups of electrode combinations comprises delivering stimulation at the selected longitudinal position.

3. The method of claim 1, further comprising selecting at least one of the groups as a preferred group.

4. The method of claim 3, further comprising:
   receiving feedback from a patient relating to the stimulation delivered; and
   selecting the preferred group based on the feedback.

5. The method of claim 4, wherein receiving feedback from the patient comprises receiving feedback via a user interface of a programming device.

6. The method of claim 4, further comprising selecting a lead configuration for implantation within the patient based on the preferred group.

7. The method of claim 6, wherein selecting a lead configuration comprises selecting a number of percutaneously implantable leads to implant within the patient.

8. The method of claim 3, further comprising:
   selecting additional electrode combinations within the preferred group to test on the patient; and
   delivering stimulation via the additional electrode combinations.

9. The method of claim 3, wherein selecting at least one of the groups as the preferred group comprises selecting at least two of the groups as first and second preferred groups, the method further comprising:
   selecting a first set of additional electrode combinations within the first preferred group to test on the patient; and
   delivering stimulation via the first set of additional electrode combinations;
   receiving patient feedback relating to the stimulation via the first set of additional electrode combinations;
   selecting a second set of additional electrode combinations within the second preferred group to test on the patient;
   delivering stimulation via the second set of additional electrode combinations; and
   receiving patient feedback relating to the stimulation via the second set of additional electrode combinations; and
   selecting the first preferred group or the second preferred group as a better fit for the patient based on the patient feedback.

10. The method of claim 9, further comprising selecting an additional electrode combination for the patient from within the first and second sets based on the patient feedback.

11. The method of claim 3, further comprising:
    accessing a database comprising a list of electrode combinations from the at least five groups of electrode combinations and at least one associated therapy metric value indicative of therapy efficacy; and
    selecting at least one electrode combination from the preferred group based on the at least one therapy metric value associated with the selected electrode combination.

12. The method of claim 11, further comprising receiving user input selecting one of a plurality of therapy metrics, wherein the therapy metrics each comprise a quantifiable result of delivery of stimulation, and wherein selecting at least one electrode combination from the preferred group based on the at least one therapy metric value associated with the selected electrode combination comprises selecting at least one electrode combination from the preferred group based on the user-selected metric.

13. The method of claim 12, wherein selecting at least one electrode combination from the preferred group based on the user-selected metric comprises selecting at least one electrode combination that optimizes the user-selected therapy metric as compared to a remainder of electrode combinations within the list.

14. The method of claim 13, wherein the at least one therapy metric includes at least one of: a dorsal column current; usage range; a ratio of dorsal column stimulation threshold voltage to dorsal root stimulation threshold voltage; a recruitment area; an area factor; a maximum output voltage; or a dorsal column stimulation threshold voltage.

15. The method of claim 13, further comprising:
    selecting at least one electrode combination from the preferred group based on information associating a plurality of electrode combinations from the at least five groups with a value of at least one therapy metric, wherein the therapy metrics comprise a quantifiable result of delivery of stimulation;
    delivering stimulation via the at least one selected electrode combination;
    receiving patient feedback relating to the stimulation delivered via the at least one selected electrode combination; and
    selecting an additional electrode combination outside of the preferred group based on the information associating the plurality of electrode combinations from the at least five groups with the value of at least one therapy metric.

16. The method of claim 3, further comprising optimizing a member electrode combination from the preferred group.

17. The method of claim 16, wherein optimizing the member electrode combination from the preferred group comprises:
    applying each of a plurality of rules to the member electrode combination, each of the rules defining a respective electrode combination modification based on at least one of proximity of active electrodes within the member electrode combination to each other, proximity of inactive electrodes within the member electrode combination to active electrodes, or number of active electrodes within the member electrode combination; and
    generating a plurality of child electrode combinations based on the application of the rules to the member electrode combination.

18. The method of claim 17, further comprising:
    applying at least one of the rules to at least one of the child electrode combinations; and
    generating at least one second generation child program based on the application of the rule to the child electrode combination, the second generation child program including a second generation child electrode combination.

19. The method of claim 18, wherein optimizing the member electrode combination from the preferred group comprises:
   delivering electrical stimulation to the patient via the member electrode combination;
   receiving patient feedback relating to the efficacy of the therapy delivered via the member electrode combination;
   selecting at least one therapy metric indicative of therapy efficacy based on the patient feedback; and
   selecting an additional electrode combination by accessing a database comprising a list of electrode combinations from the at least five groups of electrode combinations and at least one associated therapy metric value.

20. The method of claim 1, further comprising ordering the groups based on a user-selected criterion.

21. The method of claim 20, wherein the user-selected criterion comprises a patient-specific therapy requirement, a clinician preference, a pain location or a lead implant site.

22. The method of claim 1, further comprising:
   receiving patient feedback to the stimulation delivered via each trial electrode combination; and
   storing each trial electrode combination in a library if the patient provides a positive response to the respective trial electrode combination.

23. The method of claim 22, further comprising delivering stimulation according to each trial electrode combination stored within the library based on selections made by the patient.

24. The method of claim 1, wherein the at least five groups of electrode combinations further comprises a sixth group characterized by at least one off-center cathode.

25. A system comprising:
   a medical device;
   an array of implantable electrodes coupled to the medical device, wherein the array defines a first electrode column and wherein at least one of the first, second, and third electrode columns extends in a longitudinal direction, a second electrode column, and a third electrode column; and
   a memory that stores at least one electrode combination from each one of at least five groups of electrode combinations, wherein the medical device delivers therapy to a patient via the array of implantable electrodes according to a trial electrode combination from each of the at least five groups, the at least five groups comprising:
      a first group characterized by a rostral anode electrode pattern;
      a second group characterized by a caudal anode electrode pattern;
      a third group characterized by a first cathode disposed between two anodes, the first cathode and anodes being located in a same one of the first, second or third electrode columns;
      a fourth group characterized by a second cathode disposed between a first row of anodes and a second row of anodes; and
      a fifth group characterized by a transverse electrode combination, wherein anodes of the transverse electrode combination are displaced substantially transversely relative to a third cathode of the transverse electrode combination and relative to the longitudinal direction, and a stimulation field resulting from delivery of stimulation via the transverse combination is oriented substantially transversely relative to a target tissue for the stimulation.

26. The system of claim 25, wherein the at least five groups comprises a sixth group of electrode combinations characterized by an off-center cathode.

27. The system of claim 25, wherein the medical device comprises the memory.

28. The system of claim 25, further comprising a programming device comprising the memory, wherein the programming device is configured to control the medical device to deliver stimulation via each of the electrode combinations stored in the memory.

29. The system of claim 25, further comprising a computing device comprising a user interface, a processor, and the memory, wherein the processor is configured to receive user input via the user interface selecting one of the at least five groups of electrode combinations as a preferred group and generate a list of electrode combinations based on the preferred group of electrode combinations for further testing.

30. The system of claim 29, wherein the memory further stores a plurality of rules, each of the rules defining a respective electrode combination modification based on at least one of proximity of active electrodes to each other, proximity of inactive electrodes to active electrodes, or number of active electrodes within a representative electrode combination of the preferred group, and the processor is configured to select a parent electrode combination within the preferred group, apply each of the plurality of rules to the parent electrode combination, and generates the list of electrode combinations based on application of the rules to the parent electrode combination.

31. The system of claim 25, wherein the memory stores a plurality of electrode combinations from each one of the at least five groups of electrode combinations and associated values of at least one therapy metric.

32. The system of claim 31, further comprising a computing device comprising the memory, wherein the computing device further comprises a processor and a user interface configured to receive an indication of a selected therapy metric from a user, and wherein the processor outputs at least one selected electrode combination from within the plurality of electrode combinations based on the selected therapy metric.

33. The system of claim 31, further comprising a computing device comprising a user interface, a processor, and the memory, wherein the processor is configured to control a medical device to deliver electrical stimulation therapy to a patient via a baseline electrode combination selected from a preferred group, receive patient feedback relating to the therapy delivery via the baseline electrode combination, select a therapy metric based on the patient feedback, and select an additional electrode combination from among the plurality of electrode combinations stored within the memory based on the selected therapy metric.

34. The system of claim 33, wherein the baseline electrode combination is within one of the at least five groups of electrode combinations, and wherein the additional electrode combination is within the same group as the baseline electrode combination.

35. The system of claim 33, wherein the baseline electrode combination is within one of the at least five groups of electrode combinations, and wherein the additional electrode combination is not within the same group as the baseline electrode combination.

36. The system of claim 25, wherein the first electrode column is disposed on a first implantable lead, the second electrode column is disposed on a second implantable lead, and the third electrode column is disposed on a third implantable lead.

37. The system of claim 25, wherein at least two of the first, second or third columns of electrodes are disposed on a paddle lead.

38. The system of claim 25, wherein the medical device comprises an implantable or external medical device.

39. A medical device programmer comprising:
a memory that stores a plurality of electrode combinations for an electrical stimulator, wherein the plurality of electrode combinations includes at least one electrode combination from each of at least five groups of electrode combinations, the at least five groups comprising:
a first group characterized by a rostral anode electrode pattern;
a second group characterized by a caudal anode electrode pattern;
a third group characterized by a first cathode disposed between two anodes, the first cathode and anodes being located in a same column of electrodes;
a fourth group characterized by a second cathode disposed between a first row of anodes and a second row of anodes; and
a fifth group characterized by a transverse electrode combination, wherein anodes of the transverse electrode combination are displaced substantially transversely relative to a third cathode of the transverse electrode combination and relative to a longitudinal direction defined by at least one column of electrodes extending in the longitudinal direction, and a stimulation field resulting from delivery of stimulation via the transverse combination is oriented substantially transversely relative to a target tissue for the stimulation; and
a processor that controls delivery of electrical stimulation to a patient via the electrical stimulator in accordance with at least one electrode combination from each of the first, second, third, fourth, and fifth groups.

40. The programmer of claim 39, wherein the at least five groups comprises a sixth group characterized by an off-center cathode.

41. The programmer of claim 39, further comprising a user interface to receive input from a user, wherein the input comprises feedback relating to therapy effects from the delivery of electrical stimulation to a patient via the electrical stimulator in accordance with at least one electrode combination from the first, second, third, fourth, and fifth groups.

42. The programmer of claim 39, wherein the memory associates a value of at least one therapy metric with each electrode combination of the plurality of electrode combinations.

43. The programmer of claim 42, further comprising a user interface to receive input from a user indicating a selected therapy metric, wherein the processor outputs at least one selected electrode combination from within the plurality of electrode combinations based on the selected therapy metric.

44. A non-transitory computer-readable medium comprising instructions that cause a processor to control an electrical stimulator to:
deliver electrical stimulation to a patient during a therapy evaluation period via an electrode combination from each of at least five groups of electrode combinations, the at least five groups comprising:
a first group of electrode combinations characterized by a rostral anode electrode pattern;
a second group of electrode combinations characterized by a caudal anode electrode pattern;
a third group of electrode combinations characterized by a first cathode disposed between two anodes, the first cathode and anodes being located in a same column of electrodes;
a fourth group of electrode combinations characterized by a second cathode disposed between a first row of anodes and a second row of anodes; and
a fifth group of electrode combinations characterized by a transverse electrode combination, wherein anodes of the transverse electrode combination are displaced substantially transversely relative to a third cathode of the transverse electrode combination and relative to a longitudinal direction defined by at least one column of electrodes extending in a longitudinal direction, and a stimulation field resulting from delivery of stimulation via the transverse combination is oriented substantially transversely relative to a target tissue for the stimulation.

45. The computer-readable medium of claim 44, wherein the at least five groups comprises a sixth group characterized by an off-center cathode.

46. A computing device comprising:
a memory comprising a plurality of electrode combinations and associated therapy metric values, wherein the plurality of electrode combinations comprises at least one electrode combination from at least five groups of electrode combinations, the at least five groups comprising:
a first group characterized by a rostral anode electrode pattern;
a second group characterized by a caudal anode electrode pattern;
a third group characterized by a first cathode disposed between two anodes, the first cathode and anodes being located in a same column of electrodes;
a fourth group characterized by a second cathode disposed between a first row of anodes and a second row of anodes; and
a fifth group characterized by a transverse electrode combination, wherein anodes of the transverse electrode combination are displaced substantially transversely relative to a third cathode of the transverse electrode combination and relative to a longitudinal direction defined by at least one column of electrodes extending in the longitudinal direction, and a stimulation field resulting from delivery of stimulation via the transverse combination is oriented substantially transversely relative to a target tissue for the stimulation;
a display; and
a processor that generates a graphical display illustrating at least one electrode combination from the plurality of electrode combinations and the associated therapy metric value to a user via the display.

47. The computing device of claim 46, wherein the processor presents an interactive graphical interface via the display, the graphical interface comprising a first section for receiving user input selecting a therapy metric and a second section, wherein the processor provides an output via the second section that indicates at least one of a preferred group of electrode combinations selected from the first, second, third, fourth or fifth groups, or an additional electrode combination that optimizes the therapy metric.

48. The computing device of claim 46, wherein processor presents a data structure presenting the plurality of electrode combinations and associated therapy metric values via the display.

49. The computing device of claim 46, wherein the therapy metric includes at least one of: a dorsal column current; usage range; a ratio of dorsal column stimulation threshold voltage to dorsal root stimulation threshold voltage; a recruitment area; an area factor; a maximum output voltage; or a dorsal column stimulation threshold voltage.

50. The computing device of claim 46, wherein the at least five groups of electrode combinations comprises a sixth group characterized by an off-center cathode.

51. A method comprising:
- selecting, by a medical device programmer, a therapy metric; and
- selecting, by the medical device programmer, at least one group from a set of at least five groups of electrode combinations that optimizes the therapy metric, the set of at least five groups comprising:
  - a first group of electrode combinations characterized by a rostral anode electrode pattern;
  - a second group of electrode combinations characterized by a caudal anode electrode pattern;
  - a third group of electrode combinations characterized by a first cathode disposed between two anodes, the first cathode and anodes being located in a same column of electrodes;
  - a fourth group of electrode combinations characterized by a second cathode disposed between a first row of anodes and a second row of anodes; and
  - a fifth group of electrode combinations characterized by a transverse electrode combination, wherein anodes of the transverse electrode combination are displaced substantially transversely relative to a third cathode of the transverse electrode combination and relative to a longitudinal direction defined by at least one column of electrodes extending in the longitudinal direction, and a stimulation field resulting from delivery of stimulation via the transverse combination is oriented substantially transversely relative to a target tissue for the stimulation.

52. The method of claim 51, wherein selecting, by the medical device programmer, at least one group from the set of at least five groups of electrode combinations that optimizes the therapy metric comprises reviewing, by the medical device programmer, a data structure comprising at least one electrode combination from each of the at least five groups and associated metric values.

53. The method of claim 51, wherein the set of at least five groups comprises a sixth group of electrode combinations characterized by an off-center cathode.

* * * * *